(12) United States Patent
Gildea et al.

(10) Patent No.: US 7,422,852 B2
(45) Date of Patent: *Sep. 9, 2008

(54) DETECTION OF NUCLEIC ACID USING LINEAR BEACONS

(75) Inventors: Brian D. Gildea, Billerica, MA (US); James M. Coull, Westford, MA (US); Jens J. Hyldig-Nielsen, Holliston, MA (US); Mark J. Fiandaca, Acton, MA (US)

(73) Assignee: Boston Probes, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/610,337

(22) Filed: Jun. 30, 2003

(65) Prior Publication Data

US 2007/0178471 A1 Aug. 2, 2007

Related U.S. Application Data

(62) Division of application No. 09/950,459, filed on Sep. 10, 2001, now Pat. No. 6,649,349, which is a division of application No. 09/179,162, filed on Oct. 26, 1998, now Pat. No. 6,485,901.

(60) Provisional application No. 60/063,283, filed on Oct. 27, 1997.

(51) Int. Cl.
*C12Q 1/68* (2006.01)
*C12P 19/34* (2006.01)

(52) U.S. Cl. .......................................... 435/6; 435/91.2

(58) Field of Classification Search .................. 435/6, 435/91.2
See application file for complete search history.

(56) References Cited

U.S. PATENT DOCUMENTS

| | | | |
|---|---|---|---|
| 4,174,384 A | 11/1979 | Ullman | |
| 4,261,968 A | 4/1981 | Ullman | |
| 4,542,104 A | 9/1985 | Stryer | |
| 4,666,862 A | 5/1987 | Chan | |
| 4,725,536 A | 2/1988 | Fritsch | |
| 4,725,537 A | 2/1988 | Fritsch | |
| 4,766,062 A | 8/1988 | Diamond | |
| 4,822,733 A | 4/1989 | Morrison | |
| 4,868,103 A | 9/1989 | Stavrianopoulos | |
| 4,996,143 A | 2/1991 | Heller | |
| 5,118,801 A | 6/1992 | Lizardi | |
| 5,210,015 A | 5/1993 | Gelfand | |
| 5,237,515 A | 8/1993 | Herron | |
| 5,288,611 A | 2/1994 | Kohne | |
| 5,312,728 A | 5/1994 | Lizardi | |
| 5,348,853 A | 9/1994 | Wang et al. | 435/6 |
| 5,439,793 A | 8/1995 | Rose | |
| 5,439,797 A | 8/1995 | Tsien | |
| 5,487,972 A | 1/1996 | Gelfand et al. | 435/6 |
| 5,491,063 A | 2/1996 | Fisher | |
| 5,514,546 A | 5/1996 | Kool | |
| 5,527,675 A | 6/1996 | Coull | |
| 5,538,848 A | 7/1996 | Livak | |
| 5,539,082 A | 7/1996 | Nielsen | |
| 5,573,906 A | 11/1996 | Bannwarth | |
| 5,601,984 A | 2/1997 | Kohne | |
| 5,607,834 A | 3/1997 | Bagwell | |
| 5,612,183 A | 3/1997 | Kohne | |
| 5,623,049 A | 4/1997 | Lobberding | |
| 5,629,178 A | 5/1997 | Demers | 435/91.2 |
| 5,631,169 A | 5/1997 | Lakowicz | |
| 5,635,347 A | 6/1997 | Link et al. | 435/6 |
| 5,641,631 A | 6/1997 | Kohne | |
| 5,643,762 A | 7/1997 | Ohshima | |
| 5,656,461 A | 8/1997 | Demers | 435/91.1 |
| 5,675,517 A | 10/1997 | Stokdijk | |
| 5,691,145 A | 11/1997 | Pitner | |
| 5,691,146 A | 11/1997 | Mayrand | |
| 5,705,346 A | 1/1998 | Okamoto | |
| 5,707,804 A | 1/1998 | Mathies | |
| 5,714,331 A | 2/1998 | Buchardt | |
| 5,723,294 A | 3/1998 | Glass | |
| 5,723,591 A | 3/1998 | Livak et al. | 536/22.1 |
| 5,736,336 A | 4/1998 | Buchardt | |
| 5,763,167 A | 6/1998 | Conrad | |
| 5,770,365 A | 6/1998 | Lane | |
| 5,773,571 A | 6/1998 | Nielsen | |
| 5,780,233 A | 7/1998 | Guo | |
| 5,786,461 A | 7/1998 | Buchardt | |
| 5,787,032 A | 7/1998 | Heller | |
| 5,800,996 A | 9/1998 | Lee | |
| 5,804,375 A | 9/1998 | Gelfand et al. | 435/6 |

(Continued)

FOREIGN PATENT DOCUMENTS

EP 0853129 A2 7/1998

(Continued)

OTHER PUBLICATIONS

Armitage, B. et al, Hairpin-forming peptide nucleic acid oligomers. Biochem. 37, 9417-9425 (1998).

(Continued)

*Primary Examiner*—Kenneth R. Horlick
(74) *Attorney, Agent, or Firm*—Timothy H. Joyce

(57) ABSTRACT

This invention is directed to methods for determining amplified nucleic acid using Linear Beacons.

16 Claims, 16 Drawing Sheets

U.S. PATENT DOCUMENTS

| | | | |
|---|---|---|---|
| 5,804,386 A | 9/1998 | Ju | |
| 5,827,660 A | 10/1998 | Singer | |
| 5,831,014 A | 11/1998 | Cook | |
| 5,846,729 A | 12/1998 | Wu | |
| 5,849,544 A | 12/1998 | Harris et al. | 435/91.2 |
| 5,866,336 A | 2/1999 | Nazarenko | |
| 5,876,930 A | 3/1999 | Livak et al. | 435/6 |
| 5,879,885 A | 3/1999 | Becker | |
| 5,888,733 A | 3/1999 | Hyldig-Nielsen et al. | 435/6 |
| 5,891,625 A | 4/1999 | Buchardt et al. | 435/6 |
| 5,912,145 A | 6/1999 | Stanley | 435/91.1 |
| 5,925,517 A | 7/1999 | Tyagi | |
| 5,972,610 A | 10/1999 | Buchardt et al. | 435/6 |
| 5,985,563 A | 11/1999 | Hyldig-Nielsen et al. | 435/6 |
| 6,020,124 A | 2/2000 | Sorenson | 435/6 |
| 6,030,787 A | 2/2000 | Livak et al. | 435/6 |
| 6,103,476 A | 8/2000 | Tyagi et al. | 435/6 |
| 6,110,676 A | 8/2000 | Coull et al. | 435/6 |
| 6,177,249 B1 | 1/2001 | Kwok et al. | 435/6 |
| 6,214,979 B1 | 4/2001 | Gelfand et al. | 536/22.1 |
| 6,355,421 B1 | 3/2002 | Coull et al. | 435/6 |
| 6,361,942 B1 | 3/2002 | Coull et al. | 435/6 |

FOREIGN PATENT DOCUMENTS

| | | |
|---|---|---|
| WO | WO93/10267 | 5/1993 |
| WO | WO93/25706 | 12/1993 |
| WO | WO94/02634 | 2/1994 |
| WO | WO94/28171 | 12/1994 |
| WO | WO95/13399 | 5/1995 |
| WO | WO97/07235 | 2/1997 |
| WO | WO97/14026 | 4/1997 |
| WO | WO97/18325 | 5/1997 |
| WO | WO97/39008 | 10/1997 |
| WO | WO97/45539 | 12/1997 |
| WO | WO97/46711 | 12/1997 |
| WO | WO97/46714 | 12/1997 |
| WO | WO98/10096 | 3/1998 |
| WO | WO98/14612 | 4/1998 |
| WO | WO98/18965 | 5/1998 |
| WO | WO98/24933 | 6/1998 |
| WO | WO98/26093 | 6/1998 |
| WO | WO98/29568 | 7/1998 |
| WO | WO98/30883 | 7/1998 |
| WO | WO98/37232 | 8/1998 |

OTHER PUBLICATIONS

Bagwell, C.B. et al, A new homogeneous assay system for specific nucleic acid sequences: poly-dA and poly-A detection. Nucleic Acids Res. 22, 2424-2425 (1994).

Blok, H.J. et al, Amplifiable hybridization probes containing a molecular switch. Molecular and Cellular Probes 11, 187-194 (1997).

Cardullo, R.A. et al, Detection of nucleic aid hybridization by nonradiative fluorescence resonance energy transfer. Proc. Natl. Acad. Sci. USA 85, 8790-8794 (1988).

Carmel, A. et al, Intramolecularly-quenched fluorescent peptides as fluorogenic substrates of leucine aminopeptidase and inhibitors of clostridial aminopeptidase. Eur. J. Biochem. 73, 617-625 (1977).

Chen, X. et al, A homogeneous, ligase-mediated DNA diagnostic test. Genome Res. 8, 549-556 (1998).

Clegg, R.M., Fluorescence Resonance Energy Transfer and Nucleic Acids. Methods in Enzymology 211, 353-388 (1992).

Corey, D.R. 48000-fold Acceleration of Hybridization by Chemically Modified Oligonucleotides. J. Am. Chem. Soc. 117, 9373-9374 (1995).

Diederichsen, U. et al, Self-Pairing PNA with alternating alanyl-homoalanyl backbone. Tett. Lett. 37, 475-478 (1996).

Dueholm, K.L. et al, Chemistry, properties and applications of PNA (Peptide Nucleic Acid). New J. Chem. 21, 19-31 (1977).

Egholm, M. et al, PNA hybidizes to complementary oligonucleotides obeying the Watson-Crick hydrogen-bonding rules. Nature 365, 566-568 (1993).

Ferguson, J.A. et al, A fiber-optic DNA biosensor microarray for the analysis of gene expression. Nature Biotech. 14, 1681-1684 (1996).

Fujii, M. et al, Nucleic acid analog peptide (NAAP)2, syntheses and properties of novel DNA analog peptides containing nucleobase linked β-aminoalanine. Bioorg. & Med. Chem. Lett. 7, 637-640 (Mar. 1997).

Guo, Z. et al, Direct fluorescence analysis of genetic polymorphisms by hybridization with oligonucleotide arrays on glass supports. Nucleic Acids Res. 22, 5456-5465 (1994).

Guo, Z. et al, Enhanced discrimination of single nucleotide polymorphisms by artificial mismatch hybridization. Nature Bi tech. 15, 331-335 (1997).

Haasnoot, C.A.G. et al, Structure, kinetics and thermodynamics of DNA hairpin fragments in solution. J. Bi m lecular Structure and Dynamics 1, 115-129 (1983).

Holland, P.M. et al, Detection of specific polymerase chain reaction product by utilizing the 5'→3' exonuclease activity of *Thermus aquaticus* DNA polymerase. Proc. Natl. Acad. Sci. USA 88, 7276-7280 (1991).

Hung, S.-C. et al, Comparison of fluorescence energy transfer primers with different donor-acceptor dye combinations. Analy. Bi chem. 255, 32-38 (1998).

Hyldig-Nielsen, J.J. et al, Advances in the use of PNA probes for diagnostic testing. IBC's 3rd Annual Internati nal Symp sium n Diagnosti Gene Detecti n and Quantification Techn l gies f r Infectious Agents and Human Genetic Diseases. Feb. 25-27, 1998, Lake Tahoe, NV.

Hyrup, B. et al, Peptide Nucleic Acids (PNA): Synthesis, Properties and Potential Applications. Bioorg. & Med. Chem. 4, 5-23 (1996).

Iyer, M. et al, Accelerated Hybridization of Oligonucleotides to Duplex DNA. The J. of Biol. Chem. 270, 14712-14717 (1995).

Jordan, S. et al, New hetero-oligomeric peptide nucleic acids with improved binding properties to complementary DNA. Bioorg. & Med. Chem. Lett. 7, 687-690 (1997).

Jordan, S. et al, Synthesis of new building blocks for peptide nucleic acids containing monomers with variations in the backbone. Bioorg. & Med. Chem. Lett. 7, 681-686 (1997).

Ju, J. et al, Fluorescence energy transfer dye-labeled primers for DNA sequencing and analysis. Proc. Natl. Acad. Sci. USA 92, 4347-4351 (1995).

Kostrikis, L.G. et al, Spectral genotyping of human alleles. Science 279, 1228-1229 (1998).

Krotz, A.H. et al, Synthesis of "Retro-inverso" Peptide Nucleic Acids: 2. Oligomerization and stability. Tett. Lett. 36, 6941-6944 (1995).

Lagriffoul, P.-H. et al, The synthesis, co-oligomerization and hybridization of a thymine-thymine heterodimer containing PNA. Bioorg. & Med. Chem. Lett. 4, 1081-1082 (1994).

Larin, Z. et al, Fluorescence in situ hybridisation of multiple probes on a single microscope slide. Nucleic Acids Res. 22, 3689-3692 (1994).

Lee, L.G. et al, Allelic discrimination by nick-translation PCR with fluorogenic probes. Nucleic Acids Res. 21, 3761-3766 (1993).

Leone, G. et al, Molecular beacon probes combined with amplification by NASBA enable homogeneous, real-time detection of RNA. Nucl. Acids Res. 26, 2150-2155 (1998).

Lester, A. et al, PNA array technology. Presented at Biochip Technologies Conference in Annapolis (Oct. 1997).

Lewis, R. Oncor and Chiron Offer Improvements & Alternatives in Gene Amplification. Gen. Eng. News, 17, 3 & 36 (Jun. 1, 1997).

Livak, K.J. et al, Oligonucleotides with Fluorescent Dyes at Opposite Ends Provide a Quenched Probe System useful for Detecting PCR Product and Nucleic Acid Hybridization. PCR Methods and Applic. 4, 357-362 (1995).

Lowe, G. et al, Amino acids bearing nucleobases for the synthesis of novel peptide nucleic acids. J. Chem. Soc., Perkin Trans. 1, 4, 539-546 (1997).

Lowe, G. et al, Dipeptides bearing nucleobases for the synthesis of novel peptide nucleic acids. J. Chem. Soc., Perkin Trans. 1, 4 547-554 (1997).

Lowe, G. et al, Solid-phase synthesis of novel peptide nucleic acids. J. Chem. Soc., Perkin Trans. 1, 4, 555-560 (1997).

Lutz, M.J. et al, Recognition of Uncharged Polyamide-Linked Nucleic Acid Analogs by DNA Polymerases and Reverse Transcriptases. J. Am. Chem. Soc. 119, 3177-3178 (1997).

Lyamichev, V. et al, Structure-Specific Endonucleolytic Cleavage of Nucleic Acids by Eubacterial DNA Polymerases. Science 260, 778-783 (1993).

Matray, T.J. et al, Selective and stable DNA base pairing without hydrogen bonds. J. Am. Chem. Soc. 120, 6191-6192 (1998).

Meldal, M. et al, Anthranilamide and Nitrotyrosine as a Donor-Acceptor Pair in Internally Quenched Fluorescent Substrates for Endopeptidases: Multicolumn Peptide Synthesis of Enzyme Substrates for Subtilisin Carlsberg and Pepsin. Anal. Biochem. 195, 141-147 (1991).

Mergny, J.-L. et al, Fluorescence Energy Transfer between Two Triple Helix-Forming Oligonucleotides Bound to Duplex DNA. Biochem. 33, 15321-15328 (1994).

Nazarenko, I.A. et al, A closed tube format for amplification and detection of DNA based on energy transfer. Nucleic Acids Res. 25, 2516-2521 (1997).

Nazarenko, I.A., A Closed-Tube Format for Amplification and Detection of Nucleic Acids Based on Energy Transfer. Fifth Annual Advances in Nucleic Acid Amplification and Detecti n, San Francisco, CA (Jun. 16-17, 1997).

Ng, M. et al, A Fluorescent Oligopeptide Energy Transfer Assay with Broad Applications for Neutral Proteases. Anal. Bi chem. 183, 50-56 (1989).

Nielsen, P.E. et al, Peptide Nucleic Acid (PNA). A DNA Mimic with a Peptide Backbone. Bioc n. Chem. 5, 3-7 (1994).

Nielsen, P.E. et al, Peptide nucleic acids (PNAs): Potential Antisense and Anti-gene Agents. Anti-Cancer Drug Design 8, 53-63 (1993).

Oncor, Inc. Press Release Apr. 14, 1997.

Paris, P.L. et al, Probing DNA sequences in solution with a monomer-excimer fluorescence color change, Nucl. Acids Res. 26, 3789-3793 (1998).

Parkhurst, K.M. et al, Kinetic Studies by Fluorescence Resonance Energy Transfer Employing a Double-Labeled Oligonucleotide: Hybridization to the Oligonucleotide Complement and to Single-Stranded DNA. Biochem. 34, 285-292 (1995).

PerSeptive Promotional Literature. Bio ConSepts: PNA and its use as an analytical molucular biology tool. 1996.

PerSeptive Promotional Literature. Peptide Nucleic Acids (PNA): Expanding the role of synthetic DNA analogs. 1995.

PerSeptive Promotional Literature. Peptide Nucleic Acids (PNA): Probing the improbable. 1997.

PerSeptive Promotional Literature. PNA Oligomers as hybridization probes. 1995.

Petersen, K.H. et al, Synthesis and oligomerization of $N^\delta$-Boc-$N^\alpha$-(thymin-1-ylacetyl)ornithine. Bioorg. & Med. Chem. Lett. 6, 793-796 (1996).

Piatek, A.S. et al, Molecular beacon sequence analysis for detecting drug resistance in *Mycobacterium tuberculosis*. Nature Biotech. 16, 359-363 (1998).

Promisel Cooper, J. et al, Analysis of Fluoroescence Energy Transfer in Duplex and Branched DNA Molecules. Biochem. 29, 9261-9268 (1990).

Ratilainen, T. et al, Hybridization of peptide nucleic acid. Biochem. 37, 12331-12342 (1998).

Rye, H.S. et al, Stable fluorescent complexes of double-stranded DNA with bis-intercalating asymmetric cyanine dyes: properties and applications. Nucleic Acids Res. 20, 2803-2812 (1992).

Scheffler, I.E. et al, Helix formation by dAT oligomers. I. Hairpin and straight-chain helices. J. M l. Biol. 36, 291-304 (1968).

Selvin, P.R., Fluorescence Resonance Energy Transfer. Methods in Enzymology 246, 300-334 (1995).

Singh, D. et al, Oligonucleotides, part 5+: synthesis and fluorescence studies of DNA oligomers $d(AT)_5$ containing adenines covalently linked at C-8 with dansyl fluorophore. Nucleic Acids Res. 18, 3339-3345 (1990).

Sixou, S. et al, Intracellular oligonucleotide hybridization detected by fluorescence resonance energy transfer (FRET). Nucleic Acids Res. 22, 662-668 (1994).

Sosnowski, R.G. et al, Rapid determination of single base mismatch mutations in DNA hybrids by direct electric field control. Proc. Natl. Acad. Sci USA 94, 1119-1123 (1997).

Thisted, M. et al, Detection of immunoglobulin kappa light chain mRNA in paraffin sections by in situ hybridization using peptide nucleic acid probes. Cell Vision 3, 358-363 (1996).

Thornton, N.B. et al, Chromophore-quencher probes for DNA. New J. Chem. 20, 791-800 (1996).

Tomac, S. et al, Ionic effects on the stability and conformation of Peptide Nucleic Acid Complexes. J. Am. Chem. Soc. 118, 5544-5552 (1996).

Tyagi, S. et al, Molecular Beacons: Probes that Fluoresce upon Hybridization. Nature Biotech. 14, 303-308 (1996).

Tygai, S. et al, Multicolor molecular beacons for allele discrimination. Nature Biotech. 16, 49-53 (1998).

van Gemen, B. et al, Qualitative and quantitative detection of HIV-1 RNA by nucleic acid sequence-based amplification. AIDS 7, S107-S110 (1993).

Vaughan, W.M. et al, Oxygen quenching of pyrenebutyric acid fluorescence in water. A dynamic probe of the microenvironment. Bi ch m. 9, 464-473 (1970).

Wang, G.T. et al, Design and Synthesis of New Fluorogenic HIV Protease Substrates Based on Resonance Energy Transfer. Tett. Lett. 31, 6493-6496 (1990).

Weber, P.J.A. et al, A fast and inexpensive method for N-terminal fluoresein-labeling of peptides. Bi org. & Med. Chem. Lett. 8, 597-600 (1998).

Weiler, J. et al, Hybridisation based DNA screening on peptide nucleic acid (PNA) oligomer arrays. Nucl Acids Res. 25, 2792-2799 (1997).

Wittung, P. et al, Induced Chirality in PNA-DNA Duplexes. J. Am. Chem. Soc. 117, 10167-10173 (1995).

Yamamoto, N. et al, A rapid detection of PCR amplification product using a new fluorescent intercalator; the pyrylium dye, P2. Nucleic Acids Res. 23, 1445-1446 (1995).

Yang, M. et al, A DNA assay based on fluorescence resonance energy transfer and DNA triplex formation. Analy. Biochem. 259, 272-274 (1998).

Yaron, A. et al, Intramolecularly quenched fluorogenic substrates for hydrolytic enzymes. Analy. Biochem. 95, 228-235 (1979).

Zimmerman, M. et al, A New Fluorogenic Substrate for Chymotrypsin. Anal. Biochem. 70, 258-62 (1976).

Ratilainen, T. et al, Hybridization of Peptide Nucleic Acid. Biochem. 37, 12331-12342 (1998).

Wang, J. et al, Peptide nucleic acid probes for sequence-specific DNA biosensors. J. Amer. Chem. Soc. 118, 7667-7670 (1996).

Corey, D.R., et al. Peptide Nucleic Acids: expanding the scope of nucleic acid recognition. Tibtech. 15, 224-229 (1997).

Nielsen, P.E., Peptide Nucleic Acid. A Molecule with Two Identities. Acc. Chem. Rec. 32, 624-630 (1999).

Ortiz, E., et al. PNA molecular beacons for rapid detection of PCR amplicons. Molecular and Cellular Probes. 12, 219-226 (1998).

Ratilainen, T., et al. Hybridization of Peptide Nucleic Acid. Biochemistry. 37, 12331-12342 (1998).

Parkhurst et al., Donor-Acceptor Distance Distributions In A Double-Labeled Fluroescent Oligonucleotide Bost As A Single Strand And In Duplexes, Biochemistry, 34, 293-300 (1995).

Agrawal, S. et al, Site specific functionalization of oligonucleotides for attaching two different reporter groups. Nucleic Acids Research, 18, 5419-5423, (1990).

Demers, D. et al, Enhanced PCR amplification of VNTR locus D1S80 using peptide nucleic acid (PNA). Nucleic Acids Research, 15, 3050-3055, (1995).

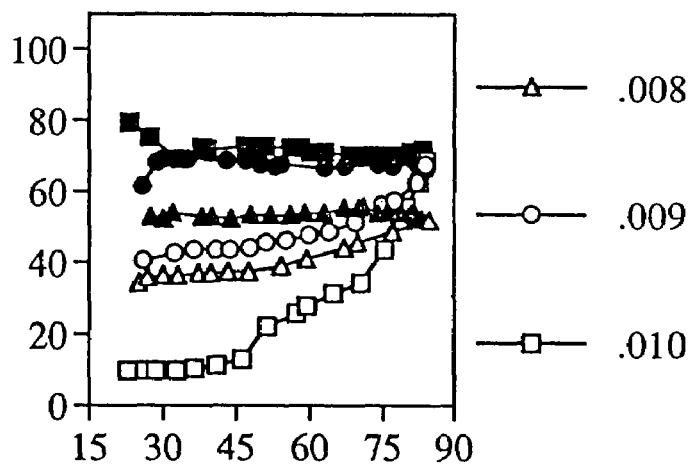
Figure 1B1
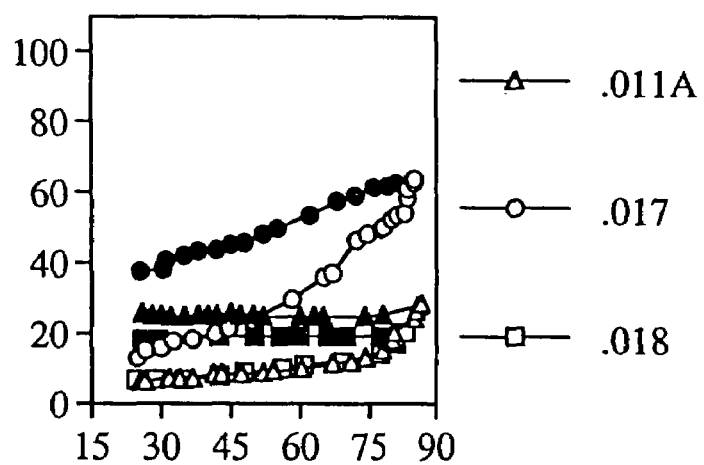
Figure 1B2
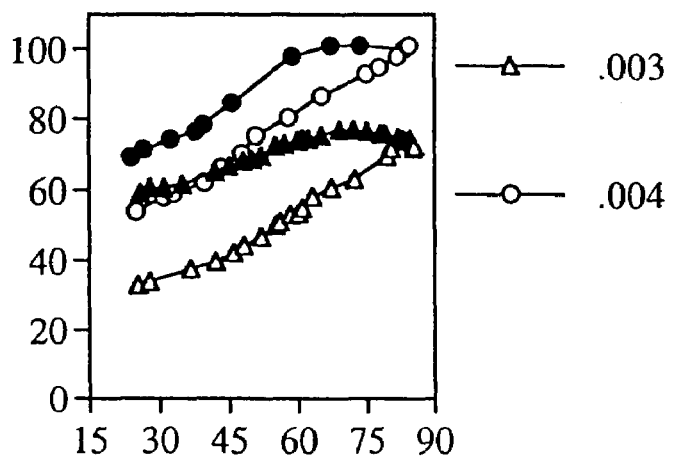
Figure 1B3

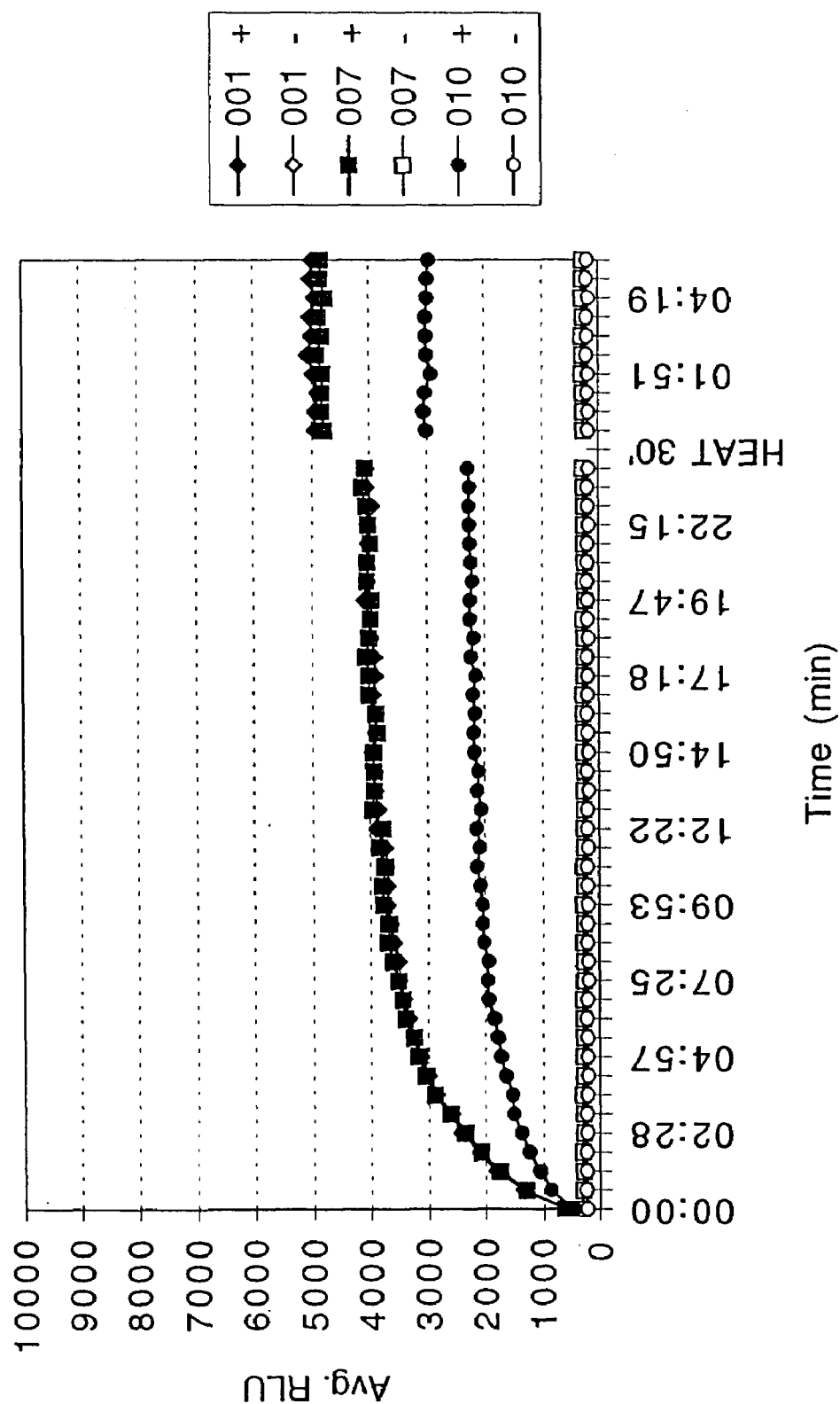
Figure 2A1

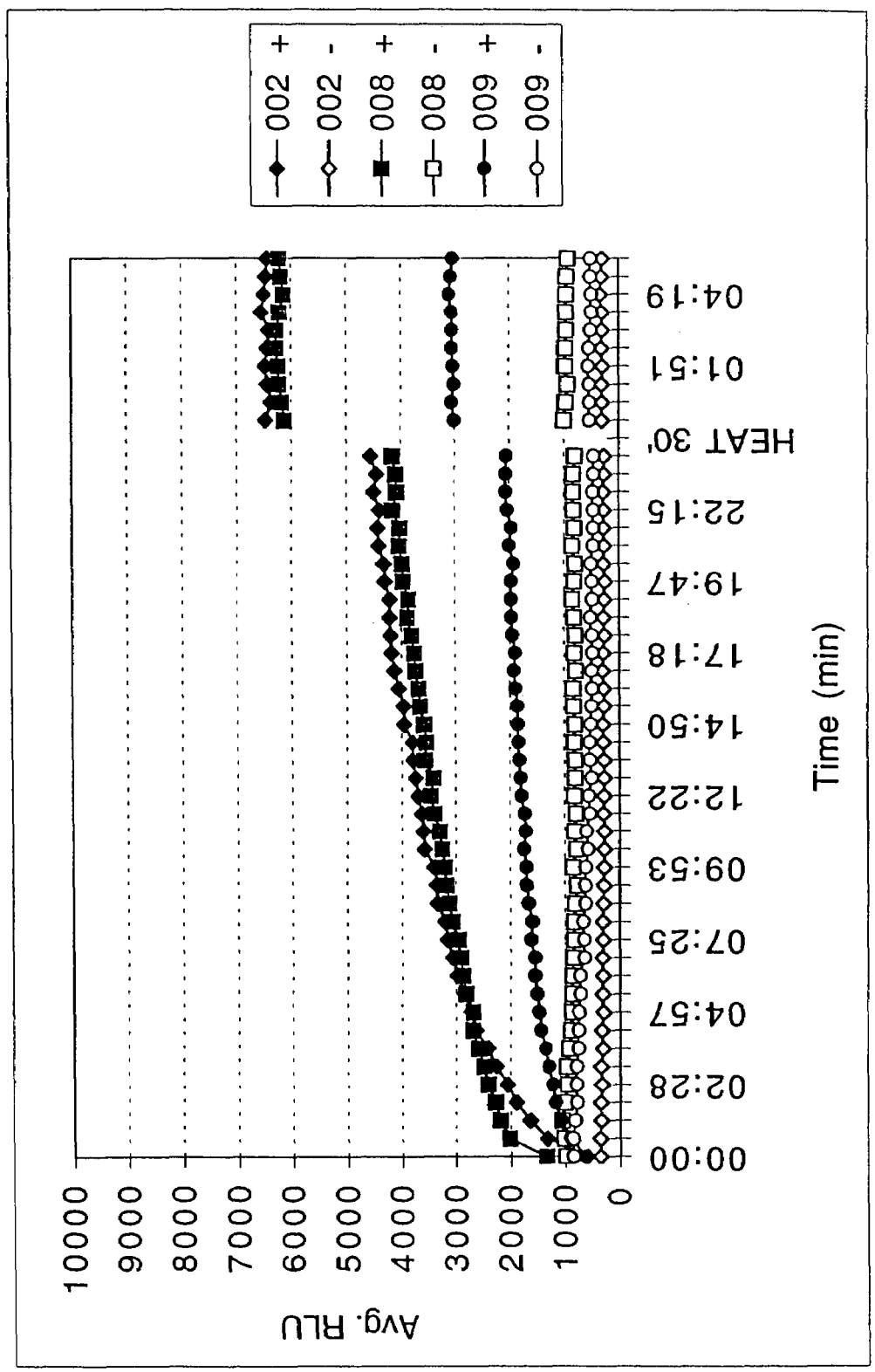
Figure 2A2

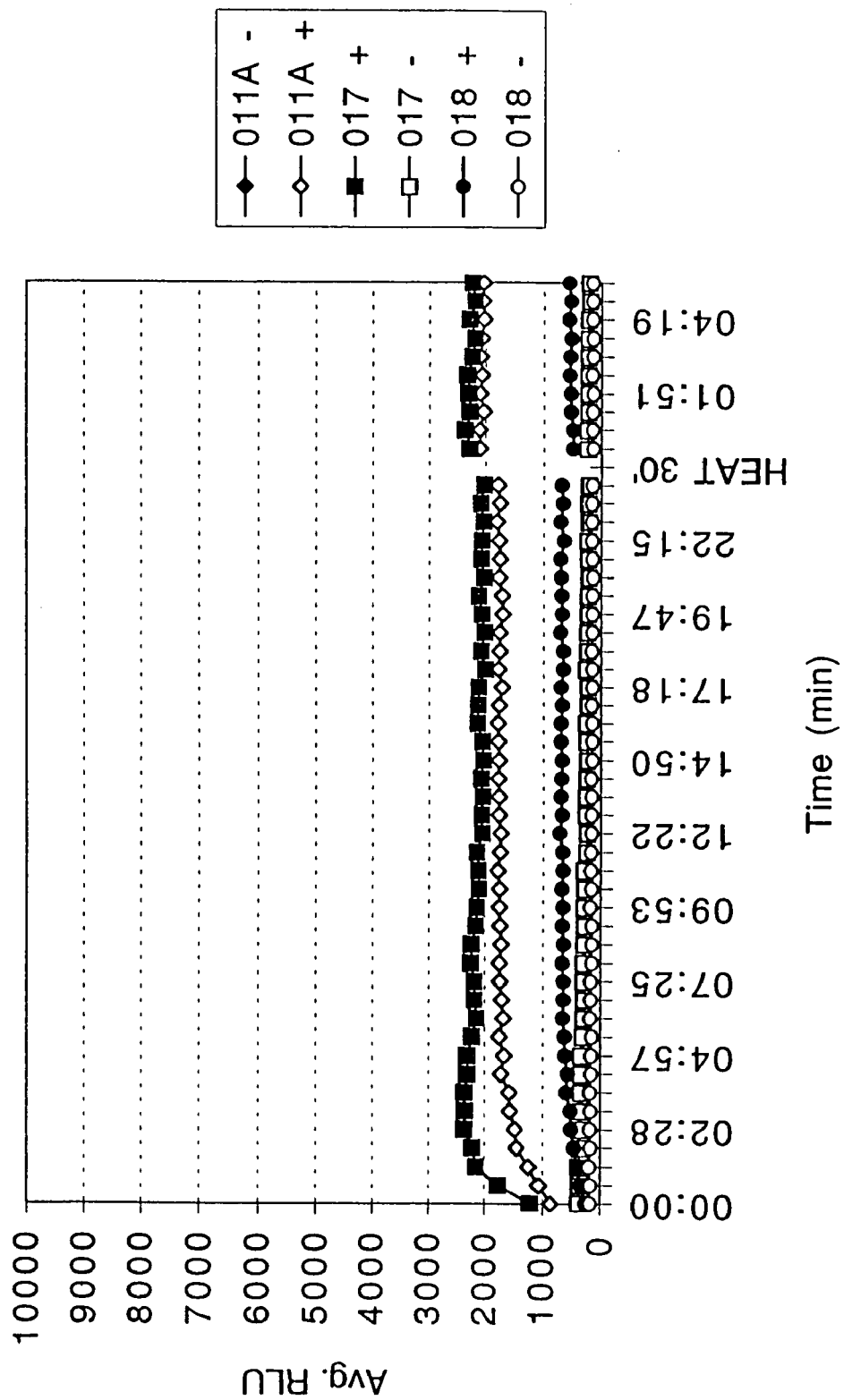
Figure 2A3

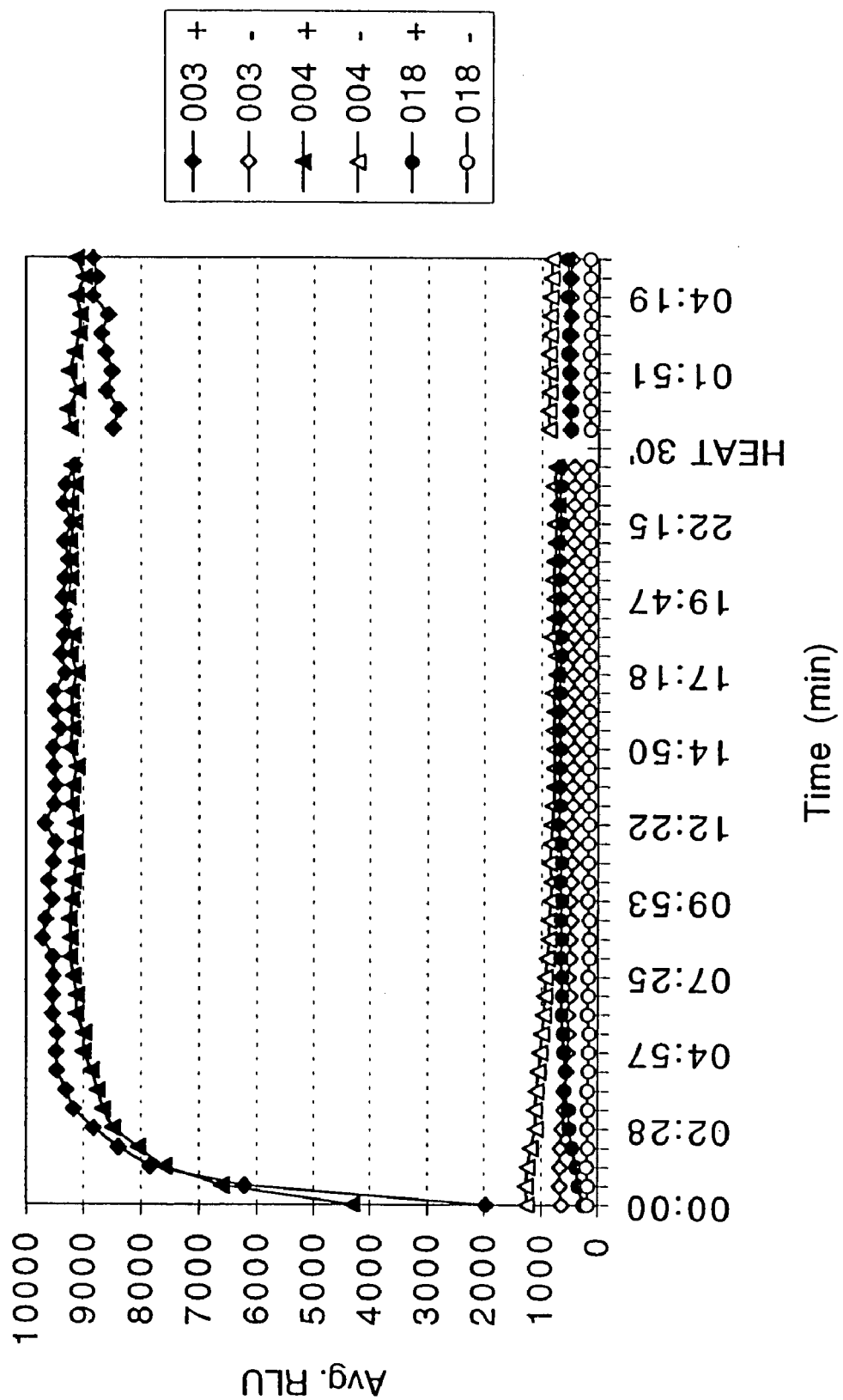

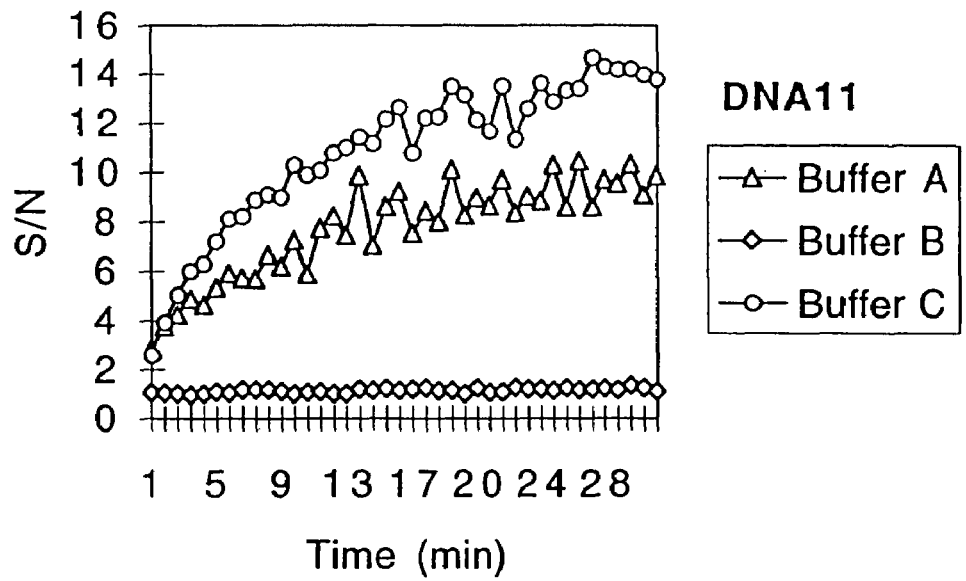
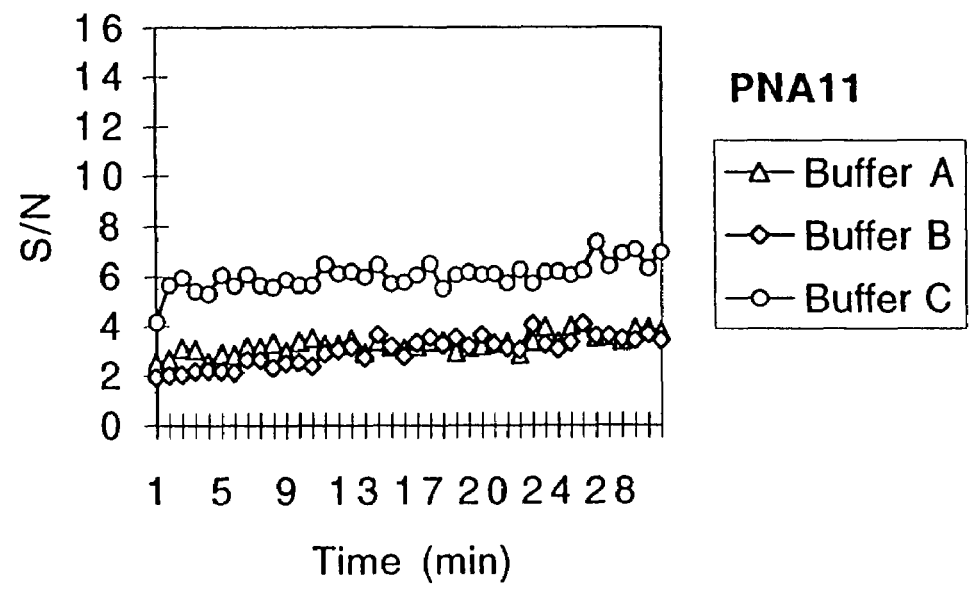

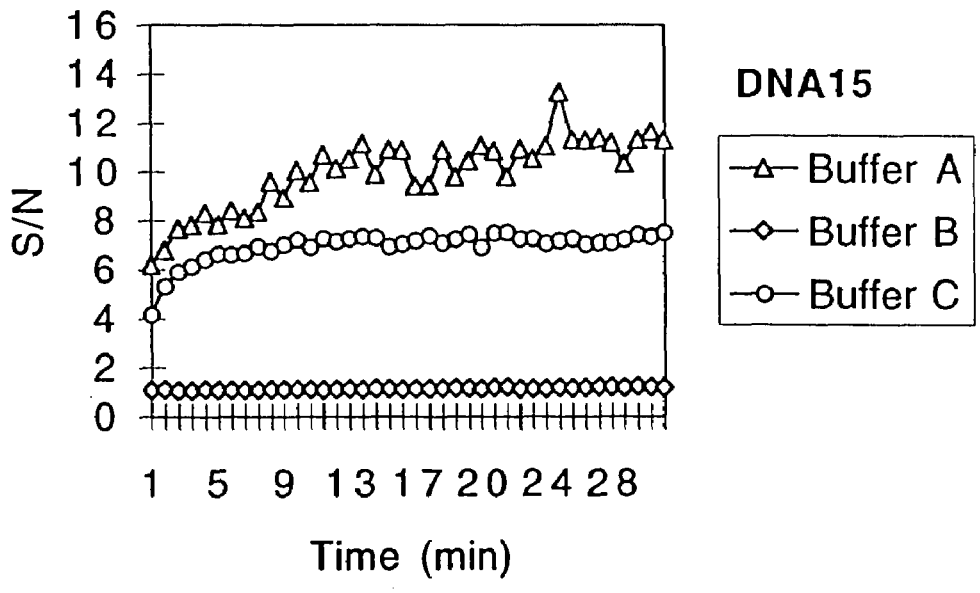
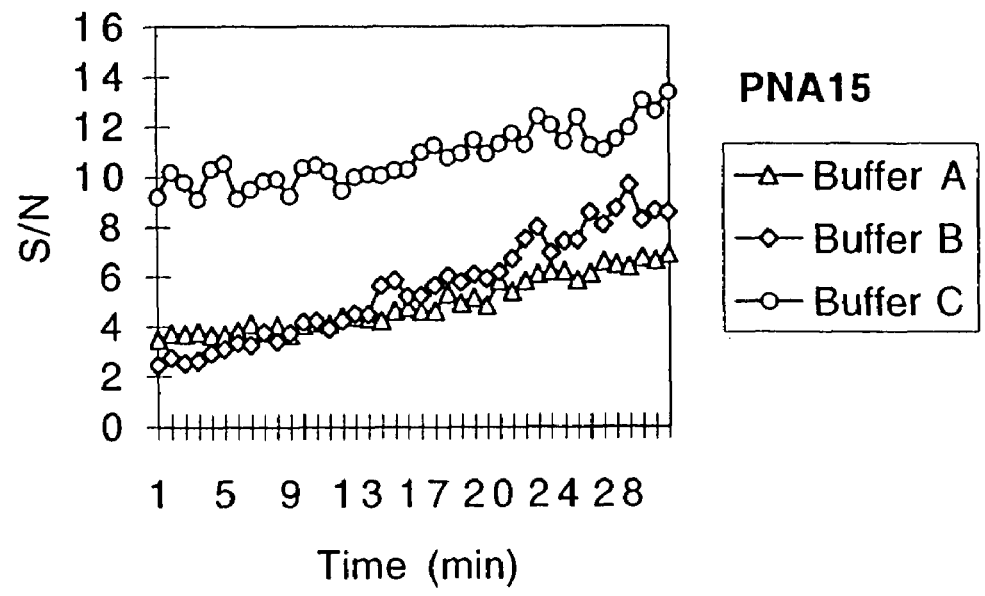

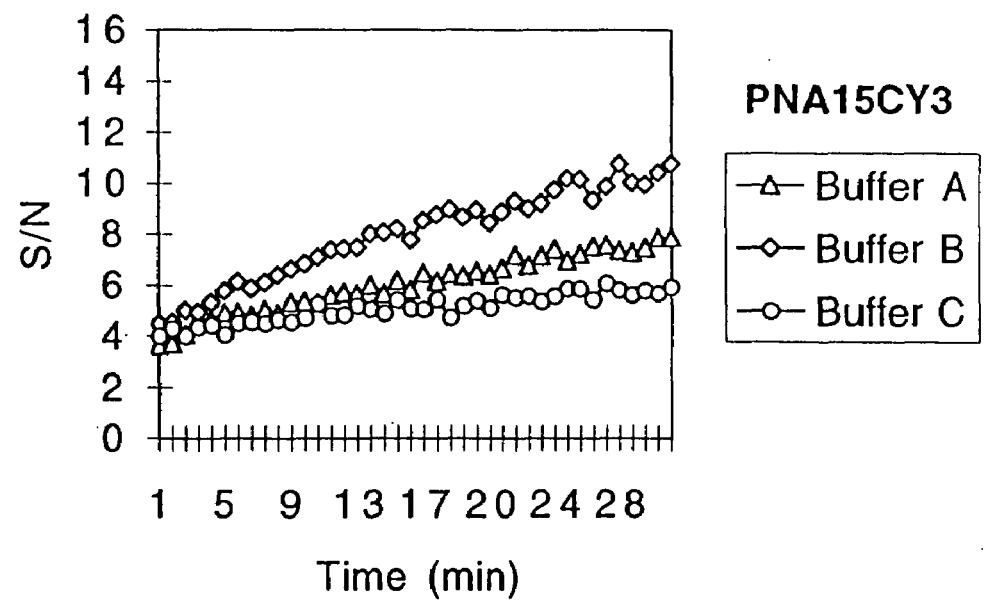

Tubes 3 and 4 (l to r) after 45 cycles of PCR.

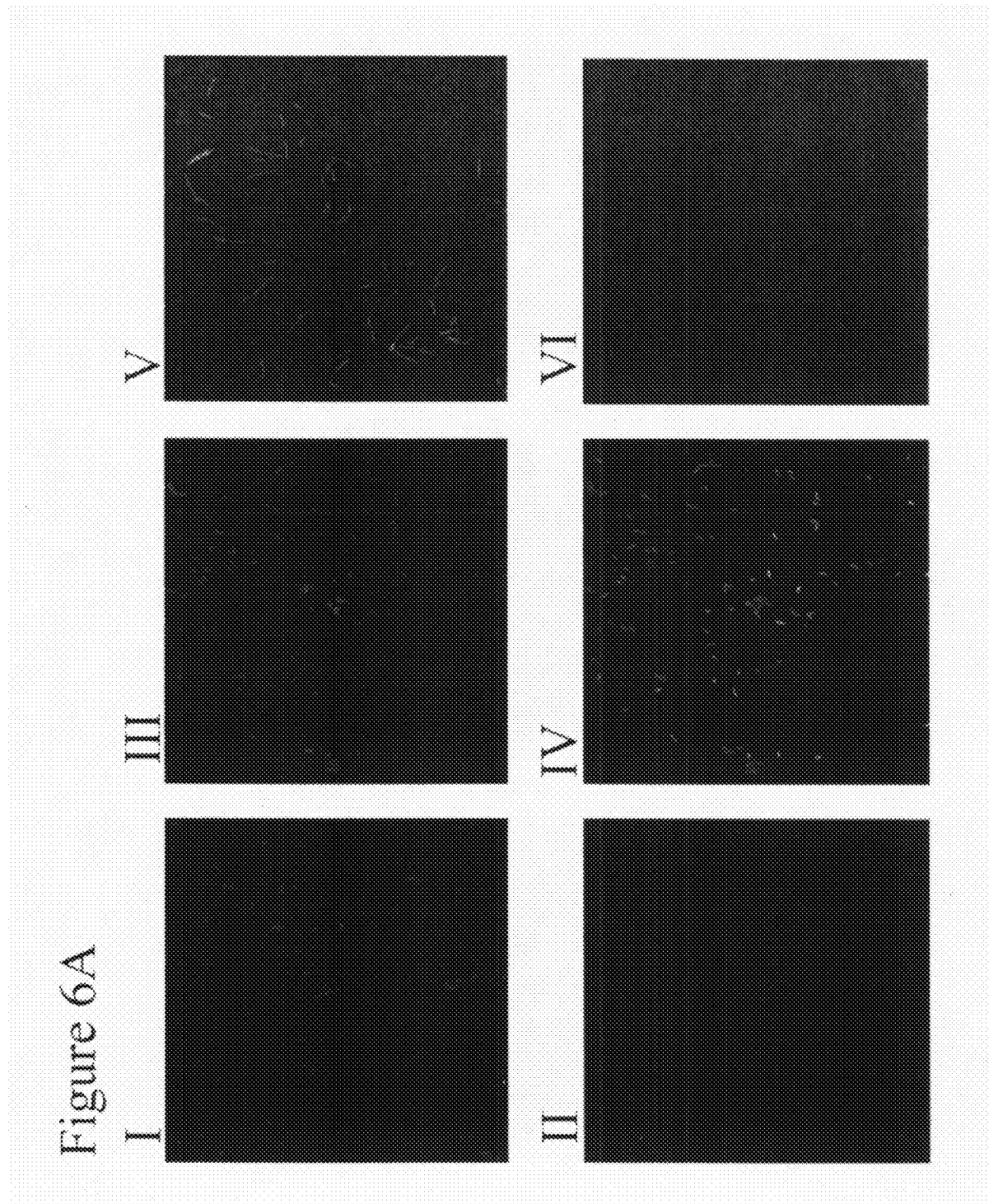

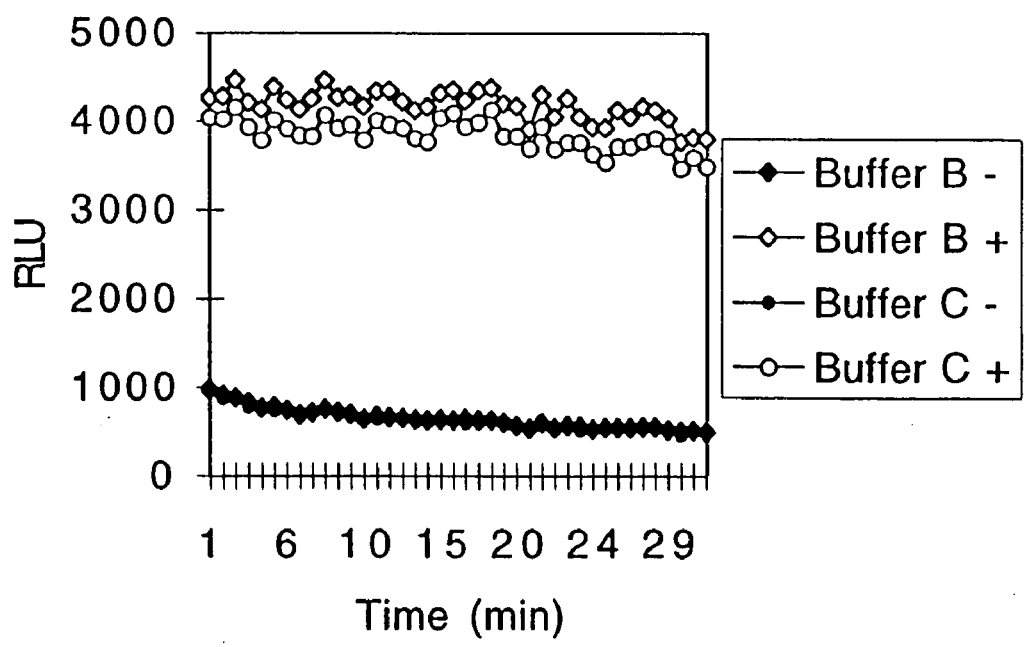
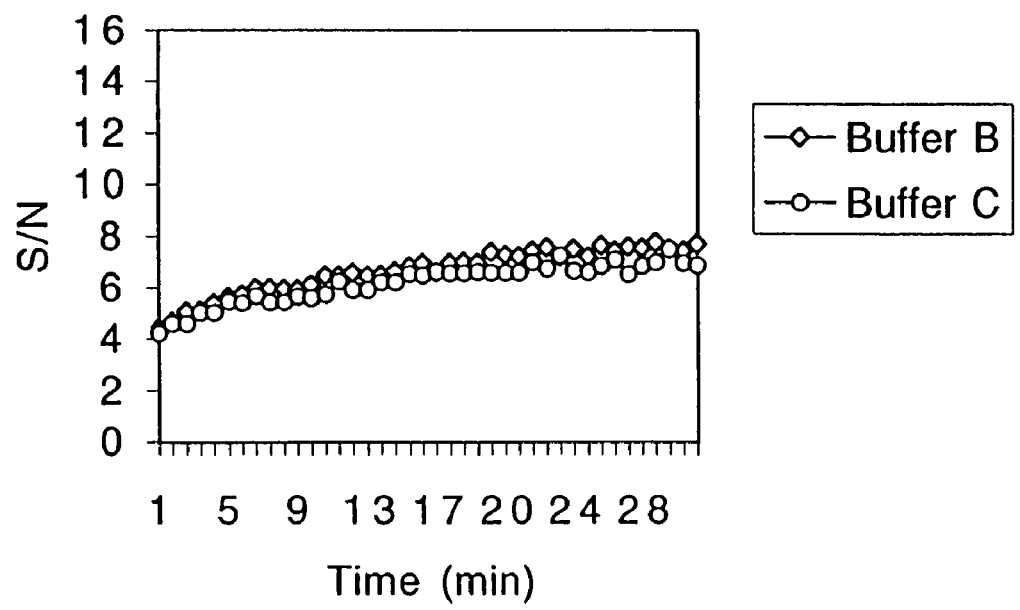

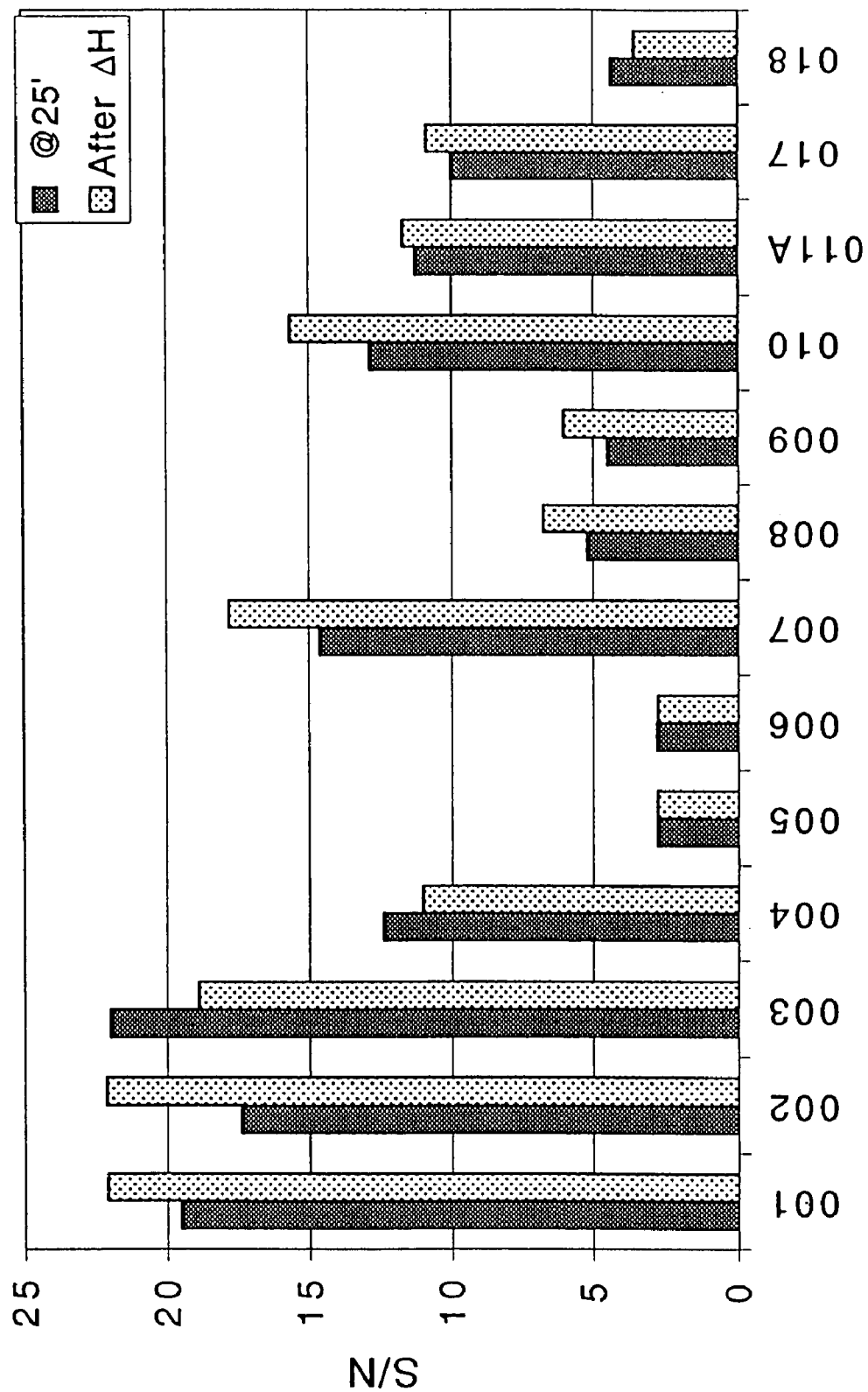

SEQUENCE LISTING

```
<160> NUMBER OF SEQ ID NOS: 10

<210> SEQ ID NO 1
<211> LENGTH: 31
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Biotin
<220> FEATURE:
<223> OTHER INFORMATION: Description of Artificial Sequence: SYNTHETIC
      PROBE OR TARGET

<400> SEQUENCE: 1
gtggtagttg gagctggtgg cgtaggcaag a                                    31

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: SYNTHETIC
      PROBE OR TARGET

<400> SEQUENCE: 2
ggtagtgtct ggtgatgctg gaggcaa                                         27

<210> SEQ ID NO 3
<211> LENGTH: 11
<212> TYPE: DNA
<213> ORGANISM: Artificial Sequence
<220> FEATURE:
```

-continued

```
<221> NAME/KEY: misc_feature
<222> LOCATION: (1)
<223> OTHER INFORMATION: 5'Fluorescein
<220> FEATURE:
<221> NAME/KEY: misc_feature
<222> LOCATION: (11)
<223> OTHER INFORMATION: 3' Dabcyl
<220> FEATURE:
<223> OTHER INFORMATION: Description of Artificial Sequence: SYNTHETIC
      PROBE OR TARGET

<400> SEQUENCE: 3
gccaccagct c                                                           11

<210> SEQ ID NO 4
<211> LENGTH: 13
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Fluorescein
<220> FEATURE:
<221> NAME/KEY: misc_feature
<222> LOCATION: (13)
<223> OTHER INFORMATION: 3' Dabcyl
<220> FEATURE:
<223> OTHER INFORMATION: Description of Artificial Sequence: SYNTHETIC
      PROBE OR TARGET

<400> SEQUENCE: 4
cgccaccagc tcc                                                         13

<210> SEQ ID NO 5
<211> LENGTH: 15
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Fluorescein
<220> FEATURE:
<221> NAME/KEY: misc_feature
<222> LOCATION: (15)
<223> OTHER INFORMATION: 3' Dabcyl
<220> FEATURE:
<223> OTHER INFORMATION: Description of Artificial Sequence: SYNTHETIC
      PROBE OR TARGET

<400> SEQUENCE: 5
acgccaccag ctcca                                                       15

<210> SEQ ID NO 6
<211> LENGTH: 17
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Fluorescein
<220> FEATURE:
<221> NAME/KEY: misc_feature
<222> LOCATION: (17)
<223> OTHER INFORMATION: 3' Dabcyl
<220> FEATURE:
<223> OTHER INFORMATION: Description of Artificial Sequence: SYNTHETIC
      PROBE OR TARGET

<400> SEQUENCE: 6
tacgccacca gctccaa                                                     17
```

-continued

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      PROBE OR TARGET

<400> SEQUENCE: 7
atgactgaat ataaacttgt                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      PROBE OR TARGET

<400> SEQUENCE: 8
ctctattgtt ggatcatatt                                                    20

<210> SEQ ID NO 9
<211> LENGTH: 111
<212> TYPE: DNA
<213> ORGANISM: Homo sapiens
<220> FEATURE:
<223> OTHER INFORMATION: Description of Artificial Sequence: SYNTHETIC
      PROBE OR TARGET

<400> SEQUENCE: 9
gagataacaa cctagtataa gcaggtgttt tactaagact taatcgactt agcagttccg        60
tgagaacgga tgcggtgttc gaggttgatg gtgttcaaat ataagtcagt a                111

<210> SEQ ID NO 10
<211> LENGTH: 111
<212> TYPE: DNA
<213> ORGANISM: Homo sapiens
<220> FEATURE:
<223> OTHER INFORMATION: Description of Artificial Sequence: SYNTHETIC
      PROBE OR TARGET

<400> SEQUENCE: 10
ctctattgtt ggatcatatt cgtccacaaa atgattctga attagctgta tcgtcaaggc        60
actcttgcct acgccacaag ctccaactac cacaagttta tattcagtca t                111
```

DETECTION OF NUCLEIC ACID USING LINEAR BEACONS

CROSS REFERENCE TO RELATED APPLICATIONS

This application is a divisional application of U.S. Ser. No. 09/950,459 (herein incorporated by reference) filed on Sep. 10, 2001, now U.S. Pat. No. 6,649,349, issued Nov. 18, 2003, which is a divisional of U.S. Ser. No. 09/179,162 (herein incorporated by reference) filed on Oct. 26, 1998, now U.S. Pat. No. 6,485,901, issued Nov. 26, 2002, which application claims the benefit of U.S. Provisional Application No. 60/063,283 (herein incorporated by reference) filed on Oct. 27, 1997.

BACKGROUND OF THE INVENTION

1. Field of the Invention

This invention is related to the field of probe-based nucleic acid sequence detection, analysis and quantitation. More specifically, this invention relates to novel methods, kits and compositions pertaining to Linear Beacons.

2. Description of the Related Art

Quenching of fluorescence signal can occur by either Fluorescence Resonance Energy Transfer "FRET" (also known as non-radiative energy transfer: See: Yaron et al., *Analytical Biochemistry* 95: 228-235 (1979) at p. 232, col. 1, lns. 32-39) or by non-FRET interactions (also known as radiationless energy transfer; See: Yaron et al., *Analytical Biochemistry* 95 at p. 229, col. 2, lns. 7-13). The critical distinguishing factor between FRET and non-FRET quenching is that non-FRET quenching requires short range interaction by "collision" or "contact" and therefore requires no spectral overlap between the moieties of the donor and acceptor pair (See: Yaron et al., *Analytical Biochemistry* 95 at p. 229, col. 1, lns. 22-42). Conversely, FRET quenching requires spectral overlap between the donor and acceptor moieties and the efficiency of quenching is directly proportional to the distance between the donor and acceptor moieties of the FRET pair (See: Yaron et al., *Analytical Biochemistry* 95 at p. 232, col. 1, ln. 46 to col. 2, ln. 29). Extensive reviews of the FRET phenomenon are described in Clegg, R. M., *Methods Enzymol.*, 221: 353-388 (1992) and Selvin, P. R., *Methods Enzymol.*, 246: 300-334 (1995). Yaron et al. also suggested that the principles described therein might be applied to the hydrolysis of oligonucleotides (See: Yaron et al., *Analytical Biochemistry* 95 at p. 234, col. 2, lns. 14-18).

The FRET phenomenon has been utilized for the direct detection of nucleic acid target sequences without the requirement that labeled nucleic acid hybridization probes or primers be separated from the hybridization complex prior to detection (See: Livak et al. U.S. Pat. No. 5,538,848). One method utilizing FRET to analyze Polymerase Chain Reaction (PCR) amplified nucleic acid in a closed tube format is commercially available from Perkin Elmer. The TaqMan™ assay utilizes a nucleic acid hybridization probe which is labeled with a fluorescent reporter and a quencher moiety in a configuration which results in quenching of fluorescence in the intact probe. During the PCR amplification, the probe sequence specifically hybridizes to the amplified nucleic acid. When hybridized, the exonuclease activity of the Taq polymerase degrades the probe thereby eliminating the intramolecular quenching maintained by the intact probe. Because the probe is designed to hybridize specifically to the amplified nucleic acid, the increase in fluorescence intensity of the sample, caused by enzymatic degradation of the probe, can be correlated with the activity of the amplification process.

Nonetheless, this method preferably requires that each of the fluorophore and quencher moieties be located on the 3' and 5' termini of the probe so that the optimal signal to noise ratio is achieved (See: Nazarenko et al., *Nucl. Acids Res.* 25: 2516-2521 (1997) at p. 2516, col. 2, lns. 27-35). However, this orientation necessarily results in less than optimal fluorescence quenching because the fluorophore and quencher moieties are separated in space and the transfer of energy is most efficient when they are close. Consequently, the background emission from unhybridized probe can be quite high in the TaqMan™ assay (See: Nazarenko et al., *Nucl. Acids Res.* 25: at p. 2516, col. 2, lns. 36-40).

The nucleic acid Molecular Beacon is another construct which utilizes the FRET phenomenon to detect target nucleic acid sequences (See: Tyagi et al. *Nature Biotechnology*, 14: 303-308 (1996). A nucleic acid Molecular Beacon comprises a probing sequence embedded within two complementary arm sequences (See: Tyagi et al, *Nature Biotechnology*, 14: at p. 303, col. 1, lns. 22-30). To each termini of the probing sequence is attached one of either a fluorophore or quencher moiety. In the absence of the nucleic acid target, the arm sequences anneal to each other to thereby form a loop and hairpin stem structure which brings the fluorophore and quencher together (See: Tyagi et al., *Nature Biotechnology*, 14: at p. 304, col. 2, lns. 14-25). When contacted with target nucleic acid, the complementary probing sequence and target sequence will hybridize. Because the hairpin stem cannot coexist with the rigid double helix that is formed upon hybridization, the resulting conformational change forces the arm sequences apart and causes the fluorophore and quencher to be separated (See: Tyagi et al. *Nature Biotechnology*, 14: at p. 303, col. 2, lns. 1-17). When the fluorophore and quencher are separated, energy of the donor fluorophore does not transfer to the acceptor moiety and the fluorescent signal is then detectable. Since unhybridized "Molecular Beacons" are non-fluorescent, it is not necessary that any excess probe be removed from an assay. Consequently, Tyagi et al. state that Molecular Beacons can be used for the detection of target nucleic acids in a homogeneous assay and in living cells. (See: Tyagi et al., *Nature Biotechnology*, 14: at p. 303, col. 2; lns. 15-77).

The arm sequences of the disclosed nucleic acid Molecular Beacon constructs are unrelated to the probing sequence (See: Tyagi et al., *Nature Biotechnology*, 14: at p. 303, col. 1; ln. 30). Because the Tyagi et al. Molecular Beacons comprise nucleic acid molecules, proper stem formation and stability is dependent upon the length of the stem, the G:C content of the arm sequences, the concentration of salt in which it is dissolved and the presence or absence of magnesium in which the probe is dissolved (See: Tyagi et al., *Nature Biotechnology*, 14: at p. 305, col. 1; lns. 1-16). Furthermore, the Tyagi et al. nucleic acid Molecular Beacons are susceptible to degradation by endonucleases and exonucleases.

Upon probe degradation, background fluorescent signal will increase since the donor and acceptor moieties are no longer held in close proximity. Therefore, assays utilizing enzymes known to have nuclease activity, will exhibit a continuous increase in background fluorescence as the nucleic acid Molecular Beacon is degraded (See: FIG. 7 in Tyagi et al: the data associated with (○) and (□) demonstrates that the fluorescent background, presumably caused by probe degradation, increases with each amplification cycle.) Additionally, Molecular Beacons will also, at least partially, be degraded in living cells because cells contain active nuclease activity.

The constructs described by Tyagi et al. are more broadly described in WO95/13399 (hereinafter referred to as "Tyagi2 et al." except that Tyagi2 et al. also discloses that the nucleic acid Molecular Beacon may also be bimolecular wherein they define bimolecular as being unitary probes of the invention comprising two molecules (e.g. oligonucleotides) wherein half, or roughly half, of the target complement sequence, one member of the affinity pair and one member of the label pair are present in each molecule (See: Tyagi2 et al., p. 8, ln. 25 to p. 9, ln. 3). However, Tyagi2 et al. specifically states that in designing a unitary probe for use in a PCR reaction, one would naturally choose a target complement sequence that is not complementary to one of the PCR primers (See: Tyagi2 et al., p. 41, ln. 27). Assays of the invention include real-time and end point detection of specific single-stranded or double stranded products of nucleic acid synthesis reactions, provided however that if unitary probes will be subjected to melting or other denaturation, the probes must be unimolecular (See: Tyagi2 et al., p. 37, lns. 1-9). Furthermore, Tyagi2 et al. stipulate that although the unitary probes of the invention may be used with amplification or other nucleic acid synthesis reactions, bimolecular probes (as defined in Tyagi2 et al.) are not suitable for use in any reaction (e.g. PCR) wherein the affinity pair would be separated in a target-independent manner (See: Tyagi2 et al., p. 13, lns. 9-12). Neither Tyagi et al. nor Tyagi2 et al. disclose, suggest or teach anything about PNA.

In a more recent disclosure, modified hairpin constructs which are similar to the Tyagi et al. nucleic acid Molecular Beacons, but which are suitable as primers for polymerase extension, have been disclosed (See: Nazarenko et al., *Nucleic Acids Res.* 25: 2516-2521 (1997)). A method suitable for the direct detection of PCR-amplified DNA in a closed system is also disclosed. According to the method, the Nazarenko et al. primer constructs are, by operation of the PCR process, incorporated into the amplification product. Incorporation into a PCR amplified product results in a change in configuration which separates the donor and acceptor moieties. Consequently, increases in the intensity of the fluorescent signal in the assay can be directly correlated with the amount of primer incorporated into the PCR amplified product. The authors conclude, this method is particularly well suited to the analysis of PCR amplified nucleic acid in a closed tube format.

Because they are nucleic acids, the Nazarenko et al. primer constructs are admittedly subject to nuclease digestion thereby causing an increase in background signal during the PCR process (See: Nazarenko et al., *Nucleic Acids Res.* 25: at p. 2519, col. 1; lns. 28-39). An additional disadvantage of this method is that the Molecular Beacon like primer constructs must be linearized during amplification (See: Nazarenko et al., *Nucleic Acids Res.* 25: at p. 2519, col. 1, lns. 7-8). Consequently, the polymerase must read through and dissociate the stem of the hairpin modified Molecular Beacon like primer construct if fluorescent signal is to be generated. Nazarenko et al. does not suggest, teach or disclose anything about PNA.

In still another application of FRET to target nucleic acid sequence detection, doubly labeled fluorescent oligonucleotide probes which have also been used to detect target nucleic acid sequences in PCR reactions and in-situ PCR (See: Mayrand, U.S. Pat. No. 5,691,146). The oligonucleotide probes of Mayrand comprise a fluorescer (reporter) molecule attached to a first end of the oligonucleotide and a quencher molecule attached to the opposite end of the oligonucleotide (See: Mayrand, Abstract). Mayrand suggests that the prior art teaches that the distance between the fluorophore and quencher is an important feature which must be minimized and consequently the preferred spacing between the reporter and quencher moieties of a DNA probe should be 6-16 nucleotides (See: col. 7, lns. 8-24). Mayrand, however teaches that the reporter molecule and quencher moieties are preferably located at a distance of 18 nucleotides (See: col. 3, lns 35-36) or 20 bases (See: col. 7, lns. 25-46) to achieve the optimal signal to noise ratio. Consequently, both Mayrand and the prior art cited therein teach that the detectable properties of nucleic acid probes (DNA or RNA) comprising a fluorophore and quencher exhibit a strong dependence on probe length.

Resistance to nuclease digestion is also an important aspect of the invention (See: U.S. Pat. No. 5,691,146 at col. 6, lns. 42-64) and therefore, Mayrand suggests that the 5' end of the oligonucleotide may be rendered impervious to nuclease digestion by including one or more modified internucleotide linkages onto the 5' end of the oligonucleotide probe (See: U.S. Pat. No. 5,691,146 at col. 6, lns. 45-50). Furthermore, Mayrand suggests that a polyamide nucleic acid (PNA) or peptide can be used as a nuclease resistant linkage to thereby modify the 5' end of the oligonucleotide probe of the invention and render it impervious to nuclease digestion (See: U.S. Pat. No. 5,691,146 at col. 6, lns. 53-64). Mayrand does not however, disclose, suggest or teach that a PNA probe construct might be a suitable substitute for the practice of the invention despite having obvious knowledge of its existence. Furthermore, Mayrand does not teach one of skill in the art how to prepare and/or label a PNA with the fluorescer or quencher moieties.

The efficiency of energy transfer between donor and acceptor moieties as they can be influenced by oligonucleotide length (distance) has been further examined and particularly applied to fluorescent nucleic acid sequencing applications (See: Mathies et al., U.S. Pat. No. 5,707,804). Mathies et al. states that two fluorophores will be joined by a backbone or chain where the distance between the two fluorophores may be varied (See: U.S. Pat. No. 5,707,804 at col. 4, lns. 1-3). Thus, the distance must be chosen to provide energy transfer from the donor to the acceptor through the well-known Foerster mechanism (See: U.S. Pat. No. 5,707,804 at col. 4, lns. 7-9). Preferably about 3-10 nucleosides separate the fluorophores of a single stranded nucleic acid (See: U.S. Pat. No. 5,707,804 at col. 7, lns. 21-25). Mathies et al. does not suggest, teach or disclose anything about PNA.

From the analysis of DNA duplexes is has been observed that: 1: the efficiency of FET (or FRET as defined herein) appears to depend somehow on the nucleobase sequence of the oligonucleotide; 2: donor fluorescence changes in a manner which suggests that dye-DNA interactions affect the efficiency of FET; and 3: the Forster equation does not quantitatively account for observed energy transfer and therefore the length between donor and acceptor moieties attached to oligonucleotides cannot be quantitated, though it can be used qualitatively (See: Promisel et al., *Biochemistry*, 29: 9261-9268 (1990). Promisel et al. suggest that non-Forster effects may account for some of their observed but otherwise unexplainable results (See: Promisel et al., *Biochemistry*, 29: at p. 9267, col. 1, ln. 43 to p. 9268, col. 1, ln. 13). The results of Promisel et al. suggest that the FRET phenomena when utilized in nucleic acids in not entirely predictable or well understood. Promisel et al. does not suggest, teach or disclose anything about PNA and, in fact, the manuscript predates the invention of PNA.

The background art thus far discussed does not disclose, suggest or teach anything about PNA oligomers to which are directly attached a pair of donor and acceptor moieties. In fact, the FRET phenomenon as applied to the detection of nucleic acids, appears to be confined to the preparation of constructs in which the portion of the probe which is complementary to the target nucleic acid sequence is itself comprised solely of nucleic acid.

FRET has also been utilized within the field of peptides. (See: Yaron et al. *Analytical Biochemistry* 95 at p. 232, col. 2, ln. 30 to p. 234, col. 1, ln. 30). Indeed, the use of suitably labeled peptides as enzyme substrates appears to be the primary utility for peptides which are labeled with donor and acceptor pairs (See: Zimmerman et al., *Analytical Biochemistry*, 70: 258-262 (1976), Carmel et al., *Eur. J. Biochem.*, 73: 617-625 (1977), Ng et al., *Analytical Biochemistry*, 183: 50-56 (1989), Wang et al., *Tett. Lett.*, 31: 6493-6496 (1990) and Meldal et al., *Analytical Biochemistry*, 195: 141-147 (1991). Early work suggested that quenching efficiency of the donor and acceptor pair was dependent on peptide length (See: Yaron et al., *Analytical Biochemistry* 95 at p. 233, col. 2, lns. 36-40). However, the later work has suggested that efficient quenching was not so dependent on peptide length (See: Ng et al., *Analytical Biochemistry*, 183: at p. 54, col. 2, ln 23 to p. 55, col. 1, ln. 12; Wang et al., *Tett. Lett.*, 31 wherein the peptide is eight amino acids in length; and Meldal et al. *Analytical Biochemistry*, 195 at p. 144, col. 1, lns. 33-37). It was suggested by Ng et al. that the observed quenching in long peptides might occur by an as yet undetermined mechanism (See: Ng et al., *Analytical Biochemistry* 183 at p. 55, col. 1, ln 13 to col. 2, ln 7.)

Despite its name, peptide nucleic acid (PNA) is neither a peptide, a nucleic acid nor is it even an acid. Peptide Nucleic Acid (PNA) is a non-naturally occurring polyamide (pseudopeptide) which can hybridize to nucleic acid (DNA and RNA) with sequence specificity (See U.S. Pat. No. 5,539, 082 and Egholm et al., *Nature* 365: 566-568 (1993)). PNAs are synthesized by adaptation of standard peptide synthesis procedures in a format which is now commercially available. (For a general review of the preparation of PNA monomers and oligomers please see: Dueholm et al., *New J. Chem.*, 21: 19-31 (1997) or Hyrup et. al., *Bioorganic & Med. Chem.* 4: 5-23 (1996)). Alternatively, labeled and unlabeled PNA oligomers can be purchased (See: PerSeptive Biosystems Promotional Literature: BioConcepts, Publication No. NL612, Practical PNA, *Review* and Practical PNA, Vol. 1, Iss. 2)

Being non-naturally occurring molecules, PNAs are not known to be substrates for the enzymes which are known to degrade peptides or nucleic acids. Therefore, PNAs should be stable in biological samples, as well as have a long shelf-life. Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.* 118: 5544-5552 (1996)). Sequence discrimination is more efficient for PNA recognizing DNA than for DNA recognizing DNA (Egholm et al., *Nature*, at p. 566). However, the advantages in point mutation discrimination with PNA probes, as compared with DNA probes, in a hybridization assay appears to be somewhat sequence dependent (Nielsen et al., *Anti-Cancer Drug Design* 8: 53-65, (1993)). As an additional advantage, PNAs hybridize to nucleic acid in both a parallel and antiparallel orientation, though the antiparallel orientation is preferred (See: Egholm et al., *Nature* at p. 566).

Despite the ability to hybridize to nucleic acid in a sequence specific manner, there are many differences between PNA probes and standard nucleic acid probes. These differences can be conveniently broken down into biological, structural, and physico-chemical differences. As discussed in more detail below, these biological, structural, and physico-chemical differences may lead to unpredictable results when attempting to use PNA probes in applications were nucleic acids have typically been employed. This non-equivalency of differing compositions is often observed in the chemical arts.

With regard to biological differences, nucleic acids, are biological materials that play a central role in the life of living species as agents of genetic transmission and expression. Their in vivo properties are fairly well understood. PNA, on the other hand is recently developed totally artificial molecule, conceived in the minds of chemists and made using synthetic organic chemistry. It has no known biological function (i.e. native (unmodified) PNA is not known to be a substrate for any polymerase, ligase, nuclease or protease).

Structurally, PNA also differs dramatically from nucleic acid. Although both can employ common nucleobases (A, C, G, T, and U), the backbones of these molecules are structurally diverse. The backbones of RNA and DNA are composed of repeating phosphodiester ribose and 2-deoxyribose units. In contrast, the backbones of the most common PNAs are composed on N-[2-(aminoethyl)]glycine subunits. Additionally, in PNA the nucleobases are connected to the backbone by an additional methylene carbonyl moiety.

PNA is not an acid and therefore contains no charged acidic groups such as those present in DNA and RNA. Because they lack formal charge, PNAs are generally more hydrophobic than their equivalent nucleic acid molecules. The hydrophobic character of PNA allows for the possibility of non-specific (hydrophobic/hydrophobic interactions) interactions not observed with nucleic acids. Further, PNA is achiral, providing it with the capability of adopting structural conformations the equivalent of which do not exist in the RNA/DNA realm.

The unique structural features of PNA result in a polymer which is highly organized in solution, particularly for purine rich polymers (See: Dueholm et al., *New J. Chem.*, 21: 19-31 (1997) at p. 27, col. 2, lns. 6-30). Conversely, a single stranded nucleic acid is a random coil which exhibits very little secondary structure. Because PNA is highly organized, PNA should be more resistant to adopting alternative secondary structures (e.g. a hairpin stem and/or loop).

The physico/chemical differences between PNA and DNA or RNA are also substantial. PNA binds to its complementary nucleic acid more rapidly than nucleic acid probes bind to the same target sequence. This behavior is believed to be, at least partially, due to the fact that PNA lacks charge on its backbone. Additionally, recent publications demonstrate that the incorporation of positively charged groups into PNAs will improve the kinetics of hybridization (See: Iyer et al., *J. Biol. Chem.* 270:14712-14717 (1995)). Because it lacks charge on the backbone, the stability of the PNA/nucleic acid complex is higher than that of an analogous DNA/DNA or RNA/DNA complex. In certain situations, PNA will form highly stable triple helical complexes through a process called "strand displacement". No equivalent strand displacement processes or structures are known in the DNA/RNA world.

Recently, the "Hybridization based screening on peptide nucleic acid (PNA) oligomer arrays" has been described wherein arrays of some 1000 PNA oligomers of individual sequence were synthesized on polymer membranes (See: Weiler et al., *Nucl. Acids Res.* 25: 2792-2799 (1997)). Arrays are generally used, in a single assay, to generate affinity binding (hybridization) information about a specific sequence or sample to numerous probes of defined composition. Thus, PNA arrays may be useful in diagnostic applications or for screening libraries of compounds for leads which might exhibit therapeutic utility. However, Weiler et al. note that the affinity and specificity of DNA hybridization to immobilized PNA oligomers depended on hybridization conditions more than was expected. Moreover, there was a tendency toward non-specific binding at lower ionic strength. Furthermore, certain very strong binding mismatches were identified which could not be eliminated by more stringent washing conditions. These unexpected results are illustrative of the lack of complete understanding of these newly discovered molecules (i.e. PNA).

In summary, because PNAs hybridize to nucleic acids with sequence specificity, PNAs are useful candidates for investigation as substitute probes when developing probe-based hybridization assays. However, PNA probes are not the equivalent of nucleic acid probes in both structure or function. Consequently, the unique biological, structural, and physicochemical properties of PNA requires that experimentation be performed to thereby examine whether PNAs are suitable in applications where nucleic acid probes are commonly utilized.

SUMMARY OF THE INVENTION

Numerous PNA polymers were examined in an attempt to prepare a PNA Molecular Beacon. The applicants have determined that all PNA oligomers they examined, which contained donor and acceptor moieties located at opposite ends of the polymer, exhibited a low inherent background and a detectable increase in signal upon binding of the probe to a target sequence. Very surprisingly, these characteristic properties of a nucleic acid Molecular Beacon were observed whether or not the PNA oligomer was suitable for adopting a hairpin stem and loop structure in a manner commensurate with the design of the nucleobase sequence. For example, in hybridization assay analysis, the PNA oligomers (originally designed as control oligomers) which do not possess any arm segments suitable for creating a hairpin, exhibited a signal (PNA oligomer bound to target sequence) to noise (no target sequence present) ratio which is approximately half that observed for PNAs which comprise self-complementary nucleobase sequences.

This invention is directed to Linear Beacons. A Linear Beacon, efficiently transfers energy between the donor and acceptor moieties linked to the probe in the absence of target sequence whether or not, by design, it comprises self complementary nucleobase sequence. Upon hybridization to a target sequence, the efficiency of energy transfer between donor and acceptor moieties of the Linear Beacon is altered such that detectable signal from at least one moiety can be used to monitor or quantitate occurrence of the hybridization event. We refer to these probes as Linear Beacons to distinguish them from the hairpin structures typically associated with nucleic acid Molecular Beacons. Nevertheless, applicants do not intend to imply that these probes lack a secondary structure since the literature teaches that PNAs can be highly organized in solution (See: Dueholm et al., *New J. Chem.*, 21: 19-31 (1997 at p. 27, col. 2, lns. 6-30).

The Linear Beacons of this invention possess several properties which are unique and not predicable. For example, applicants demonstrate that the efficiency of energy transfer between donor and acceptor moieties of a Linear Beacon is substantially independent of length since essentially the same noise (See: Example 17 of this specification) and signal to noise ratio (See: Example 18 of this specification) was observed for oligomers of 11-17 subunits in length. This was a very surprising result since the intramolecular quenching of suitably labeled nucleic acid oligomers is very dependent on the length of the probe (See: Background and the data presented in Example 17 of this specification).

Additionally, applicants have demonstrated that the efficiency of quenching of a Linear Beacon is neither sequence dependent, nor substantially dependent on the spectral overlap of the donor and acceptor moieties (See: Examples 17, 18 and 21 of this specification). Specifically, the majority of PNA probes which were prepared comprise a fluorescein donor moiety and a dabcyl quencher (acceptor) moiety. Though this donor/acceptor combination is not an ideal FRET pair since the emission of the donor fluorescein moiety does not have a high degree of spectral overlap with the absorption of the acceptor dabcyl moiety, the quenching observed by applicants is nevertheless substantial in all constructs. Furthermore, Linear Beacons comprising the Cy3/dabcyl donor/acceptor pair, respectively, were observed to exhibit both a noise and a signal to noise ratio which was similar to that seen for the fluorescein/dabcyl system despite there being substantially less spectral overlap between Cy3 and dabcyl (See: Examples 17, 18 and 21 of this specification). Consequently, the data compiled by applicants surprisingly demonstrates that Linear Beacons need not comprise optimal FRET pairs to be operable. Consequently, the data suggests that direct contact is the primary, but likely not the only, mode of energy transfer since spectral overlap is a requirement for FRET but is not required for non-FRET energy transfer. Furthermore, the data suggests that regardless of probe length, the fluorophore and quencher moieties of a Linear Beacon are similarly situated to thereby achieve a degree of quenching which is fairly independent of probe length or nucleobase sequence.

Applicants have likewise investigated what effect varying ionic strength and particularly the presence or absence that magnesium has on probe noise and signal to noise ratios. Again, PNAs were found to exhibit noise and signal to noise ratios which were substantially independent of differences in ionic strength or presence or absence of magnesium whereas the properties of DNA probes of similar length and labeling configuration were dependent on variations in ionic strength and/or highly dependent on the presence or absence of magnesium.

In summary, it has also been observed by applicants that the noise and signal to noise ratio for Linear Beacons is substantially independent of length of subunits which separate donor and acceptor moieties, ionic strength of the environment or the presence or absence of magnesium. When considered as a whole, these results were very unexpected in light of prior art teachings. Consequently, applicants data demonstrates a clear non-equivalency of structure and function between nucleic acid and PNA probes of similar length and labeling configurations. It follows that the novel methods, kits and compositions of this invention comprise Linear Beacons which possess unique and surprising properties.

In one embodiment, this invention is directed to a Linear Beacon. Generally, a Linear Beacon is a polymer which at a minimum comprises at least one linked donor moiety and at least one linked acceptor moiety wherein said donor and acceptor moieties are separated by a at least a portion of a probing nucleobase sequence wherein the probing nucleobase sequence is suitable for hybridization to a complementary or substantially complementary target sequence, under suitable hybridization conditions. By design, a Linear Beacon does not form a hairpin stem. The Linear Beacon is further characterized in that the efficiency of transfer of energy between said donor and acceptor moieties, when the polymer is solvated in aqueous solution, is substantially independent of at least two variable factors selected from the group consisting of length of subunits which separate donor and acceptor moieties, spectral overlap of the donor moiety and the acceptor moiety, presence or absence of magnesium in the aqueous solution and the ionic strength of the aqueous solution. Preferably the Linear Beacon is further characterized in that the efficiency of transfer of energy between said donor and acceptor moieties is substantially independent of at least three variable factors and most preferably substantially independent of all four variable factors.

In a preferred embodiment, a Linear Beacon is a polymer comprising PNA subunits which, at a minimum, consists of a probing nucleobase sequence having a first and second end. The probing nucleobase sequence is complementary or substantially complementary to a target sequence of interest. At least one donor moiety is linked to one of the first or second ends of the probing nucleobase sequence; and at least one acceptor moiety is linked to the other one of the first or second end of the probing nucleobase sequence. One or more spacer or linker moieties may be used to link the donor and acceptor moieties to the respective ends of the probing nucleobase sequence.

In another embodiment, this invention is related to a method for the detection, identification or quantitation of a target sequence in a sample. The method comprises contacting the sample with a Linear Beacon and then detecting, identifying or quantitating the change in detectable signal associated with at least one donor or acceptor moiety of the probe whereby the change in detectable signal is used to determine the presence, absence or amount of target sequence present in the sample of interest. The measurable change in detectable signal of at least one donor or acceptor moiety of the probe can be used to determine the presence, absence or amount of target sequence present in the sample of interest since applicants have demonstrated that the efficiency of energy transfer between donor and acceptor moieties is altered by hybridization of the Linear Beacons to their intended target sequences, under suitable hybridization conditions. Accurate quantitation can be achieved by correcting for signal generated by any unhybridized Linear Beacon. Consequently, the Linear Beacons of this invention are particularly well suited for the detection, identification or quantitation of target sequences in closed tube assays and particularly asymmetric PCR assays (See: Example 19 of this specification). Because the Linear Beacons are not known to be degraded by enzymes, the Linear Beacons are also particularly well suited for detection, identification or quantitation of target sequences in cells, tissues or organisms, whether living or not (See: Example 20 of this specification).

In still another embodiment, this invention is related to kits suitable for performing an assay which detects the presence, absence or number of a target sequences in a sample. The kits of this invention comprise one or more Linear Beacons and other reagents or compositions which are selected to perform an assay or otherwise simplify the performance of an assay.

In yet another embodiment, this invention also is directed to an array comprising two or more support bound Linear Beacons suitable for detecting, identifying or quantitating a target sequence of interest. Arrays of Linear Beacons are convenient because they provide a means to rapidly interrogate numerous samples for the presence of one or more target sequences of interest in real time without using a secondary detection system.

The methods, kits and compositions of this invention are particularly useful for the detection of target sequences of organisms which may be found in food, beverages, water, pharmaceutical products, personal care products, dairy products or environmental samples. The analysis of preferred beverages include soda, bottled water, fruit juice, beer, wine or liquor products. Additionally, the methods, kits and compositions will be particularly useful for the analysis of raw materials, equipment, products or processes used to manufacture or store food, beverages, water, pharmaceutical products, personal care products dairy products or environmental samples.

Whether support bound or in solution, the methods, kits and compositions of this invention are particularly useful for the rapid, sensitive, reliable and versatile detection of target sequences which are particular to organisms which might be found in clinical environments. Consequently, the methods, kits and compositions of this invention will be particularly useful for the analysis of clinical specimens or equipment, fixtures or products used to treat humans or animals. For example, the assay may be used to detect a target sequence which is specific for a genetically based disease or is specific for a predisposition to a genetically based disease. Non-limiting examples of diseases include, β-Thalassemia, sickle cell anemia, Factor-V Leiden, cystic fibrosis and cancer related targets such as p53, p10, BRC-1 and BRC-2.

In still another embodiment, the target sequence may be related to a chromosomal DNA, wherein the detection, identification or quantitation of the target sequence can be used in relation to forensic techniques such as prenatal screening, paternity testing, identity confirmation or crime investigation.

BRIEF DESCRIPTION OF THE DRAWINGS

FIGS. 1B1, 1B2 and 1B3 are graphical illustrations of fluorescence vs. temperature data for PNA probes which exhibit a Type B Fluorescent Thermal Profile.

FIGS. 2A1, 2A2 and 2A3 are a graphical illustration of fluorescence vs. time data for PNA probes which exhibit a Type A Hybridization Profile.

FIG. 2B is a graphical illustration of fluorescence vs. time data for PNA probes which exhibit a Type B Hybridization Profile.

FIG. 3 is a graphical illustration of noise (background fluorescence) data for DNA and PNA probes of different lengths and labeling configurations.

FIGS. 4A, 4B, 4C, 4D and 4E are graphical illustrations of signal to noise data for PNA and DNA probes of 11 and 15 subunits in length.

FIGS. 6A and 6B are digital images of sample slides containing *E. coli*, *P. aeruginosa* or *B. subtilis* bacteria which were treated with Linear Beacons and propidium iodide wherein the Linear Beacons comprise probing nucleobase sequence specific to either *P. aeruginosa* (FIG. 6A) or *B. subtilis* (FIG. 6B). The images were obtained using a fluorescence microscope and commercially available light filters fitted to the microscope and the camera respectively. In both Figures, Panels I, III and IV are the red images obtained using a red microscope and camera filter wherein the propidium iodide stained cells are visible. In both Figures, Panels II, IV and VI are the green images obtained using a green microscope and camera filter.

FIGS. 7A and 7B are graphical representations of data compiled for noise and signal to noise ratios for a Cy3 labeled 15-mer PNA probe having a scrambled nucleobase sequence.

FIG. 8 is a graphical illustration of hybridization assay signal to noise ratios for probes listed in Table 1A.

DESCRIPTION OF THE PREFERRED EMBODIMENTS

Figure 1A:
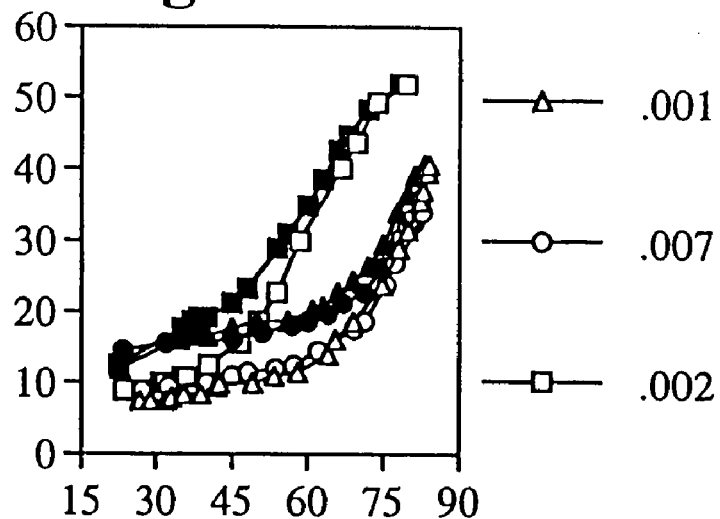
FIG. 1A is a graphical illustration of fluorescence vs. temperature data for PNA probes which exhibit a Type A Fluorescent Thermal Profile.

1. Definitions:

a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.

b. As used herein, the term "nucleobase sequence" is any segment of a polymer which comprises nucleobase containing subunits. Non-limiting examples of suitable polymers or polymers segments include oligonucleotides, oligoribonucleotides, peptide nucleic acids and analogs or chimeras thereof.

c. As used herein, the term "target sequence" is any sequence of nucleobases in a polymer which is sought to be detected. The "target sequence" may comprise the entire polymer or may be a subsequence of the nucleobase sequence which is unique to the polymer of interest. Without limitation, the polymer comprising the "target sequence" may be a nucleic acid, a peptide nucleic acid, a chimera, a linked polymer, a conjugate or any other polymer comprising substituents (e.g. nucleobases) to which the Linear Beacons of this invention may bind in a sequence specific manner.

d. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539, 082, 5,527,675, 5,623,049, 5,714,331, 5,736,336, 5,773, 571 or 5,786,571 (all of which are herein incorporated by reference). The term "Peptide Nucleic Acid" or "PNA" shall also apply to those nucleic acid mimics described in the following publications: Diderichsen et al., *Tett. Lett.* 37:475-478 (1996); Fujii et al., *Bioorg. Med. Chem. Lett.* 7:637-627 (1997); Jordan et al., *Bioorg. Med. Chem. Lett.* 7:687-690 (1997); Krotz et al., *Tett. Lett.* 36:6941-6944 (1995); Lagriffoul et al., *Bioorg. Med. Chem. Lett.* 4:1081-1082 (1994); Lowe et al., *J. Chem. Soc. Perkin Trans.* 1, (1997) 1:539-546; Lowe et al., *J. Chem. Soc. Perkin Trans.* 1 1:547-554 (1997); Lowe et al., *J. Chem. Soc. Perkin Trans.* 1 1:555-560 (1997); and Petersen et al., *Bioorg. Med. Chem. Lett.* 6:793-796 (1996).

In preferred embodiments, a PNA is a polymer comprising two or more PNA subunits of the formula:

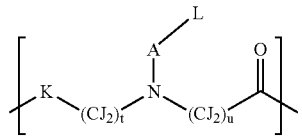

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; $-(CJ_2)_s-$ and a group of the formula; $-(CJ_2)_sC(O)-$, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin and fluorescein. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

2. Detailed Description

I. General:

PNA Synthesis:

Methods for the chemical assembly of PNAs are well known (See: U.S. Pat. Nos. 5,539,082, 5,527,675, 5,623,049, 5,714,331, 5,736,336, 5,773,571 or 5,786,571 (all of which are herein incorporated by reference). Chemicals and instrumentation for the support bound automated chemical assembly of Peptide Nucleic Acids are now commercially available. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

Labels:

The labels attached to the Linear Beacons of this invention comprise a set (hereinafter "Beacon Set(s)") of energy transfer moieties comprising at least one energy donor and at least one energy acceptor moiety. Typically, the Beacon Set will include a single donor moiety and a single acceptor moiety. Nevertheless, a Beacon Set may contain more than one donor moiety and/or more than one acceptor moiety. The donor and acceptor moieties operate such that one or more acceptor moieties accepts energy transferred from the one or more donor moieties or otherwise quench signal from the donor moiety or moieties.

Preferably the donor moiety is a fluorophore. Preferred fluorophores are derivatives of fluorescein, derivatives of bodipy, 5-(2'-aminoethyl)-aminonaphthalene-1-sulfonic acid (EDANS), derivatives of rhodamine, Cy2, Cy3, Cy 3.5, Cy5, Cy5.5, texas red and its derivatives. Though the previously listed fluorophores might also operate as acceptors, preferably, the acceptor moiety is a quencher moiety. Preferably, the quencher moiety is a non-fluorescent aromatic or heteroaromatic moiety. The preferred quencher moiety is 4-((-4-(dimethylamino)phenyl)azo)benzoic acid (dabcyl).

Transfer of energy may occur through collision of the closely associated moieties of a Beacon Set or through a nonradiative process such as fluorescence resonance energy transfer (FRET). For FRET to occur, transfer of energy between donor and acceptor moieties of a Beacon Set requires that the moieties be close in space and that the emission spectrum of a donor(s) have substantial overlap with the absorption spectrum of the acceptor(s) (See: Yaron et al. *Analytical Biochemistry*, 95: 228-235 (1979) and particularly page 232, col. 1 through page 234, col. 1). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies) (See: Yaron et al., *Analytical Biochemistry*, 95: 228-235 (1979) and particularly page 229, col. 1 through page 232, col. 1). This process is referred to as intramolecular collision since it is believed that quenching is caused by the direct contact of the donor and acceptor moieties (See: Yaron et al.). As applicants have demonstrated, the donor and acceptor moieties attached to the Linear Beacons of this invention need not have a substantial overlap between the emission of the donor moieties and the absorbance of the acceptor moieties. Without intending to be bound to this hypothesis, this data suggests that collision or contact operates as the primary mode of quenching in Linear Beacons.

Detecting Energy Transfer:

Because the efficiency of both collision mediated and non-radiative transfer of energy between the donor and acceptor moieties of a Beacon Set is directly dependent on the proximity of the donor and acceptor moieties, detection of hybrid formation of a Linear Beacon with a target sequence can be monitored by measuring at least one physical property of at least one member of the Beacon Set which is detectably different when the hybridization complex is formed as compared with when the Linear Beacon exists in the absence of target sequence. We refer to this phenomenon as the self-indicating property of Linear Beacons. This change in detectable signal shall result from the change in efficiency of energy transfer between the donor and acceptor which results from hybridization of the Linear Beacon. Preferably, the means of detection will involve measuring fluorescence of a donor or acceptor fluorophore of a Beacon Set. Most preferably, the Beacon Set will comprise at least one donor fluorophore and at least one acceptor quencher such that the fluorescence of the donor fluorophore is will be used to detect, identify or quantitate hybridization.

PNA Labeling:

Chemical labeling of a PNA is analogous to peptide labeling. Because the synthetic chemistry of assembly is essentially the same, any method commonly used to label a peptide may be used to label a PNA. Typically, the N-terminus of the polymer is labeled by reaction with a moiety having a carboxylic acid group or activated carboxylic acid group. One or more spacer moieties can optionally be introduced between the labeling moiety and the probing nucleobase sequence of the oligomer. Generally, the spacer moiety is incorporated prior to performing the labeling reaction. However, the spacer may be embedded within the label and thereby be incorporated during the labeling reaction.

Typically the C-terminal end of the probing nucleobase sequence is labeled by first condensing a labeled moiety with the support upon which the PNA is to be assembled. Next, the first synthon of the probing nucleobase sequence can be condensed with the labeled moiety. Alternatively, one or more spacer moieties can be introduced between the labeled moiety and the oligomer (e.g. 8-amino-3,6-dioxaoctanoic acid). Once the Linear Beacon is completely assembled and labeled, it is cleaved from the support deprotected and purified using standard methodologies.

The labeled moiety could be a lysine derivative wherein the ε-amino group is modified with a donor or acceptor moiety. For example the label could be a fluorophore such as 5(6)-carboxyfluorescein or a quencher moiety such as 4-((4-(dimethylamino)phenyl)azo)benzoic acid (dabcyl). Condensation of the lysine derivative with the synthesis support would be accomplished using standard condensation (peptide) chemistry. The α-amino group of the lysine derivative would then be deprotected and the probing nucleobase sequence assembly initiated by condensation of the first PNA synthon with the α-amino group of the lysine amino acid. As discussed above, a spacer moiety could optionally be inserted between the lysine amino acid and the first PNA synthon by condensing a suitable spacer (e.g. Fmoc-8-amino-3,6-dioxaoctanoic acid) with the lysine amino acid prior to condensation of the first PNA synthon of the probing nucleobase sequence.

Alternatively, a functional group on the assembled, or partially assembled, polymer is labeled with a donor or acceptor moiety while it is still support bound. This method requires that an appropriate protecting group be incorporated into the oligomer to thereby yield a reactive functional group to which the donor or acceptor moiety is linked but has the advantage that the label (e.g. dabcyl or a fluorophore) can be attached to any position within the polymer including within the probing nucleobase sequence. For example, the ε-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from PNA (assembled using commercially available Fmoc PNA monomers and polystyrene support having a PAL linker; PerSeptive Biosystems, Inc., Framingham, Mass.) by treatment of the resin under mildly acidic conditions. Consequently, the donor or acceptor moiety can then be condensed with the ε-amino group of the lysine amino acid. After complete assembly and labeling, the polymer is then cleaved from the support, deprotected and purified using well known methodologies.

By still another method, the donor or acceptor moiety is attached to the polymer after it is fully assembled and cleaved from the support. This method is preferable where the label is incompatible with the cleavage, deprotection or purification regimes commonly used to manufacture the oligomer. By this method, the PNA will generally be labeled in solution by the reaction of a functional group on the polymer and a functional group on the label. Those of ordinary skill in the art will recognize that the composition of the coupling solution will depend on the nature of oligomer and the donor or acceptor moiety. The solution may comprise organic solvent, water or any combination thereof. Generally, the organic solvent will be a polar non-nucleophilic solvent. Non limiting examples of suitable organic solvents include acetonitrile, tetrahydrofuran, dioxane, methyl sulfoxide and N,N'-dimethylformamide.

Generally the functional group on the polymer to be labeled will be an amine and the functional group on the label will be a carboxylic acid or activated carboxylic acid. Non-limiting examples of activated carboxylic acid functional groups include N-hydroxysuccinimidyl esters. In aqueous solutions, the carboxylic acid group of either of the PNA or label (depending on the nature of the components chosen) can be activated with a water soluble carbodiimide. The reagent, 1-(3-dimethylaminopropyl)-3-ethylcarbodiimide hydrochloride (EDC), is a commercially available reagent sold specifically for aqueous amide forming condensation reactions.

Generally, the pH of aqueous solutions will be modulated with a buffer during the condensation reaction. Preferably, the pH during the condensation is in the range of 4-10. When an arylamine is condensed with the carboxylic acid, preferably the pH is in the range of 4-7. When an alkylamine is condensed with a carboxylic acid, preferably the pH is in the range of 7-10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH is modulated using biological buffers such as (N-[2-hydroxyethyl]piperazine-N'-[2-ethanesulfonic acid) (HEPES) or 4-morpholineethanesulfonic acid (MES) or inorganic buffers such as sodium bicarbonate.

Spacer/Linker Moieties:

Generally, spacers are used to minimize the adverse effects that bulky labeling reagents might have on hybridization properties of Linear Beacons. Linkers typically induce flexibility and randomness into the Linear Beacon or otherwise link two or more nucleobase sequences of a probe. Preferred spacer/linker moieties for probes of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid) or alkyloxy diacids (e.g. diglycolic acid). The spacer/linker moieties may also be designed to enhance the solubility of the Linear Beacon.

Preferably, a spacer/linker moiety comprises one or more linked compounds having the formula: —Y—$(O_m$—$(CW_2)_n)_o$—Z—. The group Y has the formula: a single bond, —$(CW_2)_p$—, —$C(O)(CW_2)_p$—, —$C(S)(CW_2)_p$— and —$S(O_2)(CW_2)_p$. The group Z has the formula NH, $NR^2$, S or O. Each W is independently H, $R^2$, —$OR^2$, F, Cl, Br or I; wherein, each $R^2$ is independently selected from the group consisting of: —$CX_3$, —$CX_2CX_3$, —$CX_2CX_2CX_3$, —$CX_2CX(CX_3)_2$, and —$C(CX_3)_3$. Each X is independently H, F, Cl, Br or I. Each m is independently 0 or 1. Each n, o and p are independently integers from 0 to 10.

Chimeric Oligomer:

A chimeric oligomer comprises two or more linked subunits which are selected from different classes of subunits. For example, a PNA/DNA chimera would comprise at least two PNA subunits linked to at least one 2'-deoxyribonucleic acid subunit (For methods and compositions related to PNA/DNA chimera preparation See: WO96/40709). The component subunits of the chimeric oligomers are selected from the group consisting of PNA subunits, DNA subunits, RNA subunits and analogues thereof.

Linked Polymer:

A linked polymer comprises two or more nucleobase sequences which are linked by a linker. The nucleobase sequences which are linked to form the linked polymer are selected from the group consisting of an oligodeoxynucleotide, an oligoribonucleotide, a peptide nucleic acid and a chimeric oligomer. The PNA probes of this invention include linked polymers wherein the probing nucleobase sequence is linked to one or more additional oligodeoxynucleotide, oligoribonucleotide, peptide nucleic acid or chimeric oligomers.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probing nucleobase sequence/target sequence combination is often found by the well known technique of fixing several of the aforementioned stringency factors and then determining the effect of varying a single stringency factor. The same stringency factors can be modulated to thereby control the stringency of hybridization of Linear Beacons to target sequences, except that the hybridization of a PNA is fairly independent of ionic strength. Optimal stringency for an assay may be experimentally determined by examination of each stringency factor until the desired degree of discrimination is achieved.

Probing Nucleobase Sequence:

The probing nucleobase sequence of a Linear Beacon is the sequence recognition portion of the construct. Therefore, the probing nucleobase sequence is designed to hybridize to at least a portion of the target sequence. Preferably the probing nucleobase sequence hybridizes to the entire target sequence. The probing nucleobase sequence is a non-polynucleotide and preferably the probing nucleobase sequence is composed exclusively of PNA subunits. The subunit length of the probing nucleobase sequence will therefore generally be chosen such that a stable complex is formed between the Linear Beacon and the target sequence sought to be detected, under suitable hybridization conditions. The probing nucleobase sequence of a PNA oligomer, suitable for the practice of this invention, will generally have a length of between 5 and 30 PNA subunits. Preferably, the probing nucleobase sequence will be 8 to 18 subunits in length. Most preferably, the probing nucleobase sequence will be 11-17 subunits in length.

The probing nucleobase sequence of Linear Beacons will generally have a nucleobase sequence which is complementary to the target sequence. Alternatively, a substantially complementary probing sequence might be used since it has been demonstrated that greater sequence discrimination can be obtained when utilizing probes wherein there exists a single point mutation (base mismatch) between the probing nucleobase sequence and the target sequence (See: Guo et al., Nature Biotechnology 15: 331-335 (1997), Guo et al., WO97/46711; and Guo et al., U.S. Pat. No. 5,780,233, herein incorporated by reference).

Blocking Probes:

Blocking probes are PNA or nucleic acid probes which can be used to suppress the binding of the probing nucleobase sequence of a probe to a hybridization site which is unrelated or closely related to the target sequence (See: Coull et al., PCT/US97/21845, a.k.a. WO98/24933). Generally, the blocking probes suppress the binding of the probing nucleobase sequence to closely related non-target sequences because the blocking probe hybridizes to the non-target sequence to form a more thermodynamically stable complex than is formed by hybridization between the probing nucleobase sequence and the non-target sequence. Thus, blocking probes are typically unlabeled probes used in an assay to thereby suppress non-specific signal. Because they are usually designed to hybridize to closely related non-target sequence sequences, typically a set of two or more blocking probes will be used in an assay to thereby suppress non-specific signal from non-target sequences which could be present and interfere with the performance of the assay.

II. Preferred Embodiments of the Invention:

Linear Beacon Probes:

Linear Beacons are disclosed which are suitable for facilitating energy transfer between donor and acceptor moieties when the probe is not hybridized to its target sequence. However, hybridization of the probe to its target sequence will alter the efficiency of energy transfer between donor and acceptor moieties and thereby result in a measurable change in signal associated with at least one member of the Beacon Set.

Generally, a Linear Beacon is a polymer which at a minimum comprises at least one linked donor moiety and at least one linked acceptor moiety wherein said donor and acceptor moieties are separated by a at least a portion of a probing nucleobase sequence wherein the probing nucleobase sequence is suitable for hybridization to a complementary or substantially complementary target sequence, under suitable hybridization conditions. By design, a Linear Beacon does not form a hairpin stem. Preferably the donor and acceptor moieties are linked at opposite ends of the probing nucleobase sequence. The Linear Beacon is further characterized in that the efficiency of transfer of energy between said donor and acceptor moieties, when the polymer is solvated in aqueous solution, is substantially independent of at least two variable factors selected from the group consisting of length of subunits which separate donor and acceptor moieties, spectral overlap of the donor moiety and the acceptor moiety, presence or absence of magnesium in the aqueous solution and the ionic strength of the aqueous solution. Preferably the Linear Beacon is further characterized in that the efficiency of transfer of energy between said donor and acceptor moieties is substantially independent of at least three variable factors and most preferably substantially independent of all four variable factors.

In a preferred embodiment, the Linear Beacon is a polymer which, at a minimum, consists of a probing nucleobase sequence having a first and second end. The probing nucleobase sequence is complementary or substantially complementary to a target sequence of interest. At least one donor moiety is linked to one of the first or second ends of the probing nucleobase sequence; and at least one acceptor moiety is linked to the other one of the first or second end of the probing nucleobase sequence. One or more spacer or linker moieties may be used to link the donor and acceptor moieties to the respective ends of the probing nucleobase sequence. In a most preferred embodiment, the Linear Beacon is a PNA oligomer.

Linear Beacons may comprise only a probing nucleobase sequence (as previously described herein) and linked donor and acceptor moieties of a Beacon Set or may optionally comprise additional linked moieties. Non-limiting examples of additional linked moieties include other labels, linkers, spacers, natural or non-natural amino acids, peptides, proteins, nucleic acids, enzymes and/or one or more other subunits of PNA, DNA or RNA. Additional moieties may be functional or non-functional in an assay. Generally however, additional moieties will be selected to be functional within the design of the assay in which the Linear Beacons is to be used. The Linear Beacons of this invention may optionally be immobilized to a surface.

As a non-limiting example, a Linear Beacon of this invention may comprise a nucleic acid linked to a probing nucleobase sequence wherein the nucleic acid might hybridize to a second target sequence. As a second non-limiting example, a Linear Beacon may comprise an enzyme linked to a probing nucleobase sequence wherein the enzyme might be used in a secondary detection scheme. A third non-limiting example of a Linear Beacon could comprise an antibody linked to the probing nucleobase sequence wherein the antibody might be used in a secondary detection scheme. As still a fourth non-limiting example, a Linear Beacon might comprise one or more spacer moieties linked to a probing nucleobase sequence wherein the one or more spacer moieties are used to tether the Linear Beacon to a support.

Unique Features of Linear Beacons:

There are many differences between prior art nucleic acid constructs and the Linear Beacons of this invention. For example, nucleic acid constructs comprise a polynucleotide backbone whereas the Linear Beacons of this invention comprise a probing nucleobase sequences which is other than a polynucleotide. In a preferred embodiment, Linear Beacons comprised of PNA exhibit all of the favorable properties of PNA such as resistance to nuclease degradation, salt independent sequence hybridization to complementary nucleic acids and extremely rapid hybridization kinetics.

Additionally, the transfer of energy between donor and acceptor moieties in a Linear Beacon is substantially independent on the presence or absence of magnesium, the ionic strength of the probe environment and the nucleobase sequence of the probe (See: Examples 17, 18 and 21 of this specification). More surprisingly, the efficiency of transfer of energy between donor and acceptor moieties of a Beacon Set is substantially independent of the length of subunits which separate donor and acceptor moieties whereas the energy transfer between moieties within nucleic acids having the same nucleobase sequence and labeling configuration exhibit a substantial dependence on probe length (See: Examples 17 and 18 of this specification).

Most surprisingly, Linear Beacons operate whether or not the donor and acceptor moieties exhibit substantial overlap of the emission spectrum of the donor moiety and the absorbance spectrum of acceptor moiety (See: Examples 17, 18 and 21 of this specification). Without intending to be bound to this hypothesis, this data suggests that collision or contact operates as the primary mode of energy transfer in Linear Beacons as compared with nucleic acids wherein FRET has been described as the primary source for energy transfer between donor and acceptor moieties.

Additional advantages of Linear Beacons include ease of synthesis as compared with constructs which comprise additional subunits to form arm segments. Additionally, the data compiled by applicants demonstrates that Linear Beacons hybridize faster than constructs which comprise additional subunits to form arm segments (See: Examples 15 and 16 of this specification).

Probe Sets:

In another embodiment, this invention is directed to sets of Linear Beacons suitable for detecting or identifying the presence, absence or amount of two or more different target sequences which might be present in a sample. The characteristics of Linear Beacons suitable for the detection, identification or quantitation of target sequences have been previously described herein. The grouping of Linear Beacons within sets characterized for specific detection of two or more target sequences is a preferred embodiment of this invention.

Probe sets of this invention shall comprise at least one Linear Beacon but need not comprise only Linear Beacons. For example, probe sets of this invention may comprise mixtures of Linear Beacons, other PNA probes and/or nucleic acid probes, provided however that a set comprises at least one Linear Beacon as described herein. In preferred embodiments, at least one probe of the set is a blocking probe, as defined herein.

Immobilization of a Linear Beacon to a Surface:

One or more Linear Beacons may optionally be immobilized to a surface. In one embodiment, the probe can be immobilized to the surface using the well known process of UV-crosslinking. Alternatively, the PNA oligomer is synthesized on the surface in a manner suitable for deprotection but not cleavage from the synthesis support.

Preferably, the probe is covalently linked to a surface by the reaction of a suitable functional groups on the probe and support. Functional groups such as amino groups, carboxylic acids and thiols can be incorporated in a Linear Beacon by extension of one of the termini with suitable protected moieties (e.g. lysine, glutamic acid and cystine). When extending the terminus, one functional group of a branched amino acid such as lysine can be used to incorporate the donor or acceptor label at the appropriate position in the polymer (See: Section entitled "PNA Labeling") while the other functional group of the branch is used to optionally further extend the polymer and immobilize it to a surface.

Methods for the attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the Linear Beacon. Because native PNA possesses an amino terminus, a PNA will not necessarily require modification to thereby immobilize it to a surface (See: Lester et al., Poster entitled "PNA Array Technology").

Conditions suitable for the immobilization of a PNA to a surface will generally be similar to those conditions suitable for the labeling of a PNA (See: subheading "PNA Labeling"). The immobilization reaction is essentially the equivalent of labeling the PNA whereby the label is substituted with the surface to which the PNA probe is to be covalently immobilized.

Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

When immobilized to a surface, energy transfer between moieties of a Beacon Set will occur in the Linear Beacon. Upon hybridization to a target sequence under suitable hybridization conditions, the location on the surface where the Linear Beacon (of known sequence) is attached will generate detectable signal based on the measurable change in signal of at least one member of the Beacon Set of the immobilized Linear Beacon. Consequently, the intensity of the signal on the surface can be used to detect, identify or quantitate the presence or amount of a target sequence in a sample which contacts the surface to which the Linear Beacon is immobilized. In a preferred embodiment, detection of surface fluorescence will be used to detect hybridization to a target sequence.

Detectable and Independently Detectable Moieties/Multiplex Analysis:

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label the different Linear Beacons of a set. The ability to differentiate between and/or quantitate each of the independently detectable moieties provides the means to multiplex a hybridization assay because the data which correlates with the hybridization of each of the distinctly (independently) labeled Linear Beacons to a target sequence can be correlated with the presence, absence or quantity of the target sequence sought to be detected in a sample. Consequently, the multiplex assays of this invention may be used to simultaneously detect the presence, absence or amount of one or more target sequences which may be present in the same sample in the same assay. Preferably, independently detectable fluorophores will be used as the independently detectable moieties of a multiplex assay using Linear Beacons. For example, two Linear Beacons might be used to detect each of two different target sequences wherein a fluorescein (green) labeled probe would be used to detect the first of the two target sequences and a rhodamine or Cy3 (red) labeled probe would be used to detect the second of the two target sequences. Consequently, a green, a red or a green and red signal in the assay would signify the presence of the first, second and first and second target sequences, respectively.

Arrays of Linear Beacons:

Arrays are surfaces to which two or more probes of interest have been immobilized at predetermined locations. Arrays comprising both nucleic acid and PNA probes have been described in the literature. The probe sequences immobilized to the array are judiciously chosen to interrogate a sample which may contain one or more target sequences of interest. Because the location and sequence of each probe is known, arrays are generally used to simultaneously detect, identify or quantitate the presence or amount of one or more target sequences in the sample. Thus, PNA arrays may be useful in diagnostic applications or in screening compounds for leads which might exhibit therapeutic utility.

For example, in a diagnostic assay a target sequence is captured by the complementary probe on the array surface and then the probe/target sequence complex is detected using a secondary detection system. In one embodiment the probe/target sequence complex is detected using a second probe which hybridizes to another sequence of the target molecule of interest. In another embodiment, a labeled antibody is used to detect, identify or quantitate the presence of the probe/target sequence complex.

Since the composition of the Linear Beacon is known at the location on the surface of the array (because the PNA was synthesized or attached to this position in the array), the composition of target sequence(s) can be directly detected, identified or quantitated by determining the location of detectable signal generated in the array. Because hybridization of the Linear Beacon to a target sequence is self-indicating, no secondary detection system is needed to analyze the array for hybridization between the Linear Beacon and the target sequence.

Arrays comprised of PNAs have the additional advantage that PNAs are highly stable and should not be degraded by enzymes which degrade nucleic acid. Therefore, PNA arrays should be reusable provided the nucleic acid from one sample can be striped from the array prior to introduction of the second sample. Upon stripping of hybridized target sequences, signal on the array of Linear Beacons should again become reduced to background. Because PNAs are not degraded by heat or endonuclease and exonuclease activity, arrays of Linear Beacon should be suitable for simple and rapid regeneration by treatment with heat, nucleases or chemical denaturants such as aqueous solutions containing formamide, urea and/or sodium hydroxide.

Methods:

In yet another embodiment, this invention is directed to a method for the detection, identification or quantitation of a target sequence in a sample. The method comprises contacting the sample with a Linear Beacon and then detecting, identifying or quantitating the change in detectable signal associated with at least one moiety of a Beacon Set whereby correlation between detectable signal and hybridization is possible since Linear Beacons are self-indicating. Because Linear Beacons are self-indicating, this method is particularly well suited to analysis performed in a closed tube assay (a.k.a. "homogeneous assays"). By closed tube assay we mean that once the components of the assay have been combined, there is no need to open the tube or remove contents of the assay to determine the result. Since the tube need not, and preferably will not, be opened to determine the result, there must be some detectable or measurable change which occurs and which can be observed or quantitated without opening the tube or removing the contents of the assay. Thus, most closed tube assays rely on a change in fluorescence which can be observed with the eye or otherwise detected and/or quantitated with a fluorescence instrument which uses the tube as the sample holder. Examples of such instruments include the Light Cycler from Idaho Technologies and the Prism 7700 from Perkin Elmer.

Preferred closed tube assays of this invention comprise the detection of nucleic acid target sequences which have been synthesized or amplified by operation of the assay. Non-limiting examples of preferred nucleic acid synthesis or nucleic acid amplification reactions are Polymerase Chain Reaction (PCR), Ligase Chain Reaction (LCR), Strand Displacement Amplification (SDA), Transcription-Mediated Amplification (TMA), Rolling Circle Amplification (RCA) and Q-beta replicase. The Linear Beacons present in the closed tube assay will generate detectable signal in response to target sequence production from the nucleic acid synthesis or nucleic acid amplification reaction occurring in the closed tube assay. In a most preferred embodiment, the assay is an asymmetric PCR reaction (See: Example 19 of this specification).

Because the Linear Beacons of this invention can be designed to be stable to the enzymes found in the cell, this method is particularly well suited to detecting a target sequence in a cell, tissue or organism, whether living or not. Thus, in preferred embodiments, in-situ hybridization is used as the assay format for detecting identifying or quantitating target organisms (See: Example 20 of this specification). Most preferably, fluorescence in-situ hybridization (FISH or PNA-FISH) is the assay format. Exemplary methods for performing PNA-FISH can be found in: Thisted et al. Cell Vision, 3:358-363 (1996) or WIPO Patent Application WO97/18325, herein incorporated by reference.

Organisms which have been treated with the Linear Beacons of this invention can be detected by several exemplary methods. The cells can be fixed on slides and then visualized with a microscope or laser scanning device. Alternatively, the cells can be fixed and then analyzed in a flow cytometer (See for example: Lansdorp et al.; WIPO Patent Application; WO97/14026). Slide scanners and flow cytometers are particularly useful for rapidly quantitating the number of target organisms present in a sample of interest.

Because the method of this invention may be used in a probe-based hybridization assay, this invention will find utility in improving assays used to detect, identify of quantitate the presence or amount of an organism or virus in a sample through the detection of target sequences associated with the organism or virus. (See: U.S. Pat. No. 5,641,631, entitled "Method for detecting, identifying and quantitating organisms and viruses" herein incorporated by reference). Similarly, this invention will also find utility in an assay used in the detection, identification or quantitation of one or more species of an organism in a sample (See U.S. Pat. No. 5,288,611, entitled "Method for detecting, identifying and quantitating organisms and viruses" herein incorporated by reference). This invention will also find utility in an assay used to determine the effect of antimicrobial agents on the growth of one or more microorganisms in a sample (See: U.S. Pat. No. 5,612,183, entitled "Method for determining the effect of antimicrobial agents on growth using ribosomal nucleic acid subunit subsequence specific probes" herein incorporated by reference). This invention will also find utility in an assay used to determine the presence or amount of a taxonomic group of organisms in a sample (See: U.S. Pat. No. 5,601,984, entitled "Method for detecting the presence of amount of a taxonomic group of organisms using specific r-RNA subsequences as probes" herein incorporated by reference).

When performing the method of this invention, it may be preferable to use one or more unlabeled or independently detectable probes in the assay to thereby suppress the binding of the Linear Beacon to a non-target sequence. The presence of the "blocking probe(s)" helps to increase the discrimination of the assay and thereby improve reliability and sensitivity (signal to noise ratio).

In certain embodiments of this invention, one target sequence is immobilized to a surface by proper treatment of the sample. Immobilization of the nucleic acid can be easily accomplished by applying the sample to a membrane and then UV-crosslinking. For example, the samples may be arranged in an array so that the array can be sequentially interrogated with one or more Linear Beacons to thereby determine whether each sample contains one or more target sequence of interest.

In still another embodiment, the Linear Beacon is immobilized to a support and the samples are sequentially interrogated to thereby determine whether each sample contains a target sequence of interest. In preferred embodiments, the Linear Beacons are immobilized on an array which is contacted with the sample of interest. Consequently, the sample can be simultaneously analyzed for the presence and quantity of numerous target sequences of interest wherein the composition of the Linear Beacons are judiciously chosen and arranged at predetermined locations on the surface so that the presence, absence or amount of particular target sequences can be unambiguously determined. Arrays of Linear Beacons are particularly useful because no second detection system is required. Consequently, this invention is also directed to an array comprising two or more support bound Linear Beacons suitable for detecting, identifying or quantitating a target sequence of interest.

Kits:

In yet another embodiment, this invention is directed to kits suitable for performing an assay which detects the presence, absence or amount of one or more target sequence which may be present in a sample. The characteristics of Linear Beacons suitable for the detection, identification or quantitation of amount of one or more target sequence have been previously described herein. Furthermore, methods suitable for using the Linear Beacon components of a kit to detect, identify or quantitate one or more target sequence which may be present in a sample have also been previously described herein.

The kits of this invention comprise one or more Linear Beacons and other reagents or compositions which are selected to perform an assay or otherwise simplify the performance of an assay. Preferred kits contain sets of Linear Beacons, wherein each of at least two Linear Beacons of the set are used to distinctly detect and distinguish between the two or more different target sequences which may be present in the sample. Thus, the Linear Beacons of the set are preferably labeled with independently detectable moieties so that each of the two or more different target sequences can be individually detected, identified or quantitated (a multiplex assay).

Exemplary Applications for Using the Invention:

Whether support bound or in solution, the methods, kits and compositions of this invention are particularly useful for the rapid, sensitive, reliable and versatile detection of target sequences which are particular to organisms which might be found in food, beverages, water, pharmaceutical products, personal care products, dairy products or environmental samples. The analysis of preferred beverages include soda, bottled water, fruit juice, beer, wine or liquor products. Consequently, the methods, kits and compositions of this invention will be particularly useful for the analysis of raw materials, equipment, products or processes used to manufacture or store food, beverages, water, pharmaceutical products, personal care products, dairy products or environmental samples.

Whether support bound or in solution, the methods, kits and compositions of this invention are particularly useful for the rapid, sensitive, reliable and versatile detection of target sequences which are particular to organisms which might be found in clinical environments. Consequently, the methods, kits and compositions of this invention will be particularly useful for the analysis of clinical specimens or equipment, fixtures or products used to treat humans or animals. For example, the assay may be used to detect a target sequence which is specific for a genetically based disease or is specific for a predisposition to a genetically based disease. Non-limiting examples of diseases include, β-Thalassemia, sickle cell anemia, Factor-V Leiden, cystic fibrosis and cancer related targets such as p53, p10, BRC-1 and BRC-2.

In still another embodiment, the target sequence may be related to a chromosomal DNA, wherein the detection, identification or quantitation of the target sequence can be used in relation to forensic techniques such as prenatal screening, paternity testing, identity confirmation or crime investigation.

EXAMPLES

This invention is now illustrated by the following examples which are not intended to be limiting in any way.

Example 1

Synthesis of N-α-(Fmoc)-N-ε-(NH$_2$)-L-Lysine-OH

To 20 mmol of N-α-(Fmoc)-N-ε-(t-boc)-L-lysine-OH was added 60 mL of 2/1 dichloromethane (DCM)/trifluoroacetic acid (TFA). The solution was allowed to stir until the tert-butyloxycarbonyl (t-boc) group had completely been removed from the N-α-(Fmoc)-N-ε-(t-boc)-L-lysine-OH. The solution was then evaporated to dryness and the residue redissolved in 15 mL of DCM. An attempt was then made to precipitate the product by dropwise addition of the solution to 350 mL of ethyl ether. Because the product oiled out, the ethyl ether was decanted and the oil put under high vacuum to yield a white foam. The white foam was dissolved in 250 mL of water and the solution was neutralized to pH 4 by addition of saturated sodium phosphate (dibasic). A white solid formed and was collected by vacuum filtration. The product was dried in a vacuum oven at 35-40° C. overnight. Yield 17.6 mmol, 88%.

Example 2

Synthesis of N-α-(Fmoc)-N-ε-(dabcyl)-L-Lysine-OH

To 1 mmol of N-α-(Fmoc)-N-ε-(NH$_2$)-L-Lysine-OH (Example 1) was added 5 mL of N,N'-dimethylformamide (DMF) and 1.1 mmol of TFA. This solution was allowed to stir until the amino acid had completely dissolved.

To 1.1 mmol of 4-((4-(dimethylamino)phenyl)azo)benzoic acid, succinimidyl ester (Dabcyl-NHS; Molecular Probes, P/N D-2245) was added 4 mL of DMF and 5 mmol of diisopropylethylamine (DIEA). To this stirring solution was added, dropwise, the N-α-(Fmoc)-N-ε-(NH$_2$)-L-Lysine-OH solution prepared as described above. The reaction was allowed to stir overnight and was then worked up.

The solvent was vacuum evaporated and the residue partitioned in 50 mL of DCM and 50 mL of 10% aqueous citric acid. The layers were separated and the organic layer washed with aqueous sodium bicarbonate and again with 10% aqueous citric acid. The organic layer was then dried with sodium sulfate, filtered and evaporated to an orange foam. The foam was crystallized from acetonitrile (ACN) and the crystals collected by vacuum filtration. Yield 0.52 mmol, 52%.

Example 3

Synthesis of N-α-(Fmoc)-N-ε-(dabcyl)-L-Lysine-PAL-Peg/PS Synthesis Support

The N-α-(Fmoc)-N-ε-(dabcyl)-L-Lysine-OH (Example 2) was used to prepare a synthesis support useful for the preparation of C-terminal dabcylated PNAs. The fluorenylmethoxycarbonyl (Fmoc) group of 0.824 g of commercially available Fmoc-PAL-Peg-PS synthesis support (PerSeptive Biosystems, Inc.; P/N GEN913384) was removed by treatment, in a flow through vessel, with 20% piperidine in DCM for 30 minutes. The support was then washed with DCM. Finally, the support was washed with DMF and dried with a flushing stream of argon.

A solution containing 0.302 g N-α-(Fmoc)-N-ε-(dabcyl)-L-Lysine-OH, 3.25 mL of DMF, 0.173 g [O-(7-azabenzotriaol-1-yl)-1,1,3,3-tetramethyluronium hexafluorophosphate (HATU), 0.101 mL DIEA and 0.068 mL 2,6-lutidine was prepared by sequential combination of the reagents. This solution was then added to the washed synthesis support and allowed to react for 2 hours. The solution was then flushed through the vessel with a stream of argon and the support washed sequentially with DMF, DCM and DMF. The resin was then dried with a stream of argon.

The support was the treated with 5 mL of standard commercially available PNA capping reagent (PerSeptive Biosystems, Inc., P/N GEN063102). The capping reagent was then flushed from the vessel and the support was washed with DMF and DCM. The support was then dried with a stream of argon. Finally, the synthesis support was dried under high vacuum.

Final loading of the support was determined by analysis of Fmoc loading of three samples of approximately 6-8 mg. Analysis determined the loading to be approximately 0.145 mmol/g.

This synthesis support was packed into an empty PNA synthesis column, as needed, and used to prepare PNA oligomers having a C-terminal dabcyl quenching moiety attached to the PNA oligomer through the ε-amino group of the C-terminal L-lysine amino acid.

Example 4

Synthesis of PNA

PNAs were synthesized using commercially available reagents and instrumentation obtained from PerSeptive Biosystems, Inc. Double couplings were often performed to insure that the crude product was of acceptable purity. PNAs possessing a C-terminal dabcyl moiety were prepared by performing the synthesis using the dabcyl-lysine modified synthesis support prepared as described in Example 3 or by labeling the N-ε-amino group of the C-terminal lysine residue while the PNA was still support bound as described in Example 10. All PNAs possessing both an N-terminal fluorescein moiety, as well as, a C-terminal dabcyl moiety were treated with the appropriate labeling reagents and linkers (as required) prior to cleavage from the synthesis support. PNAs comprising an N-terminal Cy3 label (Amersham) were cleaved from the synthesis support and HPLC purified prior to Cy3 labeling (See: Example 12).

Example 5

Preferred Method for Removal of the Fmoc Protecting Group

The synthesis support was treated with a solution of 25% piperidine in DMF for 5-15 minutes at room temperature. After treatment, the synthesis support was washed and dried under high vacuum. The support was then treated with the appropriate labeling reagent and/or cleaved from the synthesis support.

Example 6

Synthesis of Fluorescein-O-Linker

To 7.5 mmol of N-(tert-butyloxycarbonyl)-8-amino-3,6-dioxaoctanoic acid stirring in 10 mL of DCM was added 50 mmol of TFA. The solution was stirred at room temperature until the t-boc group was completely removed. The solvent was then removed by vacuum evaporation and the product was then resuspended in 10 mL of DCM.

To this stirring solution was added, dropwise, a solution containing 7.5 mmol of Di-O-pivaloyl-5(6)-carboxyfluorescein-NHS ester, 30 mmol of N-methylmorpholine (NMM) and 20 mL of DCM. The reaction was allowed to run overnight and was then transferred to a separatory funnel in the morning.

This organic solution was washed with aqueous 10% citric acid two times and then dried with sodium sulfate, filtered and evaporated to a brown foam. The product was column purified using silica gel. A DCM mobile phase and stepwise methanol gradient was used to elute the product from the stationary phase. Yield 2.8 g of foam which was precipitated by dissolution in a minimal amount of DCM and dropwise addition of that solution to hexane. Yield 2.32 g white powder. The purity of the product was not suitable for labeling so an additional reversed phase chromatographic separation was performed on a sample of this material.

One gram of the precipitated product was dissolved in 30 mL of a 50 mM aqueous triethylammonium acetate (pH 7) containing 40% acetonitrile. This solution was then added to a pre-equilibrated 2 g Waters Sep-Pack Vac 12 cc tC18 cartridge (P/N WAT043380) in 10, 3 mL aliquots. After the addition of all loading solvent, two 3 mL aliquots of 50 mM aqueous triethylammonium acetate (pH 7) containing 40% acetonitrile was loaded as a first wash. Two 3 mL aliquots of 50 mM aqueous triethylammonium acetate (pH 7) containing 60% acetonitrile was then loaded as a second wash. Finally, a single 3 mL aliquot of acetonitrile was used to elute material remaining on the column. The eluent of each aliquot was collected individually and analyzed by HPLC for purity. The aliquots were vacuum evaporated and the mass of each determined. Fractions of suitable purity were redissolved in DCM, the fractions were combined and precipitated in hexane. Yield 0.232 g.

Example 7

General Procedure for N-Terminal Labeling of Support Bound PNA with Fluorescein-O-Linker For N-terminal fluorescein labeling, the amino terminal fluorenylmethoxycarbonyl (Fmoc) group of several of the fully assembled PNA oligomers was removed by piperidine treatment and the resin was washed and dried under vacuum. The resin was then treated for 20-30 minutes with approximately 300 μL of a solution containing 0.07 M Fluorescein-O-Linker, 0.06 M (HATU), 0.067 M DIEA and 0.1 M 2,6-lutidine. After treatment the resin was washed and dried under high vacuum. The PNA oligomer was then cleaved, deprotected and purified as described below.

Example 8

General Procedure for Labeling of Support Bound PNA with 5(6)carboxyfluorescein-NHS This method was used as an alternative to the procedure described in Example 7, for labeling PNAs with 5(6)-carboxyfluorescein. This procedure requires that the N-terminus of the PNA oligomer be reacted with Fmoc-8-amino-3,6-dioxaoctanoic acid prior to performing the labeling reaction so that equivalent PNA constructs are prepared. The amino terminal fluorenylmethoxycarbonyl (Fmoc) group of the fully assembled PNA oligomer was removed by piperidine treatment and the synthesis support was washed and dried under vacuum. The synthesis support was then treated for 4-5 hours at 37° C. with approximately 300 μL of a solution containing 0.1M 5(6)carboxyfluorescein-NHS (Molecular Probes, P/N C-1311), 0.3M DIEA and 0.3M 2,6-lutidine. After treatment the synthesis support was washed and dried under high vacuum. The PNA oligomer was then cleaved, deprotected and purified as described below.

More preferably, the synthesis support was then treated for 2-5 hours at 30-37° C. with approximately 250 μL of a solution containing 0.08M 5(6)carboxyfluorescein-NHS, 0.24M DIEA and 0.24M 2,6-lutidine.

Example 9

General Procedure for Labeling of Support Bound PNA with 5(6)carboxyfluorescein

After proper reaction with linkers and removal of the terminal amine protecting group, the resin was treated with 250 μL of a solution containing 0.5M 5(6)carboxyfluorescein, 0.5M N,N'-diisopropylcarbodiimide, 0.5M 1-hydroxy-7-azabenzotriazole (HOAt) in DMF (See: Weber et al., *Bioorganic & Medicinal Chemistry Letters,* 8: 597-600 (1998). After treatment the synthesis support was washed and dried under high vacuum. The PNA oligomer was then cleaved, deprotected and purified as described below.

Note on Fluorescein Labeling: The fluorescein labeled PNAs described herein were prepared using several different procedures. The different procedures have evolved to optimize fluorescein labeling conditions. At this time we prefer to use the procedure of Weber et al. for most fluorescein labeling operations.

Example 10

General Procedure for Dabcyl Labeling of the N-ϵ-amino Group of Support Bound L-Lysine This procedure was used as an alternative to using the prederivatized support when preparing dabcylated PNAs. This procedure has the advantage that the lysine moiety (and therefore the attached dabcyl moiety) may be placed at any location in the polymer including within the probing nucleobase sequence.

The resin (still in the synthesis column) was treated with 10 mL of a solution containing 1% trifluoroacetic acid, 5% triisopropylsilane (TIS) in dichloromethane by passing the solution through the column over a period of approximately 15 minutes. After treatment, the synthesis support was washed with DMF. Prior to treatment with labeling reagent the support was neutralized by treatment with approximately 10 mL of a solution containing 5% diisopropylethylamine in DMF. After treatment, the support was treated with Dabcyl-NHS (as a substitute for 5(6)carboxyfluorescein-NHS in the procedure) essentially as described in Example 8.

Note: This procedure was only performed on PNA prepared using Fmoc-PAL-PEG/PS (PerSeptive P/N GEN913384). It was not performed with the more acid labile Fmoc-XAL-PEG/PS (PerSeptive P/N GEN913394).

Example 11

General Procedure for Cleavage, Deprotection and Purification

The synthesis support (Fmoc-PAL-PEG/PS; P/N GEN913384) was removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1-3 hours. The solution was spun through the support bed and again the support was treated with a solution of TFA/m-cresol for 1-3 hours. The solution was again spun through the support bed. The combined eluents (TFA/m-cresol) were then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using reversed phase chromatographic methods.

Note: Several PNAs were prepared using new product Fmoc-XAL-PEG/PS synthesis support (P/N GEN 913394) available from PerSeptive Biosystems, Inc. This support has the advantage that the PNA can be removed more rapidly and under more mildly acid conditions. For PNAs prepared with Fmoc-XAL-PEG/PS the support was treated as described above except that a solution of TFA/m-cresol 9/1 was generally used for a period of 10-15 minutes (2x).

Example 12

Cy3 Labeling of PNAs

The purified amine containing PNA was dissolved in 1/1 DMF/water at a concentration of 0.05 OD/μL to prepare a stock PNA solution. From the stock, approximately 30 nmole of PNA was added to a tube. To this tube was then added 125 μL 0.1 M HEPES (pH 8.5), and enough 1/1 DMF/water to bring the total volume to 250 μL. This solution was thoroughly mixed. To a prepackaged tube of Cy3 dye (Amersham), was added the entire 250 μL solution prepared as described above. The tube was well mixed and then allowed to react for 1 hour at ambient temperature.

After reaction, the solvent was removed by evaporation in a speed-vac. The pellet was then dissolved in 400 μL of a solution containing 3:11% aqueous TFA/ACN. Optionally the solution was then transferred to a 5000 MW Ultrafree (Millipore, P/N UFC3LCC25) or a 3000 MW (Amicon, P/N 42404) filter to removed excess dye. The recovered product was then repurified using reversed phase chromatographic methods.

Experiment 13: Analysis and Purification Of PNA Oligomers

All PNA probes were analyzed and purified by reversed phase HPLC. Probe composition was confirmed by comparison with theoretical calculated masses.

HPLC Procedures:

Generally, two different high performance liquid chromatography (HPLC) gradients were used to analyze and purify the PNA oligomers (Gradients A & B). Preparative purifications were scaled based on the analytical analysis conditions described in Gradients A & B. Gradient B was developed because initial purification using standard gradients (Gradient A) proved to be less than satisfactory. The experimental conditions are as described below except that some attempts were made to improve purifications by the addition of 20% formamide to the running buffers during some of the purifications. This procedure was abandoned since it did not appear to produce any beneficial results. Curiously however, careful review of the data suggested that the HPLC artifacts previously thought to correlate with the structure of certain probes (See: Provisional Patent Application No. 60/063,283 filed on Oct. 27, 1997) was also found to correlate with the presence of formamide during the purification. Therefore, no correlation is now believed to exist between structure of the PNA probe and the HPLC profiles observed for the purified oligomers.

Gradients A & B

Buffer A=0.1% TFA in water.

Buffer B=0.1% TFA in acetonitrile.

Flow Rate: 0.2 mL/min.

Column Temperature: 60° C.

Instrument: Waters 2690 Alliance: Control by Waters Millennium Software

Stationary Phase: Waters Delta Pak C18, 300 Å, 5 μm, 2×150 mm (P/N WAT023650)

Detection at 260 nm

Gradient Profile A

| Time (min.) | Percent Buffer A | Percent Buffer B | Curve |
|---|---|---|---|
| 0.00 | 100 | 0 | 0 |
| 4.00 | 100 | 0 | 6 |
| 22.00 | 80 | 20 | 6 |
| 38.00 | 40 | 60 | 6 |
| 40.00 | 20 | 80 | 11 |

Gradient Profile B

| Time (min.) | Percent Buffer A | Percent Buffer B | Curve |
|---|---|---|---|
| 0.00 | 90 | 10 | 0 |
| 40.00 | 60 | 40 | 6 |
| 50.00 | 20 | 80 | 6 |

Mass Analysis:

Samples were analyzed using a linear Voyager Delayed Extraction Matrix Assisted Laser Desorption Ionization-Time Of Flight (DE MALDI-TOF) Mass spectrometer (Per-Septive Biosystems, Inc.). Sinipinic acid was used as the sample matrix and also used as one point for calibration of the mass axis. Bovine insulin was used as an internal calibration standard for the second calibration point of the mass axis.

Samples were generally prepared for analysis by first preparing a solution of sinipinic acid at a concentration of 10 mg/mL in a 1:2 mixture of acetonitrile and 0.1% aqueous trifluoroacetic acid. Next, an insulin solution was prepared by dissolving 1 mg of bovine insulin (Sigma) in 0.1% aqueous trifluoroacetic acid. Finally, an insulin/matrix solution was then prepared by mixing 9 parts of the sinipinic acid solution to 1 part of the bovine insulin solution. Samples were prepared for analysis by spotting 1 μL of the insulin/matrix solution followed by spotting 1 μL of diluted sample (approximately 0.1 to 1 OD per mL) onto the mass spectrometer target. The instrument target was allowed to dry before being inserted into the mass spectrometer.

Tables of PNA Oligomers Prepared for Study

TABLE 1A

Probes Prepared To Evaluate PNA Hairpins

| Probe Desc | CODE[1] | PNA Probe Sequence |
|---|---|---|
| N-terminal Arm Forming Segments | | |
| .001 | 5205 | Flu-O-TGG-AGO-OAC-GCC-ACC-AGC-TCC-AK(dabcyl)-NH$_2$ |
| .007 | 5105 | Flu-O-TGG-AGO-ACG-CCA-CCA-GCT-CCA-K(dabcyl)-NH$_2$ |
| .010 | 5005 | Flu-O-TGG-AGA-CGC-CAC-CAG-CTC-CAK(dabcyl)-NH$_2$ |
| .002 | 3203 | Flu-O-TGG-OOA-CGC-CAC-CAG-CTC-CAK(dabcyl)-NH$_2$ |
| .008 | 3103 | Flu-O-TGG-OAC-GCC-ACC-AGC-TCC-AK(dabcyl)-NH$_2$ |
| .009 | 4004[2] | Flu-O-TGG-ACG-CCA-CCA-GCT-CCA-K(dabcyl)-NH$_2$ |
| C-terminal Arm Forming Segments | | |
| .018 | 7027 | Flu-O-ACG-CCA-CCA-GCT-CCA-OO-GTG-GCG-T-K(dabcyl)-NH$_2$ |
| .011A | 5025 | Flu-O-ACG-CCA-CCA-GCT-CCA-OOG-GCG-TK(dabcyl)-NH$_2$ |
| .006 | 3023 | Flu-O-ACG-CCA-CCA-GCT-CCA-OOC-GTK(dabcyl)-NH$_2$ |
| Probing Sequence External to the Arm Sequences | | |
| .017 | 5115 | Flu-O-TAG-CAO-ACG-CCA-CCA-GCT-CCA-OTG-CTA-K(dabcyl)-NH$_2$ |
| .005 | 3113 | Flu-O-TAG-O-ACG-CCA-CCA-GCT-CCA-O-CTA-K(dabcyl)-NH$_2$ |
| Control Probes; No Arm Forming Segments | | |
| .003 | 0000 | Flu-O-ACG-CCA-CCA-GCT-CCA-K(dabcyl)-NH$_2$ |
| .004 | 0110 | Flu-OO-ACG-CCA-CCA-GCT-CCA-OK(dabcyl)-NH$_2$ |

1. The CODE is a simple means to determine the length of the complementary nucleobases at the amine and carboxyl termini of the PNA polymer and the number and location of any 8-amino-3,6-dioxaoctanoic acid flexible linker units. The probing nucleobase sequence is the same for all probes listed in the table. The first digit in the CODE represents the length of the N-terminal arm segment which is complementary to the C-terminal arm segment. The second digit in the CODE represents the number of flexible linker units which link the N-terminal arm to the probing nucleobase sequence. The third digit in the CODE represents the number of flexible linker units which link the C-terminal arm to the probing nucleobase sequence. The fourth digit in the CODE represents the length of the C-terminal arm segment which is complementary to the N-terminal arm segment. Consequently, the CODE can be used to visually compare the general structure of the different PNA oligomers listed in Table 1.

2. A coincidental, 4 bp. overlap between the nucleobases at the amine and carboxyl termini are present in this construct instead of the directly comparable 3 bp. overlap.

TABLE 1B

Linear Beacons Prepared To Examine Properties

| Probe Desc. | PNA Probe Sequence |
|---|---|
| PNA003.11 (mer) | Flu-O-GCC-ACC-AGC-TC-K(dabcyl)-NH$_2$ |
| PNA003.13 (mer) | Flu-O-CGC-CAC-CAG-CTC-C-K(dabcyl)-NH$_2$ |
| PNA003.15 (mer) | Flu-O-ACG-CCA-CCA-GCT-CCA-K(dabcyl)-NH$_2$ |
| PNA003.17 (mer) | Flu-O-TAC-GCC-ACC-AGC-TCC-AA-K(dabcyl)-NH$_2$ |
| PNA003.MU | Flu-O-ACG-CCA-CAA-GCT-CCA-K(dabcyl)-NH$_2$ |
| Cy3PNA003.15 (mer) | Cy3-O-ACG-CCA-CCA-GCT-CCA-K(dabcyl)-NH$_2$ |
| Cy3SCBL03-15 | Cy3-O-CCA-GCA-TCA-CCA-GAC-K(dabcyl)-NH$_2$ |

TABLE 1C

Linear Beacons Prepared To Evaluate PNA-FISH Assays

| Probe Desc. | Target Organism | PNA Probe Sequence |
|---|---|---|
| Pse16S32 | *Pseudomonas* | Flu-O-CTG-AAT-CCA-GGA-GCA-K(dabcyl)-NH$_2$ |
| Pse16S34 | *Pseudomonas* | Flu-O-AAC-TTG-CTG-AAC-CAC-K(dabcyl)-NH$_2$ |
| Bac16S19 | *Bacillus* | Flu-O-CTT-TGT-TCT-GTC-CAT-K(dabcyl)-NH$_2$ |

For Tables 1A, 1B and 1C, all PNA sequences are written from the amine to the carboxyl terminus. Abbreviations are: Flu=5-(6)-carboxyfluorescein, dabcyl=4-((4-(dimethylamino)phenyl)azo)benzoic acid, O=8-amino-3,6-dioxaoctanoic acid; K=the amino acid L-Lysine and Cy3 is the cyanine 3 dye available from Amersham.

Example 14

Synthesis of DNA Oligonucleotides for Study

For this study, biotin labeled DNA oligonucleotides suitable as nucleic acids comprising a target sequence which are complementary to the PNA probing sequence of the k-ras PNA probes were either synthesized using commercially available reagents and instrumentation or obtained from commercial vendors. Additionally, DNA oligomers of equivalent nucleobase length and labeling configuration as compared with several Linear Beacons were prepared using the dabcyl synthesis support available from Glen Research (P/N 20-5911) and other commercially available DNA reagents and instrumentation. The 5(6)carboxyfluorescein labeling of all DNAs was obtained using Fluoredite phosphoramidite (PerSeptive Biosystems, Inc., P/N GEN080110) All DNAs were purified by conventional methods. The sequences of the DNA oligonucleotides prepared are illustrated in Tables 2A and 2B. Methods and compositions for the synthesis and purification of synthetic DNAs are well known to those of ordinary skill in the art.

TABLE 2A

DNA Targets

| Description | Target DNA Sequence |
|---|---|
| wt k-ras2 | Biotin-GTG-GTA-GTT-GGA-GCT-GGT-GGC-GTA-GGC-AAG-A<br>Seq. Id. No. 1 |
| SCBL-DNA | GGT-AGT-GTC-TGG-TGA-TGC-TGG-AGG-CAA<br>Seq. Id. No. 2 |

The nucleic acid target is illustrated from the 5' to 3' terminus.

TABLE 2B

DNAs of Equivalent Subunit Length To Linear Beacons

| Description | DNA Probe Sequence |
|---|---|
| DNA003-11 (mer) | Flu-G-CCA-CCA-GCT-C-dabcyl<br>Seq. Id. No. 3 |
| DNA003-13 (mer) | Flu-CG-CCA-CCA-GCT-CC-dabcyl<br>Seq. Id. No. 4 |
| DNA003-15 (mer) | Flu-ACG-CCA-CCA-GCT-CCA-dabcyl<br>Seq. Id. No. 5 |
| DNA003-17 (mer) | Flu-TA-CGC-CAC-CAG-CTC-CAA--dabcyl<br>Seq. Id. No. 6 |

Detailed Structural Analysis of PNA Oligomers Prepared for PNA Molecular Beacon Study

Example 15

Analysis of Fluorescent Thermal Profiles

General Experimental Procedure:

Fluorescent measurements were taken using a RF-5000 spectrofluorophotometer (Shimadzu) fitted with a water jacketed cell holder (P/N 206-15439, Shimadzu) using a 1.6 mL, 10 mm path length cuvet (Stama Cells, Inc.). Cuvet temperature was modulated using a circulating water bath (Neslab). The temperature of the cuvet contents was monitored directly using a thermocouple probe (Bamant; model No. 600-0000) which was inserted below liquid level by passing the probe tip through the cap on the cuvet (custom manufacture).

Stock solution of HPLC purified PNA oligomer was prepared by dissolving the PNA in 50% aqueous N,N'-dimethylformamide (DMF). From each PNA stock was prepared a solution of PNA oligomer, each at a concentration of 10 pmol in 1.6 mL of Hyb. Buffer (50 mM Tris. HCl pH 8.3 and 100 mM NaCl) by serial dilution of purified PNA stock with Hyb. Buffer. Samples were exited at 493 nm and the fluorescence measured at 521 nm. Data points were collected at numerous temperatures as the cuvet was heated and then again measured as the cuvet was allowed to cool. Generally, the bath temperature was sequentially increased by 5° C. and then allowed to equilibrate before each data point was recorded. Similarly, to generate the cooling profile, the bath temperature was sequentially decreased by 5° C. and then allowed to equilibrate before each data point was recorded.

Data Discussion:

Nucleic acid Molecular Beacons which form a hairpin structure are expected to exhibit an increase in fluorescent intensity when heated which is consistent with the melting of the hairpin stem and the physical transition of the probe stem from a helix to a random coil. Consistent with any nucleic acid melting event, the process is expected to be reversible thereby resulting in a decrease in fluorescence upon cooling of the sample caused by the resulting reformation of the helical structure. The expected melting phenomenon is documented for nucleic acid Molecular Beacons described by Tyagi et al. (See: Tyagi et al. *Nature Biotechnology*, 14: 303-308 (1996) at FIG. 3).

The results of the fluorescent thermal melting analysis of the PNA oligomers are summarized in the data presented in Table 3 and presented graphically in FIGS. 1A, 1B1, 1B2, 1B3 and 1C. With reference to Table 3, there are three different general Thermal Profiles observed for the different constructs and under the conditions examined. These are represented in Table 3 as Types A, B and C.

Fluorescent Thermal Profile Type A is characterized by a an increase in fluorescence intensity upon heating (melting) and a correlating decrease in fluorescence intensity upon cooling (reannealing). These results are similar to those published for nucleic acid Molecular Beacons which form a loop and hairpin stem structure. Thus, a Type A Fluorescent Thermal Profile is consistent with the formation of a stable hairpin stem and loop structure. This phenomenon is, therefore, believed to be caused by the melting and reannealing of a stem and loop structure in the PNA Molecular Beacon. However, applicants only claim that a Type A Fluorescent Thermal Profile is indicative of fairly reversible fluorescence quenching, as other structures may be responsible for the observed phenomenon.

Representatives of Type A Fluorescent Thermal Profiles are illustrated in FIG. 1A. The data presented in the Figure is for the PNA oligomers 0.001, 0.007 and 0.002. Data for both the melting (open character) and the reannealing (solid character) is presented. The sigmoidal transitions are consistent with a melting a reannealing of a duplex.

Fluorescent Thermal Profile Type B is characterized by an increase in fluorescence intensity upon heating (melting), but, no substantial correlating decrease in fluorescence intensity upon cooling of the sample. Thus, under the conditions examined, the interactions which initially cause the quenching of fluorescence do not appear to be readily reversible. Consequently, the data suggests that a PNA oligomer exhibiting a Type B Fluorescent Thermal Profile, does not exhibit all the features of a True Molecular Beacon. Nonetheless, as seen by the hybridization assay data, a Type B Fluorescent Thermal Profile does not prohibit the PNA oligomer from functioning as a PNA Beacon.

Representatives of Type B Fluorescent Thermal Profiles are illustrated in FIGS. 1B1, 1B2 and 1B3. The data is presented in three sets so that each trace may be more clearly viewed. The data presented in the Figures are for the PNA oligomers 0.010, 0.008, 0.009 (FIG. 1B1), 0.018, 0.011A, 0.017, (FIG. 1B2), and 0.003 and 0.004, (FIG. 1B3). Data for both the melting (open character) and the reannealing (solid character) is presented.

Fluorescent Thermal Profile Type C is characterized by a high initial fluorescent intensity which initially decreases with heating and again decreases even further upon cooling of the sample. The high initial fluorescent intensity suggests that this construct does not exhibit the initial fluorescence quenching observed with most of the other PNA constructs examined. The constant decrease in fluorescent intensity upon cooling is not well understood. Nevertheless, as seen by the hybridization assay data, a Type C, Fluorescent Thermal Profile does not prohibit the PNA oligomer from functioning as a PNA Beacon.

Figure 1C:
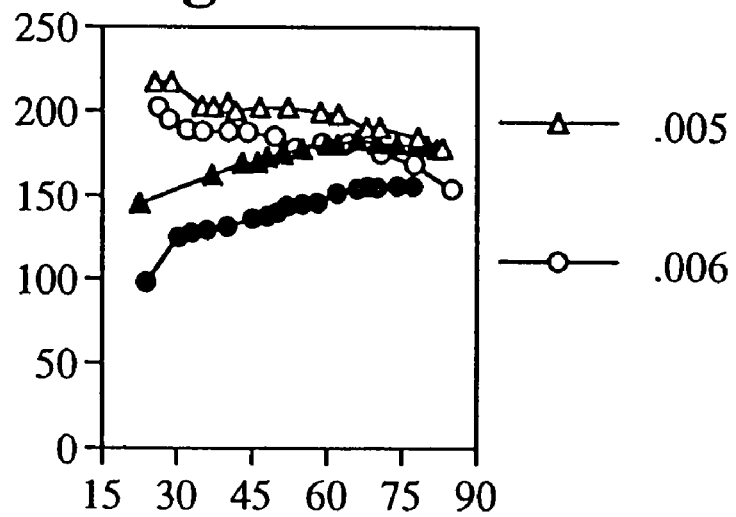
FIG. 1C is a graphical illustration of fluorescence vs. temperature data for PNA probes which exhibit a Type C Fluorescent Thermal Profile.

Representatives of Type C Thermal Profiles are illustrated in FIG. 1C. The data presented in the FIG. 1C is for the PNA oligomers 0.005 and 0.006. Data for both the melting (open character) and the reannealing (solid character) is presented.

TABLE 3

Summary of Data Compiled In Experiments 15-16

| Probe No. | CODE | Fluorescent Thermal Profile Observed | Hybridization Profile Observed |
|---|---|---|---|
| *N-terminal Arm Forming Segments* | | | |
| .001 | 5205 | A | A |
| .007 | 5105 | A | A |
| .010 | 5005 | B | A |
| .002 | 3203 | A | A |
| .008 | 3103 | B | A |
| .009 | 4004 | B | A |
| *C-terminal Arm Forming Segments* | | | |
| .018 | 7027 | B | A, B |
| .011A | 5025 | B | A |
| .006 | 3023 | C | C |
| *Probing Sequence External To Arm Segments* | | | |
| .017 | 5115 | B | B |
| .005 | 3113 | C | C |
| *Control Probes: No Arm Forming Segments* | | | |
| .003 | 0000 | B | B |
| .004 | 0110 | B | B |

Example 16

Analysis of Hybridization Assay Data

General Experimental Procedures:

All hybridization assay data was collected using a Wallac 1420 VICTOR equipped with a F485 CW-lamp filter and a F535 Emission filter. The NUNC MaxiSorp, breakapart microtitre plate was used as the reaction vessel. Each microtitre plate was prewashed with Hyb. Buffer at room temperature for 15 minutes before the reaction components were added. Total reaction volume was 100 µL in Hyb. Buffer.

Stock solution of purified PNA probe was prepared by dissolving the PNA in 50% aqueous N,N'-dimethylformamide (DMF). From this PNA Stock was prepared a solution of each PNA at a concentration of 25 pmole/1 µL by serial dilution of the PNA Stock with 50% aqueous DMF.

Stock solution of purified wt k-ras2 DNA was prepared by dissolving the purified DNA in TE (10 mM Tris. HCl pH 8.0; 1.0 mM EDTA, Sigma Chemical). From this DNA Stock was prepared a solution of wt k-ras2 DNA at a concentration of 100 pmol/99 µL by serial dilution of the DNA Stock with Hyb. Buffer.

Each reaction sample used for analysis was prepared by combining 1 µL of the appropriate PNA oligomer (25 pmole/µL) with either of 99 µL of wt k-ras2 DNA stock or 99 µL of Hyb. Buffer (control) as needed to prepare 100 µL of sample.

Samples were mixed and then fluorescence intensity monitored with time using the Wallac VICTOR instrument. Samples were run in triplicate to insure reproducible results. Data was acquired for 20-25 minutes after the reactants were mixed and then the wells were sealed and the plate heated to 42-50° C. in an incubator for 30-40 minutes. After cooling to ambient temperature, the wells were unsealed and then another 10 data points were collected over approximately five minutes.

Data Discussion:

Nucleic acid Molecular Beacons which form a hairpin stem and loop structure are expected to exhibit an increase in fluorescent intensity upon hybridization of the probing sequence to complementary nucleic acid. The expected increase in fluorescent intensity is documented for DNA Molecular Beacons described by Tyagi et al. (See: Tyagi et al. *Nature Biotechnology*, 14: 303-308 (1996)).

The results of the hybridization analysis of the PNA oligomers are summarized in Table 3 and presented graphically in FIGS. 2A1, 2A2, 2A3, 2B and 2C. With reference to Table 3, there are three different general Hybridization Profiles observed for the different constructs examined. These are represented in Table 3 as Types A, B and C. In FIG. 8, the signal to noise ratio (before and after heating) for all probes examined are graphically illustrated with the absolute values also presented below the Figure.

Hybridization Profile Type A is characterized by the increase in fluorescence intensity in samples containing complementary target DNA as compared with samples containing only the PNA oligomer. After heating, the fluorescent intensity of samples containing target sequence increases but the background fluorescence of the control sample(s) does not significantly change. Because the PNAs possess a very low inherent fluorescence, the probes which exhibit a Type A, Hybridization Profile generally have the highest signal to noise ratios. Representatives of Type A Hybridization Profiles are illustrated in FIGS. 2A1, 2A2 and 2A3. The data is presented in two separate graphical illustrations to clarify the presentation. The data presented in the Figures is for the PNA oligomers 0.001, 0.007, 0.010 (FIG. 2A1), 0.002, 0.008, 0.009 (FIG. 2A2), and 0.011A, 017 and 0.018 (FIG. 2A3).

Hybridization Profile Type B is characterized by the very rapid increase in fluorescence intensity in samples containing complementary target DNA as compared with samples containing only the PNA oligomer. The fluorescence intensity quickly reaches a plateau which does not significantly change (if at all) after heating. The background fluorescence of the control sample(s) does not change significantly even after heating. This suggest that the hybridization event rapidly, and with little resistance, reaches a binding equilibrium without any requirement for heating. Representatives of Type B Hybridization Profiles are illustrated in FIG. 2B. The data presented in FIG. 2B is for the PNA oligomers 0.018, 0.003 and 0.004 though PNA oligomer 0.018 does not exhibit all the characteristics of a Type B Hybridization Profile. Specifically, the signal for probe 0.018 does not appear to increase after heating (Type B) but the hybridization kinetics appear to be more like a Type A Hybridization Profile.

Control probes 0.003 and 0.004 (herein referred to as Linear Beacons) exhibit a Type B Hybridization Profile. Thus, the rapid hybridization kinetics of the Type B Hybridization Profile is probably the result of having no hairpin stem, or any other strong force, which can stabilize the non fluorescent polymer form. Nonetheless, the dynamic range (signal to noise ratio) observed in the hybridization assay of these probes is typically quite high and suggests that forces other than the hydrogen bonding of complementary nucleobases of arm segments can stabilize the interactions between the donor and acceptor moieties. Applicants have observed that label/label interactions can be quite strong and may be an important factor in this surprising result.

Though the background (noise) is higher for the 0.003 and 0.004 probes, as compared with the 0.001, 0.002, 0.007, 0.009 and 0.010 probes, the fluorescence intensity after hybridization is higher than that observed in any probes yet examined. As a result of the higher background, PNA oligomers 0.003 and 0.004 have a very favorable signal to noise ratio. This S/N ratio is nearly as favorable as any (and better than some) of the other PNA oligomers examined whether or not they possess arm segments. The data demonstrates that it is not necessary to have arm forming segments to create a probe which exhibits an initial low fluorescence intensity and a corresponding increase in fluorescence signal upon the binding of the probe to a target sequence.

Figure 2C:
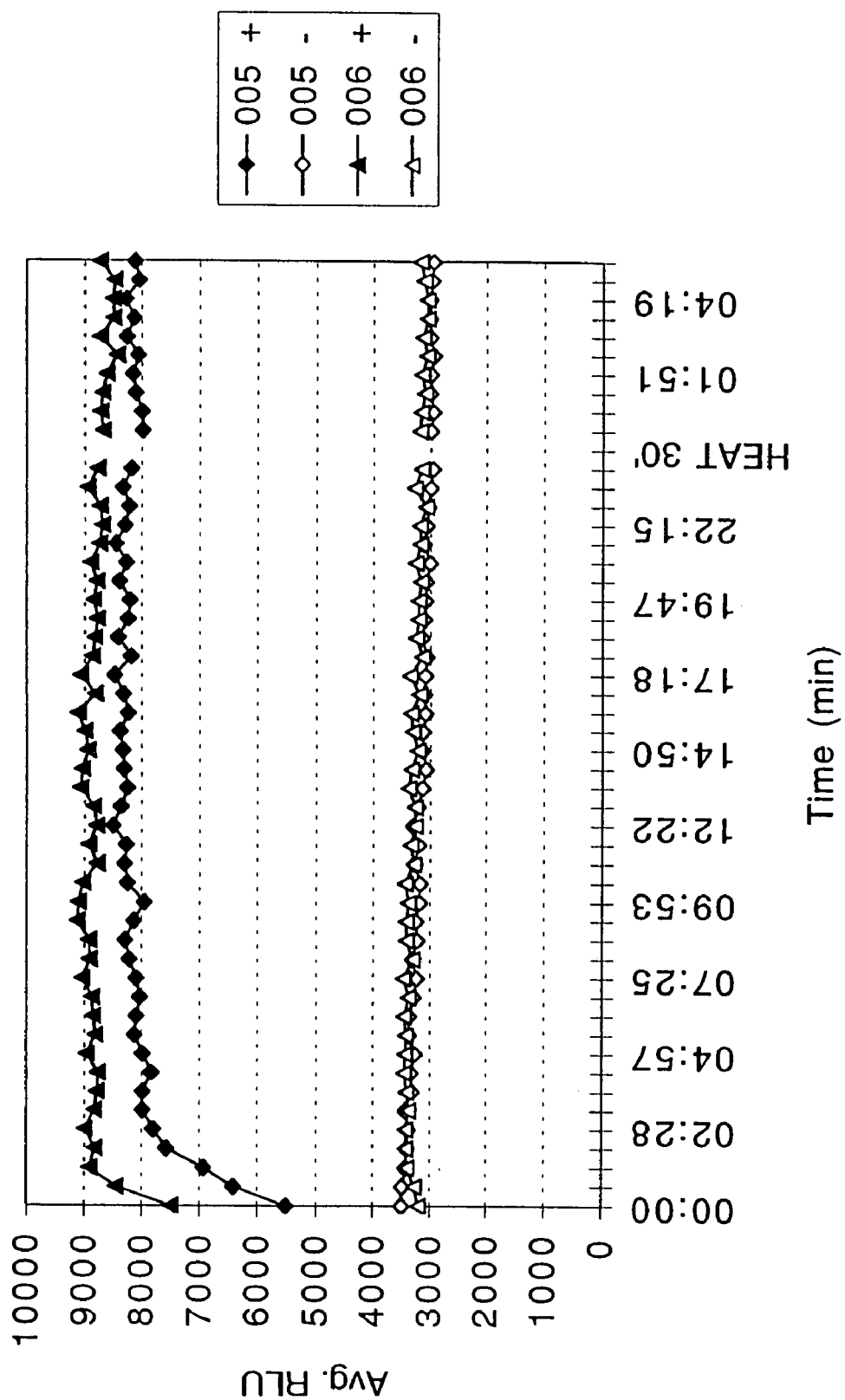
FIG. 2C is a graphical illustration of fluorescence vs. time data for PNA probes which exhibit a Type C Hybridization Profile.

Hybridization Profile C is characterized by a moderate increase in fluorescence intensity in samples containing target DNA as compared with samples containing only the PNA oligomer. The fluorescence intensity quickly reaches a plateau which does not significantly change (if at all) after heating. The background fluorescence of the control sample(s) is relatively high but does not change significantly even after heating. Hybridization Profiles B and C differ primarily because the background fluorescence in the control samples, containing no target nucleic acid, are dramatically higher in Hybridization Profile Type C. The hybridization data obtained for samples containing complementary nucleic acid, suggests that the hybridization event rapidly, and with little resistance, reaches equilibrium. However, the very high background signal suggests that the forces which should hold the donor and acceptor moieties in close proximity are not strong enough in these constructs to effectively quench the fluorescent signal. As a consequence of the moderate increase in fluorescence upon binding to the target sequence and the higher than usual intrinsic fluorescence a PNA Molecular Beacon, which exhibits a Type C Hybridization Profile, has a very low signal to noise ratio. Representatives of Type C Hybridization Profiles are illustrated in FIG. 2C. The data presented in FIG. 2C is for the PNA oligomers 0.006 and 0.005, respectively.

Summary of the Data Presented in Examples 15-16

The most surprising result of all the experiments performed by applicants is that all of the PNA oligomers examined, including the control probes 0.003 and 0.004, which have no arm forming segments, exhibit a correlation between increased fluorescence intensity and binding of the probe to target sequence.

Thus, it is not critical to design PNAs to possess arm forming segments to thereby achieve constructs which possess a very low intrinsic fluorescence, but which become highly fluorescent upon hybridization to target sequence. This is a very surprising result in light of the teachings related to nucleic acid Molecular Beacons. Therefore, the Linear Beacons of this invention can be used to detect, identify or quantitate target sequences without any requirement that excess probes be separated from the probe/target sequence complex prior to detection.

Example 17

Correlation of Linear Beacon Length with Noise (Background Fluorescence)

For this Example both DNA and PNA probes were compared to determine what effect variations in length would have on the noise (baseline or background fluorescence) of native probe. Comparisons were made with respect to changes in ionic strength (and minor change in pH), changes in the nature of the donor/acceptor pair and the presence or absence of magnesium.

Materials and Methods:

PNA probes PNA003-11, PNA003-13, PNA003-15, PNA003-17 and Cy3PNA003-0.15 (See: Table 1B) and DNA probes DNA003-11, DNA003-13, DNA003-15 and DNA003-17 (See: Table 2B) were prepared as described. The purified probes were diluted in TE Buffer (10 mM Tris-HCl pH 8.3, 1 mM EDTA) to a concentration of 25 pmole/μL and then diluted to 25 pmole/1.6 mL with one of either Buffer A, B or C. Samples of the probes were prepared in triplicate and each 1.6 mL sample was analyzed using a Shimadzu RF-5000 spectrofluorophotometer and a cell having a 10 mm path length. For fluorescein labeled oligomers, the excitation wavelength was set at 493 nm and the data was recorded for emission at 520 nm. For Cy3 labeled oligomers, the excitation wavelength was set at 545 nm and the data was recorded for emission at 560 nm. All data collected is recorded in relative light units (RLU).

The background of each probe was examined in each of Buffers A, B and C. The results of the triplicate analyses were averaged and the data obtained is graphically illustrated in FIG. 3 with the absolute value for the average RLU presented at the top of each bar. With reference to FIG. 3, the data is grouped into Buffers A, B and C for each probe examined. With the exception of the Cy3PNA003-15 probe, all PNAs were labeled at the N-terminus with 5(6)-carboxyfluorescein and at the C-terminus with dabcyl. The Cy3PNA003-15 probe differed from PNA003-15 in that Cy3 had been substituted for 5(6)-carboxyfluorescein. All DNAs were labeled at the 5'-terminus with 5(6)-carboxyfluorescein and at the 3'-terminus with a dabcyl. Given the commercially available chemistries, attempts were made to insure that label types and label spacing of the DNA and PNA probes were as comparable as reasonably possible.

| Buffer Compositions: | |
| --- | --- |
| Buffer A: | 10 mM Sodium Phosphate, pH 7.0, 5 mM $MgCl_2$. |
| Buffer B: | 10 mM Sodium Phosphate, pH 7.0. |
| Buffer C: | 50 mM Tris-Cl pH 8.3, 100 mM NaCl. |

Results and Discussion:

With reference to FIG. 3, the data for the fluorescein/dabcyl labeled DNA probes of 11, 13, 15 and 17 subunits in length are presented on the left. From a cursory review of data there is a clear correlation between length of the DNA oligonucleotide and the amount of noise (background). Specifically and without regard to the nature of the buffer, the noise increased substantially with each increase of two subunits of the DNA oligomer. This observation compares well with the reports of Mayrand et al. (See: U.S. Pat. No. 5,691,146, col. 7, lns. 8-24), Mathies et al. (See: U.S. Pat. No. 5,707,804 at col. 7, lns. 21-25) and Nazarenko et al. (See: *Nucl. Acids Res.* 25: at p. 2516, col. 2, lns. 36-40).

Regarding specific buffer effects, for all DNA oligomers, the noise observed in Buffer A was substantially lower than observed when the probe was in buffers B or C. Since Buffers A and B are of comparable ionic strength, clearly the presence of magnesium in Buffer A substantially reduced the noise of all probes. Though Buffers B and C were substantially different in ionic strength and marginally different in pH, only a small increase in noise was observed with the change from Buffer B to Buffer C. This change is more likely the result of the pH increase since fluorescein will have a higher quantum yield at the higher pH. Consequently, very little of the increase in noise which was observed between Buffers B and C is likely due to the increase in ionic strength.

In summary, magnesium content and oligomer length appear to have a substantial affect on noise (background fluorescence) of DNA probes whereas variations in the ionic strength of the probe environment appears to exhibit a lesser influence on noise.

With reference to FIG. 3, the data for the labeled PNA probes of 11, 13, 15 and 17 subunits in length are presented on the right. From a cursory review of data there much less of a difference between the noise (background) observed for the probes of different length. Moreover, unlike DNA, there is no clear correlation between probe length and noise intensity.

Regarding specific buffer effects, most dramatic of all was the consistency of background irrespective of the nature of the buffer. Though there were minor differences, the absolute difference in noise (background fluorescence) measured in each of the three buffers was remarkably small as compared with the DNA probes. Consequently, the noise of PNA probes was found to be fairly independent of the length of the probe, the presence or absence of magnesium and the ionic strength of the buffer. Again, the small increase in noise between Buffers B and C is likely a pH effect.

The data for the PNA probe, Cy3PNA003-15 can be most effectively compared with the data for PNA probe, PNA003-15, since only the donor fluorophores (Fluorescein to Cy3) differ. Though intensity of noise (background) cannot be directly correlated since the emission and excitation wavelengths used to examine the fluorescein and Cy3 dyes are substantially different, for this Linear Beacon there is almost no relative difference in noise in each of the three buffers examined. Most notably, there is no substantial difference between the data for Buffers B and C. This supports the argument that the increases in noise observed for the fluorescein probes is most likely a pH effect since the quantum yield of Cy3 should be less affected by the small differences in pH. Furthermore, since optimal excitation and emission wavelength for both the fluorescein and Cy3 fluorophores were used for examination, the comparatively low backgrounds for the Linear Beacons under fluorophore optimized conditions indicates that substantial quenching of fluorescence occurs for both probes without regard to the nature of the spectral properties of the donor fluorophore and acceptor quencher. Taken as a whole the data indicates that the noise of the PNA probes are substantially independent of probe length, ionic strength, presence or absence of magnesium and the spectral properties of the Beacon Set.

In summary, for PNA probes, the noise is substantially independent of the presence or absence of magnesium, oligomer length and ionic strength as compared with DNA probes having the most similar length and labeling configuration. Linear Beacons also possess the unusual property that energy transfer can occurs without regard to the nature of the spectral properties of the Beacon Set thereby indicating that the energy transfer likely occurs primarily by contact and not through FRET. Nevertheless, this data demonstrates a clear distinction in the structure and function between the PNA probes and the DNA probes examined.

Example 18

Correlation of Linear Beacon Length With Signal to Noise in a Hybridization Assay For this Example both DNA and PNA probes were compared to determine what effect variations in length would have on the signal to noise ratio of the native probe wherein the signal to noise ratio is derived from the signal generated in the presence of target sequence as compared with the noise or background fluorescent of the probe in the absence of target sequence. Comparisons were made with respect to changes in probe length, ionic strength, changes in the nature of the donor/acceptor pair and the presence or absence of magnesium. On a practical level, this data differs from that presented in Example 17 since it compares relative performance of the probes in a hybridization assay. For brevity, only the data for the 11-mer and 15-mer DNAs and PNAs is presented.

Materials and Methods:

PNA probes PNA003-11, PNA003-15, Cy3PNA003-15 (See: Table 1B) and DNA probes DNA003-11 and DNA003-15 (See: Table 2B) were prepared as described. The purified probes were diluted in TE Buffer (10 mM Tris-HCl pH 8.3, 1 mM EDTA) to a concentration of 25 pmole/µL and then this stock was further diluted to 25 pmole/50 µL with one of either Buffer A, B or C. The composition of Buffers A, B and C are described in Example 17. Samples of 50 µL of each probe in the appropriate Buffer was placed in each of six wells in a microtitre plate such that for each probe, three hybridization reactions and three negative control reactions (used to measure the noise or background fluorescence) were performed. For each of the hybridization reactions, 50 µL of target DNA (wt k-ras, Table 2A), which had been prepared by dilution of the target DNA in TE buffer to 100 pmole/µL and subsequent dilution of this stock to 25 pmole/µL with each of Buffers A, B or C, was added to each reaction. For each control, 50 µL of one of Buffers A, B or C was added. As a consequence of the time necessary to pipette and mix the contents of the wells, all reagents had been mixed for approximately 1 minute prior to the first fluorescence reading. All hybridization reactions were performed at ambient temperature.

Hybridization data was collected using a Wallac 1420 Victor multilabel counter. The fluorescent intensity of each well was measured for 0.1 second. For all samples, 40 measurements were taken over a period of approximately 30 minutes. Consequently, the time dependence of the signal to noise ratios were derived from the data collected over the 30 minute period. Signal to noise ratios derived from the average of the three hybridization reactions, as compared with the control reactions, is presented for: 1) the DNA and PNA 11-mers in FIGS. 4A and 4B: 2). the DNA and PNA 15-mers in FIGS. 4C and 4D: and 3). the 15-mer PNA probe Cy3PNA003-15 in FIG. 4E.

Results and Discussion:

With reference to FIG. 4A, signal to noise ratio for the 30 minutes of data collected for the DNA 11 mer in each of Buffers A, B and C is presented. Since a signal to noise ratio of 1 indicates no signal, the most striking result is the absence of any signal when Buffer B is used. By comparison the addition of magnesium (Buffer A) or the increase in ionic strength and pH (Buffer C) results in a substantial improvement in signal to noise. Furthermore, the rate of increase in signal to noise over time is quite distinct and can be used to monitor hybridization rate kinetics.

The signal to noise ratio obtained for the PNA 11-mer in all buffers is graphically presented in FIG. 4B. By comparison to the DNA 11-mer, a signal to noise ratio of greater than one was obtained under all conditions examined. Moreover, there was less of a dynamic range in the signal to noise ratio for each of the three buffers examined (the range of S/N for the DNA 11-mer at 30 minutes was about 1 to 14 whereas the range of S/N for the PNA 11-mer at 30 minutes was about 3 to 6). Consequently, the signal to noise ratio for the PNA 11-mer, as compared with the DNA 11-mer, appears to be fairly independent of ionic strength of its environment though there is at least some increase attributable to the change between Buffers B and C. Moreover, the signal to noise ratio of the PNA 11-mer appears to be completely independent of the presence or absence of magnesium since the data for Buffers A and B is essentially the same.

Additionally, there is very little increase in signal to noise ratio for the PNA 11-mer over time. Consequently, the data suggests that the hybridization kinetics of the Linear Beacon, PNA003.11, are extremely rapid in all Buffers examined and that the hybridization has nearly reached equilibrium within the first few minutes of the reaction.

With reference to FIGS. 4C and 4D, data for the DNA and PNA 15-mers, respectively, is graphically illustrated. Generally, all the data obtained for the 15-mers parallels that observed for the 11-mers. Specifically, the signal to noise ratio for the DNA 15-mer in Buffer B is 1, thereby indicating that no hybridization is detected within the bounds of the experiment. In Buffers A and C, the DNA 15-mer yields a signal to noise ratio which increases with time such that the kinetics of hybridization can be determined by analysis the data. Additionally, the dynamic range of the signal to noise ratio for the DNA 15-mer in Buffer A and C is between 6 and 11 as compared to the PNA 15-mer wherein the signal to noise ratio is about 7 to 13.

Taken as a whole the data demonstrates that the signal to noise ratio of the PNA 15 mer is fairly independent of the presence or absence of magnesium as the data is essentially the same for Buffers A and B. Furthermore, the signal to noise ratio for the PNA 15-mer, as compared with the DNA 15-mer, appears to be fairly independent of ionic strength of its environment though there is at least some increase attributable to the change between Buffers B and C. Finally, the data suggests that the hybridization kinetics of the Linear Beacon, PNA003-15, are extremely rapid in all Buffers examined as the hybridization has nearly reached equilibrium within the first few minutes of the reaction as compared with the hybridization kinetics of the DNA 15-mer which are substantially slower.

With reference to FIG. 4E, the signal to noise data for the Cy3 labeled PNA 15-mer, Cy3PNA003-15, is presented. The data for this probe can be most effectively compared with the data for PNA probe, PNA003-15, since only the donor fluorophore (Fluorescein to Cy3) has been altered. A cursory review of the data indicates that again, a positive signal to noise ratio is obtained in all three Buffers. The dynamic range of the signal to noise ratio is about 6 to 11 which compares well with the data for PNA003-15 thereby indicating that there is not a substantial dependence on the presence or absence of magnesium or a substantial dependence on ionic strength. Furthermore, the data clearly demonstrates that no substantial overlap between the emission of the donor moiety and the absorbance of the acceptor moiety is required in a Linear Beacon since the signal to noise ratio is essentially the same for both PNA003-15 and Cy3PNA003-15 despite the very different spectral characteristics of the fluorescein or Cy3 donor moieties of the donor/acceptor pairs (Beacon Set).

Curiously however, for the PNA probe Cy3PNA003-15, Buffers A and B outperform Buffer C. This result is substantially different than that observed with all the fluorescein labeled probes (DNA or PNA). Consequently, the data suggests that the nature of the labels or label pair (Beacon Set) may be the most significant factor affecting the dynamic range of the signal to noise ratios observed for a single probe in the different Buffers. This data tends to suggest that much of the dynamic range in signal to noise may be related to the nature of the labels thereby further strengthening the argument that structure and function of Linear Beacons are fairly independent of the presence or absence of magnesium and the ionic strength of the environment, as compared with DNA probes, since most of the dynamic range observed in different Buffers is likely attributable to the nature of the labels and not the structure or function of the Linear Beacon. By comparison, the broad dynamic range of the signal to noise ratio and the length dependency of the noise (See: Example 17) observed for the DNA probes indicates that the composition of the environment can have a substantial effect on the structure and function of a DNA probe.

Example 19

Detection of PCR Amplicons Using Linear Beacons

For this example, asymmetric PCR was evaluated for comparison with traditional PCR because asymmetric PCR yields a significant excess of single stranded nucleic acid. Since it is possible to choose which of the strands of the amplicon are preferentially amplified by judicious adjustment of the ratio of 5' and 3' primers, it was possible to design the assay so that the target sequence to which the Linear Beacon hybridizes was contained within the over produced single stranded nucleic acid of the asymmetric PCR assay.

Consequently, a Linear Beacon was designed to hybridize to one of the strands of a region of dsDNA sought to be amplified. The Linear Beacon was added to the PCR cocktail before thermocycling. Though Linear Beacons may hybridize to the target sequence during thermocycling, significant inhibition of the amplification process was not observed. Consequently, the PCR amplification was successfully monitored using the detectable fluorescent signal of the Linear Beacon which was generated in response to the activity of the PCR reaction. The data presented conclusively demonstrates the feasibility of using Linear Beacons for the detection of amplified nucleic acid in a closed tube (homogeneous) assay whether traditional or asymmetric PCR was used.

Materials and Methods:

PCR reactions were performed in mini-eppendorf tubes in a Perkin-Elmer 2400 thermocycler. The PCR protocol involved a 5 second warm up to 94° C. (1st cycle only), followed by denaturing at 94° C. for 5 seconds, annealing at 55° C. for 30 seconds, and extension at 74° C. for 30 seconds. The denaturation-annealing-extension cycle was repeated for 45 cycles. Samples of 10 µL were withdrawn from each PCR reaction at the end of the 30 second extension step at cycles 30, 35, 40 and 45. All 10 µL samples were placed in a 96 well conical bottom microtiter plate and fluorescence was monitored using a Wallac 1420 Victor™ Multilabel plate reader. The average fluorescence intensity was recorded in relative light units (RLU) over 1.0 second (excitation filter wavelength 485 nm; emission filter wavelength 535 nm).

All PCR reactions were derived from a single "master mix" to which were added either plasmid (for positive reactions) or plasmid buffer (negative reactions). PCR reactions containing 1 µL of plasmid DNA or plasmid buffer (10 mM TRIS-HCl pH 8.0, 1 mM EDTA) as a control, 50 pmole of the 5' primer, variable amounts the 3' primer as described below, 1 µL of 10 pmole/µL Linear Beacon, PNA003.MU (Table 1B) in 50% aqueous N,N'-dimethylformamide, 3 mM MgCl$_2$, 250 µM ATP, 250 µM GTP, 250 µM GTP, 250 µM TTP, 2.85 units AmpliTaq DNA polymerase, 50 mM KCl, and 10 mM TRIS-HCl pH 8.3. in a total volume of 50 µL were prepared. The ratio of 5' primer to 3' primer was either 1:1 (50 pmole 3' primer), 10:1 (5 pmole 3' primer), or 100:1 (0.5 pmole 3' primer).

The plasmid, pKRASMU, was generated by cloning a PCR amplicon from human DNA into the pCR2.1 plasmid (Invitrogen). The human DNA was prepared from a cell line, Calu-1, which contains a point mutation at base 129 of the K-ras gene. Clones were screened by restriction fragment analysis and sequenced. Large preparations of the plasmid were generated and quantitated using standard techniques. The amplified region flanks the K-ras mutation and was 111 bp in length. PCR reactions which were not thermocycled were used as fluorescence controls.

Probes and Primers and Targets:

```
5' primer
                                    Seq. ID No. 7
5' ATGACTGAATATAAACTTGT 3'

3' primer
                                    Seq. ID No. 8
5' CTCTATTGTTGGATCATATT 3'
``` dsDNA Template (amplified region only)

```
           <-3' primer hyb. site ->
        5' GAGATAACAACCTAGTATAAGCAGGTGTTTTACTAAGACTTA . . .   Seq. ID No. 9
        3' CTCTATTGTTGGATCATATTCGTCCACAAAATGATTCTGAATT . . .  Seq. ID No. 10

<-Linear Beacon Hyb. site->
        . . . ATCGACTTAGCAGTTCCGTGAGAACGGATGCGGTGTTCGAGGT
        . . . AGCTGTATCGTCAAGGCACTCTTGCCTACGCCACAAGCTCCAAC TGATGGTGTTCAAATATAAGTCAGTA 3'
        TACCACAAGTTTATATTCAGTCAT    5'
              <-5' primer hyb. site->
```

As illustrated above, the Linear Beacon, PNA003.MU, was designed such that it does not overlap the primer regions.

Results and Discussion:

Table 4 presents the fluorescence data recorded for PCR reactions at cycles 30, 35, 40, and 45. For convenience of discussion, the rows of the Table have been assigned numbers 1-6 and the columns have been assigned letters A-G. Average background, from controls which did not undergo thermocycling, has been subtracted from the data presented in the Table.

TABLE 4

PCR Data

| | A | B | C | D | E | F | G |
|---|---|---|---|---|---|---|---|
| 1 | Primers 5':3' | 50:50 | 50:50 | 50:5 | 50:5 | 50:0.5 | 50:0.5 |
| 2 | pKRASMU | – | + | – | + | – | + |
| 3 | 30 Rnds | 420 | 1458 | 166 | 8804 | 340 | 450 |
| 4 | 35 Rnds | 548 | 1746 | 440 | 11694 | 580 | 2458 |
| 5 | 40 Rnds | 368 | 1308 | –280 | 8552 | 12 | 2012 |
| 6 | 45 Rnds | 386 | 1412 | 438 | 10698 | 636 | 3976 |

With reference to Table 4, the ratios of the 5' and 3' primers, respectively, which were used in each assay are listed in row 1. The symbol found on row 2 of the table is used to indicate the presence (+) or absence (–) of 1 fmole of the pKRASMU plasmid (PCR template) in each assay. Rows 3-6 of column A indicate total cycles of PCR which were performed to generate the data presented.

Data for reactions containing no template (columns B, D and F) range in value from –280 to 636, with an average of 338, whereas data for reactions containing template (columns C, E, and G) are significantly higher in all cases except row 3, column G. Additionally, the intensity of fluorescence of samples containing template exhibits a correlation between the ratio of primers and the number of PCR cycles. For example, the data for a standard PCR reaction (column C), where equivalent amounts of 5' and 3' primers are used, exhibited a fairly consistent fluorescence intensity at all cycles for which data was recorded. By comparison, the fluorescence for asymmetric PCR (column E), wherein the 5' to 3' primer ratio was 10:1, was substantially more intense. This data suggests that the 10:1 ratio of 5' primer to 3' primer facilitates robust amplification which significantly overexpresses the single stranded nucleic acid containing the target sequence.

The fluorescence for asymmetric PCR (column G), wherein the 5' to 3' primer ratio was 100:1, was not as intense by comparison with the data in column G. However, the asymmetric PCR did exhibit a clear correlation between increasing number of PCR cycles and the intensity of fluorescence. The lower fluorescence observed at a primer ratio of 100:1 is likely the result of a lower total abundance of target sequence containing single stranded nucleic acid which is caused by having ten fold less 3' primer in the initial cycles of the PCR amplification reaction as compared with the sample whose data is presented in column E.

Figure 5:
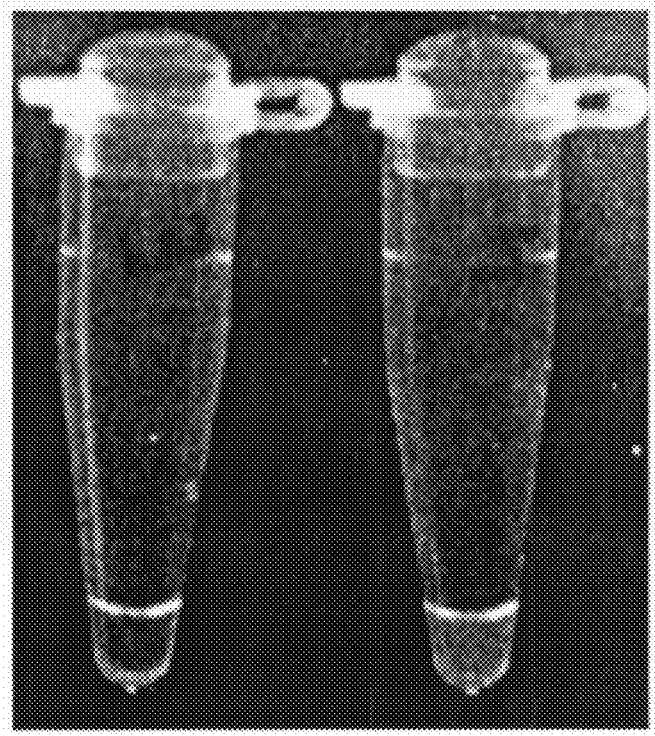
FIG. 5 is a digital image of two eppendorf tubes each containing contents of a reaction which underwent 45 cycles of PCR and containing a Linear Beacon.

FIG. 5 is a digital image of a photo of the sample (~10 μL) remaining in tubes 3 and 4 after 45 cycles of PCR. Tube 3 (left) corresponds to the data presented in row 6, column D, and tube 4 (right) corresponds to the data presented in row 6, column E. The photo was taken on a UV transilluminator. Tube 4, which contained template, is fluorescent by visual inspection whereas, tube 3, which was a control not containing template is not visibly fluorescent thereby confirming a negative result by mere visual inspection.

Taken as a whole, the data presented in this example demonstrates that Linear Beacons can be used to detect nucleic acid which has been amplified in a closed tube (homogeneous) assay. For asymmetric PCR reactions, the intensity of fluorescent signal was not only substantially higher but asymmetric PCR was shown to exhibit a correlation between the number of cycles performed and signal intensity. Thus, quantitation of amplified nucleic was possible using this method.

Example 20

PNA-FISH with Linear Beacons

Individual 3 mL cultures of bacteria were grown overnight in Tryptic Soy Broth (TSB) at 30° C. The $OD_{600}$ of each sample was measured and then each culture was diluted into fresh TSB to an $OD_{600}$ of 0.5. Cultures were allowed to double 3-4 times before harvesting. Cells from a 20 mL culture were pelleted by centrifugation at 8000 rpm. for 5 minutes, resuspended in 20 mL PBS (7 mM $Na_2HPO_4$; 3 mM $NaH_2PO_4$; 130 mM NaCl), pelleted again and resuspended in Fixation Buffer (3% paraformaldehyde in PBS). The bacteria were incubated at room temperature for 30-60 minutes before they were pelleted again (centrifugation at 8000 rpm for 5 minutes) and after removal of the fixation solution, resuspended in 20 mL of 50% aqueous ethanol. The fixed bacteria may either be used after 30 minutes of incubation at ambient temperature or stored at –20° C. for several weeks prior to use.

For each assay, 100 μL of fixed cells in 50% aqueous ethanol was transferred to a 1.5 mL microcentrifuge tube and centrifuged at 8000 rpm. for 5 min. The aqueous ethanol was then removed and the pellet was resuspended in 100 μL of sterile PBS and pelleted again by centrifugation at 8000 rpm. for 5 min. The PBS was removed from the pellet, and the cells were resuspended in 100 μL of hybridization buffer (25 mM Tris-HCl, pH 9.0; 100 mM NaCl; 0.5% SDS) which contained the appropriate Linear Beacon(s) at a concentration of approximately 30 pmol/mL. The hybridization reaction was performed at 50° C. for 30 minutes. The Linear Beacons and their target organisms are listed in Table 1C. The *Pseudomonas* probes were used in a mixture of 1 to 1 for each hybridization wherein the concentration of each probe was 30 pmol/mL in each hybridization reaction.

The sample was then centrifuged at 8000 R.P.M. for 5 min. The hybridization buffer was removed and the cells resuspended in 100 μL sterile TE-9.0 (10 mM Tris-HCl, pH 9.0; 1 mM EDTA). An aliquot of 2 μL of this suspension of cells was placed on a glass slide, spread and allowed to dry. Lastly, 2 μL Vectashield (Vector Laboratories, P/N H-1000) was deposited over the dried cells and a coverslip was added and its position fixed using a couple of drops of nail polish.

The slides were inspected using a Nikon fluorescent microscope equipped with a 60× immersion oil objective, a 10× ocular (total enlargement is 600 fold) and light filters obtained from Omega Optical (XF22 (green) and XF34 (red)). Electronic digital images of portions of the slides were made using a SPOT CCD-camera and software obtained from Diagnostic Instruments, Inc., Sterling Heights, Mich. (USA).

Figure 6B:
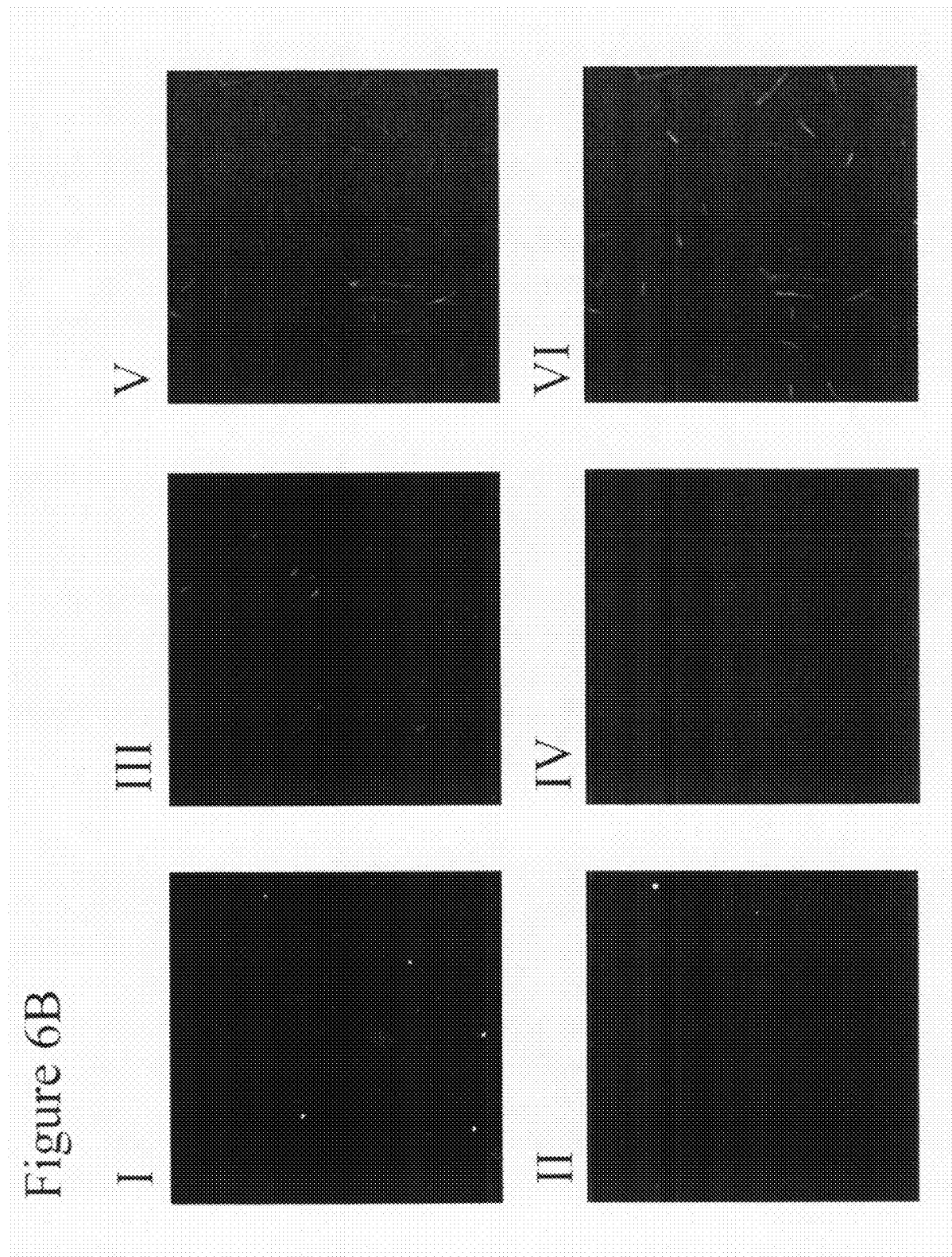

The digital images obtained are presented in FIGS. 6A and 6B. Fixed *E. coli*, *P. aeruginosa*, and *B. subtilis* cells were all hybridized with either a *P. aeruginosa* (FIG. 6A) or a *B. subtilis* (FIG. 6B) Linear Beacon as described above. In both FIGS. 6A and 6B, the red images presented in panels I, III and V are of cells stained with propidium iodide which were visible using the red microscope filter. In both FIGS. 6A and 6B, the green images presented in panels II, IV and VI are of cells having a green fluorescence caused by hybridization of the fluorescein labeled Linear Beacon to the rRNA target sequence and which are visible using the green microscope filter. For comparative purposes, the red and green images for each probe examined are of the same section of each slide and are presented one over the other in the Figures.

With reference to FIG. 6A, the cells of *E. coli*, *P. aeruginosa* and *B. subtilis* can be seen in the red images presented in panels I, III and V, respectively. The cells are red since the propidium iodide will stain all the bacterial which are present.

With reference to Panels, II, IV and VI of FIG. 6A, green cells are most intensely visible only in panel IV thereby confirming that the Linear Beacon can be used to specifically identify the presence of the target organism *P. aeruginosa*.

With reference to FIG. 6B, again the cells of *E. coli, P. aeruginosa* and *B. subtilis* can be seen in the red images presented in panels I, III and V, respectively. With reference to Panels, II, IV and VI of FIG. 6B, green cells are most intensely visible only in panel VI thereby confirming that the Linear Beacon can be used to specifically identify the presence of the target organism *B. subtilis*.

In summary, the Linear Beacons directed to *P. aeruginosa* and *Bacillus* provide for the unambiguous detection of target organisms even though the protocol does not include any washing steps after the hybridization reaction is performed.

Example 21

Correlation of Noise and Signal to Noise with Nucleobase Sequence

This example was performed to determine whether the phenomena observed by applicants was sequence dependent. Therefore the nucleobase sequence of PNA probe Cy3PNA003-15 (See: Table 1B) was rearranged to produce the probe Cy3SCBL03-15 (See: Table 1B).

Materials and Methods:

The preparation, labeling and purification of PNA oligomers has been described. The probe Cy3SCBL03-15 was examined in Buffers B and C essentially as described in Example 18 of this specification using the DNA target SCBL-DNA (See: Table 2A). The data obtained is graphically represented in FIGS. 7A and 7B.

Results and Discussion:

With reference to FIG. 7A, the raw signal and noise data is illustrated for the two buffer examined. As was observed for the probe Cy3PNA003-15, the results for probe Cy3SCBL03-15 appear to be substantially independent of the buffer thereby confirming that ionic strength and a minimal pH change does not effect the results. With reference to FIG. 7B, the signal to noise ratio is approximately 6-8 upon hybridization to the target sequence. This correlates well the data presented in FIG. 4E for the probe Cy3PNA003-15. Therefore, the data indicates that the phenomena observed by applicants is not substantially dependent upon the nucleobase sequence of the Linear Beacon.

EQUIVALENTS

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A method for determining a PCR amplified nucleic acid, said method comprising:
   a) contacting a sample comprising nucleic acid to be PCR amplified with at least one polymer comprising at least one linked energy donor moiety and at least one linked energy acceptor moiety wherein said donor and acceptor moieties are separated by at least a portion of a probing nucleobase sequence and wherein said polymer does not form a stem and loop hairpin and is further characterized in that the efficiency of transfer of energy between said donor and acceptor moieties, when the polymer is solvated in aqueous solution, is substantially independent of at least two variables selected from the group consisting of:
      i) nucleobase sequence length separating the at least one energy donor moiety from the at least one energy acceptor moiety;
      ii) spectral overlap of the at least one linked energy donor moiety and the at least one linked energy acceptor moiety;
      iii) presence or absence of magnesium in the aqueous solution; and the
      iv) ionic strength of the aqueous solution;
   b) contacting the sample with primers and other reagents for PCR amplification;
   c) PCR amplifying the nucleic acid;
   d) determining hybridization of the polymer to a target sequence within the amplified nucleic acid wherein the target sequence present in the sample is correlated with a change in detectable signal associated with at least one donor or acceptor moiety of the polymer; and
   e) determining the presence, absence or amount of PCR amplified nucleic acid in the sample.

2. The method of claim 1, wherein the nucleic acid to be amplified is contained within a plasmid.

3. The method of claim 1, wherein the PCR amplification is traditional.

4. The method of claim 1, wherein the PCR amplification is asymmetric.

5. The method of claim 1, wherein the PCR amplification is performed as a closed tube (homogeneous) assay.

6. The method of claim 1, wherein the amplified nucleic acid is quantitated.

7. The method of claim 1, wherein the presence or absence of the amplified nucleic acid is determined.

8. The method of claim 1, wherein the polymer is a peptide nucleic acid.

9. A method for determining a PCR amplified nucleic acid, said method comprising:
   a) contacting a sample comprising nucleic acid to be PCR amplified with a polymer comprising:
      i) a probing nucleobase sequence for probing a target sequence to which the probing nucleobase sequence is complementary or substantially complementary;
      ii) at least one energy donor moiety that is linked to the probing nucleobase sequence; and
      iii) at least one energy acceptor moiety that is linked to the probing nucleobase sequence wherein the at least one donor moiety is separated from the at least one acceptor moiety by at least a portion of the probing nucleobase sequence;
   b) contacting the sample with primers and other reagents for PCR amplification;
   c) PCR amplifying the nucleic acid;
   d) determining hybridization of the polymer to a target sequence within the amplified nucleic acid wherein the target sequence present in the sample is correlated with a change in detectable signal associated with at least one donor or acceptor moiety of the polymer; and
   e) determining the presence, absence or amount of PCR amplified nucleic acid in the sample.

10. The method of claim 9, wherein the nucleic acid to be amplified is contained within a plasmid.

11. The method of claim 9, wherein the PCR amplification is traditional.

12. The method of claim 9, wherein the PCR amplification is asymmetric.

13. The method of claim 9, wherein the PCR amplification is performed as a closed tube (homogeneous) assay.

14. The method of claim 9, wherein the amplified nucleic acid is quantitated.

15. The method of claim 9, wherein the presence or absence of the amplified nucleic acid is determined.

16. The method of claim 9, wherein the polymer is a peptide nucleic acid.

* * * * *